United States Patent
Gao et al.

(10) Patent No.: US 10,590,435 B2
(45) Date of Patent: *Mar. 17, 2020

(54) ADENO-ASSOCIATED VIRUS (AAV) SEROTYPE 8 SEQUENCES, VECTORS CONTAINING SAME, AND USES THEREFOR

(71) Applicant: The Trustees of the University of Pennsylvania, Philadelphia, PA (US)

(72) Inventors: Guangping Gao, Westborough, MA (US); James M. Wilson, Philadelphia, PA (US); Mauricio R. Alvira, Philadelphia, PA (US)

(73) Assignee: The Trustees of the University of Pennsylvania, Philadlephia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/142,921

(22) Filed: Sep. 26, 2018

(65) Prior Publication Data

US 2019/0017068 A1    Jan. 17, 2019

Related U.S. Application Data

(60) Continuation of application No. 15/298,760, filed on Oct. 20, 2016, now Pat. No. 10,266,846, which is a division of application No. 14/598,462, filed on Jan. 16, 2015, now Pat. No. 9,493,788, which is a division of application No. 11/981,022, filed on Oct. 31, 2007, now Pat. No. 8,962,330, which is a continuation of application No. 11/899,500, filed on Sep. 6, 2007, now Pat. No. 7,790,449, which is a continuation of application No. 10/423,704, filed on Apr. 25, 2003, now Pat. No. 7,282,199, which is a continuation-in-part of application No. PCT/US02/33630, filed on Nov. 12, 2002.

(60) Provisional application No. 60/386,122, filed on Jun. 5, 2002, provisional application No. 60/377,133, filed on May 1, 2002, provisional application No. 60/341,151, filed on Dec. 17, 2001.

(51) Int. Cl.
| | |
|---|---|
| C12N 15/86 | (2006.01) |
| C12N 15/864 | (2006.01) |
| C07K 14/005 | (2006.01) |
| C07K 14/755 | (2006.01) |
| C12N 7/00 | (2006.01) |
| A61K 35/761 | (2015.01) |
| A61K 38/17 | (2006.01) |
| A61K 38/45 | (2006.01) |
| A61K 38/48 | (2006.01) |
| C07K 14/705 | (2006.01) |
| C12N 9/10 | (2006.01) |
| C12N 9/64 | (2006.01) |
| A61K 9/00 | (2006.01) |
| A61K 48/00 | (2006.01) |

(52) U.S. Cl.
CPC ............ *C12N 15/86* (2013.01); *A61K 9/0019* (2013.01); *A61K 35/761* (2013.01); *A61K 38/177* (2013.01); *A61K 38/45* (2013.01); *A61K 38/4846* (2013.01); *C07K 14/005* (2013.01); *C07K 14/705* (2013.01); *C07K 14/755* (2013.01); *C12N 7/00* (2013.01); *C12N 9/1018* (2013.01); *C12N 9/644* (2013.01); *C12N 15/8645* (2013.01); *C12Y 304/21021* (2013.01); *C12Y 304/21022* (2013.01); *A61K 48/00* (2013.01); *C12N 2750/14122* (2013.01); *C12N 2750/14143* (2013.01); *C12N 2750/14152* (2013.01); *C12N 2830/008* (2013.01); *C12N 2830/48* (2013.01); *C12N 2830/85* (2013.01); *C12Y 201/03003* (2013.01)

(58) Field of Classification Search
None
See application file for complete search history.

(56) References Cited

U.S. PATENT DOCUMENTS

| | | |
|---|---|---|
| 5,866,552 A | 2/1999 | Wilson et al. |
| 5,871,982 A | 2/1999 | Wilson et al. |
| 6,156,303 A | 12/2000 | Russell et al. |
| 6,251,677 B1 | 6/2001 | Wilson et al. |
| 6,258,595 B1 | 7/2001 | Gao et al. |
| 6,274,354 B1 | 8/2001 | Wilson et al. |
| 6,312,957 B1 | 11/2001 | Einerhand et al. |
| 6,365,394 B1 | 4/2002 | Gao et al. |
| 6,387,368 B1 | 5/2002 | Wilson et al. |
| 6,399,385 B1 | 6/2002 | Croyle et al. |
| 6,428,988 B1 | 8/2002 | Wilson et al. |
| 6,468,524 B1 | 10/2002 | Chiorini et al. |

(Continued)

FOREIGN PATENT DOCUMENTS

| | | |
|---|---|---|
| EP | 1310571 A2 | 5/2003 |
| WO | WO 96/00587 A1 | 1/1996 |

(Continued)

OTHER PUBLICATIONS

Score report result for Bartlett et al (U.S. Appl. No. 11/145,035 & U.S. Appl. No. 10/038,972) (Year: 2005).*

(Continued)

*Primary Examiner* — Catherine S Hibbert
(74) *Attorney, Agent, or Firm* — Howson & Howson LLP; Colleen M. Schaller

(57) ABSTRACT

Sequences of a serotype 8 adeno-associated virus and vectors and host cells containing these sequences are provided. Also described are methods of using such host cells and vectors in production of rAAV particles.

25 Claims, 9 Drawing Sheets

Specification includes a Sequence Listing.

(56) References Cited

U.S. PATENT DOCUMENTS

| | | | |
|---|---|---|---|
| 6,475,769 | B1 | 11/2002 | Wilson et al. |
| 6,482,634 | B1 | 11/2002 | Wilson et al. |
| 6,485,966 | B2 | 11/2002 | Gao et al. |
| 6,759,237 | B1 | 7/2004 | Wilson et al. |
| 6,821,512 | B1 | 11/2004 | Gao et al. |
| 6,943,019 | B2 | 9/2005 | Wilson et al. |
| 6,953,690 | B1 | 10/2005 | Gao et al. |
| 6,962,815 | B2 * | 11/2005 | Bartlett .................... C12N 7/00 424/199.1 |
| 7,022,519 | B2 | 4/2006 | Gao et al. |
| 7,056,502 | B2 | 6/2006 | Hildinger et al. |
| 7,115,391 | B1 | 10/2006 | Chen et al. |
| 7,198,951 | B2 | 4/2007 | Gao et al. |
| 7,238,526 | B2 | 7/2007 | Wilson et al. |
| 7,282,199 | B2 | 10/2007 | Gao et al. |
| 7,790,449 | B2 | 9/2010 | Gao et al. |
| 8,318,480 | B2 | 11/2012 | Gao et al. |
| 2001/0006955 | A1 | 7/2001 | Wilson et al. |
| 2002/0037867 | A1 | 3/2002 | Wilson et al. |
| 2002/0045264 | A1 | 4/2002 | During et al. |
| 2002/0090717 | A1 | 7/2002 | Gao et al. |
| 2002/0192823 | A1 | 12/2002 | Bartlett et al. |
| 2003/0138772 | A1 | 7/2003 | Gao et al. |
| 2005/0112103 | A1 | 5/2005 | Wilson et al. |
| 2005/0287122 | A1 | 12/2005 | Bartlett et al. |
| 2007/0036760 | A1 | 2/2007 | Wilson et al. |

FOREIGN PATENT DOCUMENTS

| | | |
|---|---|---|
| WO | WO 96/13598 A3 | 5/1996 |
| WO | WO 98/09657 A2 | 3/1998 |
| WO | WO 98/10086 A1 | 3/1998 |
| WO | WO 98/10088 A1 | 3/1998 |
| WO | WO 98/11244 A1 | 3/1998 |
| WO | WO 99/14354 A1 | 3/1999 |
| WO | WO 99/15677 A1 | 4/1999 |
| WO | WO 99/15685 A1 | 4/1999 |
| WO | WO 99/14769 A1 | 9/1999 |
| WO | WO 99/61601 A2 | 12/1999 |
| WO | WO 00/28061 A3 | 5/2000 |
| WO | WO 00/75353 A1 | 12/2000 |
| WO | WO 01/23001 A2 | 4/2001 |
| WO | WO 01/23597 A3 | 4/2001 |
| WO | WO 01/25462 A1 | 4/2001 |
| WO | WO 01/40455 A3 | 6/2001 |
| WO | WO 01/70276 A2 | 9/2001 |
| WO | WO 01/83692 A2 | 11/2001 |
| WO | WO 02/18659 A2 | 3/2002 |
| WO | WO 03/104392 A2 | 12/2003 |

OTHER PUBLICATIONS

Gao et al "Novel adeno-associated viruses from rhesus monkeys as vectors for human gene therapy" Journal of Virology Jun. 2004 pp. 6381-6388. (Year: 2004).*

Gao G.P., Alvira M.R., Wang L., Calcedo R., Johnston J., Wilson J.M.; "Novel adeno-associated viruses from rhesus monkeys as vectors for human gene therapy." (Proc. Natl. Acad. Sci. U.S.A. 99:11854-11859; 2002; IDS reference (Year: 2002).*

Gao et al "Clades of Adeno-Associated Viruses Are Widely Disseminated in Human Tissues" (Journal of Virology, Jun. 2004, pp. 6381-6388; IDS reference) (Year: 2004).*

Afione SA et al., In vivo model of adeno-associated virus vector persistence and rescue, Journal of Virology, vol. 70(5):3235-3241, May 1996.

Bantel-Schaal U et al., Human adeno-associated virus type 5 is only distantly related to other known primate helper-dependent parvoviruses, Journal of Virology, vol. 73(2):939-947, Feb. 1999.

Black A et al., Adeno-associated virus 8-mediated gene therapy for choroideremia: preclinical studies in in vitro and in vivo models, The Journal of Gene Medicine, vol. 16:122-130, Jun. 24, 2014.

Brown KE et al., Cloning and sequencing of the simial parvovirus genome, Virology, vol. 210:314-322, May 1995.

Calcedo R et al., Serologic Characterization of Human and Non-Human Primate AAVs, Abstract 102, Molecular Therapy, vol. 7(5): S41, May 2003.

Charan RA et al., Adeno-associated Virus Serotype 8 (AAV8) Delivery of Recombinant A20 to Skeletal Muscle Reduces Pathological Activation of Nuclear Factor (NF)-kB in Muscle of mdx Mice, Molecular Medicine, vol. 18:1527-35, Feb. 2013. (Epub Nov. 6, 2012).

Childers MK et al., Gene Therapy Prolongs Survival and Restores Function in Murine and Canine Models of Myotubular Myopathy, Sci Transl Med, vol. 6(220):1-31, Jan. 22, 2014.

Chiorini JA et al., Cloning and characterization of AAV5, Journal of Virology, vol. 73(2):1309-1319, Feb. 1999.

Chirmule N et al., Humoral Immunity to Adeno-Associated Virus Type 2 Vectors following Administration to Murine and Nonhuman Primate Muscle, Journal of Virology, 74(5):2420-5, Mar. 2000.

ClinicalTrials.org, "AAV8 Vector Trials", Nov. 2017.

Cronin T et al., Efficient transduction and optogenetic stimulation of retinal bipolar cells by a synthetic adeno-associated virus capsid and promoter, EMBO Mol Med, 6(9):1175-90, Sep. 2014.

Dai X et al., Long-term retinal cone rescue using a capsid mutant AAV8 vector in a mouse model of CNGA3-achromatopsia, PLOS One, vol. 12(11):e0188032, Nov. 13, 2017.

De BP et al., Therapeutic Levels for alpha1-Antitrypsin Following Intrapleural Administration of a Non-Human Primate Serotype rh10 AAV Vector Expressing alpha1-Antitrypsin, Abstract 338, 7$^{th}$ Annual Meeting of The American Society of Gene Therapy [Jun. 2-6, 2004] Minneapolis, Minnesota, p. 1, e-published May 2, 2004.

Durigon EL et al., Multiple primer pairs for polymerase chain reaction (PCR) amplification of human parvovirus B19 DNA, Journal of Virological Methods, vol. 44:155-65, Feb. 1993.

Fischer MD et al., Codon-Optimized RPGR Improves Stability and Efficacy of AAV8 Gene Therapy in Two Mouse Models of X-Linked Retinitis Pigmentosa, Molecular Therapy, vol. 25(8):1854-65, Aug. 2, 2017. (Epub May 24, 2017).

Forslund O et al., A broad range of human papillomavirus types detected with a general PCR method suitable for analysis of cutaneous tumors and normal skin, Journal of General Virology, vol. 80(9):2437-43, XP002229850, Sep. 1999.

Gao G et al., Clades of Adeno-Associated Viruses are Widely Disseminated in human Tissues, Journal of Virology, vol. 78(12):6381-6388, Jun. 2004.

Gao G et al., Diversity of Latent AAV Genomes in Non-Human Primate and Human Tissues, Abstract 400, Molecular Therapy, vol. 7(5):S158, May 2003.

Gao G et al., Erythropoietin Gene Therapy Leads to Autoimmune Anemia in Macaques, Blood, vol. 103(9):3300-2, May 2004.

Gao GP et al., Biology of Adenovirus vectors with E1 and E4 deletions for liver-directed gene therapy, Journal of Virology, vol. 70(12):8934-8943, Dec. 1996.

Gao GP et al., Novel adeno-associated viruses from rhesus monkeys as vectors for human gene therapy, PNAS, vol. 99(18):11854-59, Sep. 2002. (Epub Aug. 21, 2002).

GenBank entry AF513851, Sep. 2002.

GenBank entry AF513852, Sep. 2002.

Gilkes JA et al., Mucopolysaccharidosis IIIB confers enhanced neonatal intracranial transduction by AAV8 but not by 5, 9 or rh10, Gene Therapy, vol. 23(3):263-271, Mar. 2016. (Epub Dec. 16, 2015).

Green SW et al., Rhesus and pig-tailed macaque parvoviruses: identification of two new members of the erythrovirus genus in monkeys, Virology, vol. 269:105-12, Mar. 30, 2000.

Hernandez YJ et al., Latent Adeno-associated virus infection elicits humoral but no cell-mediated immune responses in a nonhuman primate model, Journal of Virology, vol. 73(10):8549-8558, Oct. 1999.

Kassim SH et al., Adeno-associated virus serotype 8 gene therapy leads to significant lowering of plasma cholesterol levels in humanized mouse models of homozygous and heterozygous familial hypercholesterolemia, Human Gene Therapy, 24(1):19-26, Jan. 2013. (Epub Nov. 14, 2012).

(56) References Cited

OTHER PUBLICATIONS

Kassim SH et al., Gene therapy in a humanized mouse model of familial hypercholesterolemia leads to marked regression of atherosclerosis, PLoS One, 5(10):e13424 (10 pages), Oct. 19, 2010.

Kay MA et al., Evidence for gene transfer and expression of factor IX in haemophilia B patients treated with an AAV vector, Nature Genetics, 24(3):257-61, Mar. 2000.

Lebherz C et al., Gene Therapy with Novel Adeno-Associated Virus Vectors Substantially Diminishes Atherosclerosis in a Murine Model of Familial Hypercholesterolemia, The Journal of Gene Medicine, vol. 6(6):663-672, Jun. 2004.

Limberis M et al., A Novel AAV Vector for the Treatment of Cystic Fibrosis Airway Disease, Abstract 692, 7th Annual Meeting of The American Society of Gene Therapy [Jun. 2-6, 2004] Minneapolis, Minnesota, p. 1, e-published May 2, 2004.

Lu Y et al., Analysis of Homologous Recombination Between Different AAV Genomes in In Vitro co-Infections, Abstract 38, Molecular Therapy, vol. 7(5):S15, May 2003.

Lytle AM et al., Effects of FVIII immunity on hepatocyte and hematopoietic stem cell-directed gene therapy of murine hemophilia A, Methods & Clinical Development, vol. 3:15056, Feb. 10, 2016.

Mizukami et al, AAV 8 Mediated Transgene Expression in Mice and Non-Human Primates, American Society of Gene Therapy, 9th Annual Meeting, Abstract, (May 31-Jun. 4, 2006).

Molecular Therapy, "Information for Authors", pp. 1-13.

Mountz JD et al., Monkey See, Monkey Do, Gene Therapy, vol. 10(3):194-6, Feb. 2003.

Pignataro D et al., Adeno-Associated Viral Vectors Serotype 8 for Cell-Specific Delivery of Therapeutic Genes in the Central Nervous System, Frontiers in Neuroanatomy, vol. 11(2):1-13, Feb. 10, 2017.

Rick ME et al., ASH education Book—Congenital Bleeding Disorders, Hematology/American Society of Hematology Educational Program, vol. 2003(1):559-74, Jan. 1, 2003.

Rutledge EA et al., Infectious clones and vectors derived from adeno-associated virus (AAV) serotypes other than AAV type 2, Journal of Virology, vol. 72(1):309-319, XP-002137089, Jan. 1998.

Sanmiguel J et al., Real-time PCR as an Analytic Tool in Gene Therapy, Abstract 913, vol. 7(5):S352, May 2003.

Sarkar et al, Total Correction of Hemophilia a Mice with Canine FVIII Using an AAV 8 Serotype, Blood First Edition Paper, 103(4), pp. 1253-1260, published online Oct. 9, 2003.

Schnell MA et al., Activation of innate immunity in nonhuman primates following intraportal administration of adenoviral vectors, Molecular Therapy, vol. 3(5):708-722, May 2001.

Smith-Arica JR and Bartlett JS, Gene Therapy: recombinant adeno-associated virus vectors, Current Cardiology Reports, 3(1):43-9, Jan. 2001.

Sun B et al., Efficacy of an adeno-associated virus 8-pseudotyped vector in glycogen storage disease type II, Molecular Therapy, 11(1):57-65, Jan. 2005.

Vandenberghe LH et al., AAV Clades: Their Ability to Recombine and Cross Species-Barriers, Abstract 88, 7th Annual Meeting of The American Society of Gene Therapy [Jun. 2-6, 2004] Minneapolis, Minnesota, p. 1, e-published May 2, 2004.

Vandenberghe LH et al., Structure-Function Relationship of the Novel Non-Human Primate Adeno-associated Viruses, Abstract 99, Molecular Therapy, vol. 7(5):S15, May 2003.

Wang L et al., Enhancing Transgene Expression from Recombinant AAV8 Vectors in Different Tissues Using Woodchuck Hepatitis Virus Post-Transcriptional Regulatory Element, International Journal of Medical Sciences, vol. 13(4):286-291, Apr. 1, 2016.

Wang L et al., Preclinical evaluation of a clinical candidate AAV8 vector for ornithine transcarbamylase (OTC) deficiency reveals functional enzyme from each persisting vector genome, Molec. Gen. and Metabolism, 105(2):203-11, Feb. 2012. (Epub Nov. 7, 2011).

Wang L et al., Production of AAV Vectors with Different Serotypes, Abstract 906, Molecular Therapy, vol. 7(5):S350, May 2003.

Wang L et al., Sustained correction of OTC deficiency in spfash mice using optimized self-complementary AAV-2/8 vectors, Gene Therapy, 19(4):404-10, Apr. 2012. (Epub Aug. 18, 2011).

Weitzman MD et al., Adeno-associated virus (AAV) Rep proteins mediate complex formation between AAV DNA and its integration site in human DNA, PNAS, vol. 91:5808-5812, Jun. 21, 1994.

Xiao W et al., Gene therapy vectors based on adeno-associated virus type 1, Journal of Virology, 73(5):3994-4003, May 1999.

Xiao X et al., Production of High-titer Recombinant Adeno-Associated Virus Vectors in the Absence of Helper Adenovirus, Journal of Virology, 72(3):2224-32, Mar. 1998.

Zadori Z et al., A viral phospholipase A2 is required for parvovirus infectivity, Developmental Cell, vol. 1:291-302, Aug. 2001.

Zhou X et al., Evaluation of Novel Gene Transfer Vectors Derived from Infectious Molecular Clones of Primate AAVs, Abstract 90, 7th Annual Meeting of The American Society of Gene Therapy [Jun. 2-6, 2004] Minneapolis, Minnesota, p. 1, e-published May 2, 2004.

Zhou XY et al., Direct Rescue and Cloning of Infectious Novel AAV Genomes From Non-Human Primate Tissues, Abstract 907, Molecular Therapy, 7(5):S350, May 2003.

Zhu T et al., Sustained Whole-Body Functional Rescue by Systemic Delivery of AAV8 Vectors in Heart Failure and Muscular Dystrophy Hamsters, Molecular Therapy, vol. 11(suppl 1):916, May 2005.

ClinicalTrials.gov, Clinical Trial NCT01687608—"Open-Label Single Ascending Dose of Adeno-associated Virus Serotype 8 Factor IX Gene Therapy in Adults with Hemophilia B", last updated Apr. 8, 2015.

ClinicalTrials.gov, Clinical Trial NCT01620801—"Hemophilia B Gene Therapy—Spark", last updated May 18, 2015.

Center for Cellular and Molecular Therapeutics at The Children's Hospital of Philadelphia (CCMT/CHOP); AAV8-hFIX19; Summary Information Format (Part 1 of Counsel Decision (2002/813/EC) of Oct. 3, 2002, pursuant to Directive 2001/18/EC of the European Parliament and of the Council; Jan. 2013, http://gmoinfo.jrc.ec.europa.eu/bsnifs-gmo/B-IE-13-01.pdf.

Aug. 12, 2010 Office Action in Canadian Patent Application No. 2,469,785.

Feb. 8, 2011 Response to Aug. 12, 2010 Office Action in Canadian Patent Application No. 2,469,785.

Mar. 22, 2011 Office Action in Canadian Patent Application No. 2,469,785.

Sep. 12, 2011 Response to Mar. 22, 2011 Office Action in Canadian Patent Application No. 2,469,785.

Jun. 26, 2012 Office Action in Canadian Patent Application No. 2,469,785.

Nov. 28, 2012 Office Action in Canadian Patent Application No. 2,469,785.

Nov. 6, 2008 Communication in European Patent Application No. 02795539.2.

May 18, 2009 Response to Nov. 6, 2008 Communication in European Patent Application No. 02795539.2.

May 24, 2010 Supplemental Response to Nov. 6, 2008 Communication in European Patent Application No. 02795539.2.

Aug. 3, 2010 Communication in European Patent Application No. 02795539.2.

Dec. 13, 2010 Response to Aug. 3, 2010 Communication in European Patent Application No. 02795539.2.

Dec. 6, 2013 Communication including European Search Report in European Patent Application No. 10189725.4.

Jul. 8, 2014 Response to Dec. 6, 2013 Communication in European Patent Application No. 10189725.4.

Jun. 14, 2016 Communication in European Patent Application No. 10189725.4.

Dec. 20, 2016 Response to Jun. 14, 2016 Communication in European Patent Application No. 10189725.4.

Jun. 9, 2017 Communication in European Patent Application No. 10189725.4.

Oct. 18, 2017 Response to Jun. 9, 2017 Communication in European Patent Application No. 10189725.4.

Jan. 17, 2018 Communication in European Patent Application No. 10189725.4.

May 15, 2018 Response to Jan. 17, 2018 Communication in European Patent Application No. 10189725.4.

(56) References Cited

OTHER PUBLICATIONS

Oct. 21, 2008 Office Action in Japanese Patent Application No. 2003-552918.
Apr. 9, 2009 Response to Oct. 21, 2008 Office Action in Japanese Patent Application No. 2003-552918.
Sep. 15, 2009 Office Action in Japanese Patent Application No. 2003-552918.
Mar. 12, 2010 Response to Sep. 15, 2009 Office Action in Japanese Patent Application No. 2003-552918.
Mar. 8, 2011 Office Action (final) in Japanese Patent Application No. 2003-552918.
Jul. 11, 2011 Response to (Appeal from) Mar. 8, 2011 Office Action in Japanese Patent Application No. 2003-552918.
May 14, 2013 Office Action in Japanese Patent Application No. 2011-152748.
Nov. 13, 2014 Response to May 14, 2013 Office Action in Japanese Patent Application No. 2011-152748.
Jul. 2, 2014 Office Action (final) in Japanese Patent Application No. 2011-152748.
Sep. 5, 2014 Response to Jul. 2, 2014 Office Action in Japanese Patent Application No. 2011-152748.
International Search Report for International Application No. PCT/US02/033630, dated Oct. 24, 2003.
International Preliminary Examination Report for International Application No. PCT/US02/033630, dated Mar. 21, 2004.
Jul. 14, 2006 Office Action in U.S. Appl. No. 10/423,704 and Response dated Dec. 11, 2006.
Mar. 8, 2007 Office Action in U.S. Appl. No. 10/423,704 and Response dated May 3, 2007.
Jun. 8, 2007 Notice of Allowance in U.S. Appl. No. 10/423,704.
Aug. 14, 2009 Office Action in U.S. Appl. No. 11/899,500 and Response dated Jan. 29, 2010.
Apr. 7, 2010 Notice of Allowance in U.S. Appl. No. 11/899,500.
Oct. 12, 2010 Office Action in U.S. Appl. No. 11/981,191 and Response dated Dec. 14, 2010.
Mar. 22, 2011 Office Action in U.S. Appl. No. 11/981,191 and Response dated May 27, 2011.
Jul. 20, 2011 Office Action in U.S. Appl. No. 11/981,191 and Response dated Oct. 20, 2011.
Mar. 21, 2012 Office Action in U.S. Appl. No. 11/981,191 and Response dated Jun. 15, 2012.
Jul. 25, 2012 Notice of Allowance in U.S. Appl. No. 11/981,191.
Sep. 16, 2010 Office Action in U.S. Appl. No. 11/981,022 and Response dated Dec. 14, 2010.
Feb. 17, 2011 Office Action in U.S. Appl. No. 11/981,022 and Response dated Apr. 14, 2011.
Aug. 29, 2013 Office Action in U.S. Appl. No. 11/981,022 and Response dated Nov. 29, 2013.
Mar. 31, 2014 Office Action in U.S. Appl. No. 11/981,022 and Response dated Jun. 27, 2014.
Oct. 27, 2014 Notice of Allowance in U.S. Appl. No. 11/981,022.
Feb. 27, 2014 Office Action in U.S. Appl. No. 14/025,951 and Response dated Jun. 27, 2014.
Oct. 24, 2014 Notice of Allowance in U.S. Appl. No. 14/025,951.
Jan. 14, 2016 Office Action in U.S. Appl. No. 14/598,477 and Response dated Jul. 14, 2016.
Oct. 24, 2016 Notice of Allowance in U.S. Appl. No. 14/598,477.
Nov. 20, 2015 Office Action in U.S. Appl. No. 14/598,462 and Response dated Apr. 20, 2016.
Jul. 15, 2016 Notice of Allowance in U.S. Appl. No. 14/598,462.
Feb. 15, 2017 Notice of Allowance in U.S. Appl. No. 15/084,615.
Communication of a Notice of Opposition issued in European Patent No. EP1453547 (Application No. 02795539.2) by the European Patent Office on Jun. 26, 2017 and the Statement of Opposition dated Jun. 20, 2017.
Proprietor's Response to the Opposition, dated Dec. 5, 2017, filed on related European Patent No. EP1453547.
Summons to attend oral proceedings and Communication dated Mar. 29, 2018, issued in related European Patent No. 1453547.

Nzilambi et al., The prevalence of infection with human immunodeficiency virus over a 10-year period in rural zaire, NE J Med, 318(5):276-279, Feb. 1988.
Kawamura et al., Hiv-2 in West Africa in 1966, The Lancet, Feb. 1989, 385.
Le Guenno, HIV1 and HIV2: two ancient viruses for a new disease? Transactions of the Royal Society of Tropical Medicine and Hygiene, 1989, 83, 847.
Faria et al., the early spread and epidemic ignition of HIV-1 in human populations, Science, Oct. 2014, 346(6205):56-61.
F. Gao et al., Origin of HIV-1 in the chimpanzee Pan troglodytes troglodytes, Nature, Feb. 1999, 397 :436-440.
G. Gao et al., Clades of Adeno Associated Viruses Are Widely Disseminated in Human Tissues, J. Virol, Jun. 2004, 78(12) :6381-8.
Wu et al., Mutational Analysis of the Adeno-Associated Virus Type 2 (AAV2) Capsid Gene and Construction of AAV2 Vectors With Altered Tropism, J. Virol, Sep. 2000, 74(18) :8635-47.
Moskaleno et al., Epitope Mapping of Human Anti-Adeno-Associated Virus Type 2 Neutralizing Antibodies: Implications for Gene Therapy and Virus Structure, J Virol, Feb. 2000, 74(4):1761-6.
Wobus et al., Monoclonal Antibodies against the Adeno-Associated Virus Type 2 (AAV-2) Capsid: Epitope Mapping and identification of Capsid Domains Involved in AAV-2-Cell Interaction and Neutralization of AAV-2 Infection, J Virol, Oct. 2000, 74(19) :9281-93.
Nam et al., Structure of Adeno-Associated Virus Serotype 8, a Gene Therapy Vector, J Virol, 81(22) :12260-71, Nov. 2007.
Shen et al., Characterization of the Relationship of AAV Capsid Domain Swapping to Liver Transduction Efficiency, Mol Ther, Aug. 2007, 15(11):1955-62.
Wang et al., Comparative Study of Liver Gene Transfer With AAV Vectors Based on Natural and Engineered AAV Capsids, Molecular Therapy, Dec. 2015, 23(12):1877-87.
Hu et al., RH10 provides superior transgene expression in mice when compared with natural AAV serotypes for neonatal gene therapy, J. Gene Med, Sep. 2010, 12(9): 766-778.
Girod et al., The VP1 capsid protein of adeno-associated virus type 2 is carrying a phospholipase A2 domain required for virus infectivity, J. General Virol, 2002, 83:973-978.
Grieger et al, Surface-Exposed Adeno-Associated Virus Vpl-NLS Capsid Fusion Protein Rescues Infectivity of Noninfectious Wild-Type Vp2/Vp3 and , Vp3-Only Capsids but Not That of Fivefold Pore Mutant Virions, J. Virol, 81(15):7833-7483, Aug. 2007.
Warrington et al, Adeno-Associated Virus Type 2 VP2 Capsid Protein Is Nonessential and Can Tolerate Large Peptide Insertions at Its N Terminus, J Virol, 78(1):6595-6609, Jun. 2004.
Li et al, 2015, Site-Directed Mutagenesis of Surface-Exposed Lysine Residues Leads to Improved Transduction by AAV2,But Not AAV8, Vectors in Murine Hepatocytes In Vivo, Hum Gene Ther Methods. Oct. 2015;26(6):211-20.
Grosse et al, Relevance of Assembly-Activating Protein for Adeno-associated Virus Vector Production and Capsid Protein Stability in Mammalian and Insect Cells, J Virol 91:e01198-17, Aug. 2017.
Sonntag et al, A viral assembly factor promotes AAV2 capsid formation in the nucleolus, PNAS, 107(22):10220-5, Jun. 2010.
Liu et al, Neutralizing antibodies against AAV2, AAV5 and AAV8 in healthy and HIV-1-infected subjects in China: implications for gene therapy using AAV vectors, Gene Therapy, 21:732-738, May 2014.
Mimuro et al, The Prevalence of Neutralizing Antibodies Against Adeno-Associated Virus Capsids Is Reduced in Young Japanese Individuals, J. Med Virol, 86:1990-7 Oct. 2013.
Vercauteren, Superior In vivo Transduction of Human Hepatocytes Using Engineered AAV3 Capsid, Mol Therapy, 24(6):1042-1049, Jun. 2016.
Bevan et al, Systemic Gene Delivery in Large Species for Targeting Spinal Cord, Brain, and Peripheral Tissues for Pediatric Disorders, Mol Ther. Nov. 2011;19(11):1971-80. doi: 10.1038/mt.2011.157. Epub Aug. 2, 2011.
Messina et al., 2012, Repeat Transduction in the Mouse Lung by Using Adeno-Associated Virus Vectors with Different Serotypes.
Halbert et al., Repeat Transduction in the Mouse Lung by Using Adeno-Associated Virus Vectors with Different Serotypes, J. Virol, 74(3):1524-1532, Feb. 2000.

(56) References Cited

OTHER PUBLICATIONS

Wu, Asokan & Samulski, Adeno-associated Virus Serotypes: Vector Toolkit for Human Gene Therapy, Molecular Therapy, 14(3):316-327, Sep. 2006.
Mao, et al. Angiotensin 1-7 Overexpression Mediated by a Capsid-optimized AAV8 Vector Leads to Significant Growth Inhibition of Hepatocellular Carcinoma In vivo, Int. J. Biol. Sci, Jan. 14, 2018.
Ling et al., Human Hepatocyte Growth Factor Receptor is a Cellular Coreceptor for Adeno-Associated Virus Serotype 3, Human Gene Therapy, 21:1741-1747 (Dec. 2010).
Suhy et al. Safe, Long-term Hepatic Expression of Anti-HCV shRNA in a Nonhuman Primate Model, Mol Ther. Sep. 2012;20(9):1737-49. doi: 10.1038/mt.2012.119. Epub Jun. 26, 2012.
Ling et al, Selective In Vivo Targeting of Human Liver Tumors by Optimized AAV3 Vectors in a Murine Xenograft Model, Hum Gene Ther. Dec. 2014;25(12):1023-34.
Chen et al., Epidemiology of hepatitis B virus infection in the Asia-Pacific region, J Gastroenterol Hepatol. May 2000;15 Suppl:E3-6.
Looker et al., An estimate of the global prevalence and incidence of herpes simplex virus type 2, Bull World Health Organ. Oct. 2008;86(10):805-12, A.
Hamilton et al., Adenoviral-Mediated Gene Transfer to Murine Small Intestine Is More Efficient in Neonates Than Adults, J Pediatr Surg. Feb. 1997;32(2):373-7.
Ellis et al, Virology Journal, Mar. 2013, A survey of ex vivo/in vitro transduction efficiency of mammalian primary cells and cell lines with Nine natural adeno-associated virus (AAV1-9) and one engineered adeno-associated virus serotype, 10:74.
Giles et al, Deamidation of Amino Acids on the Surface of Adeno-Associated Virus Capsids Leads to Charge Heterogeneity and Altered Vector Function, Mol Ther, 26(12), Dec. 2018.
Declaration of Oliver Danos, Ph.D. dated Aug. 14, 2018, submitted in Opposition of EP Patent No. 02795539.2.
Declaration of Prof Asokan, dated Aug. 23, 2018, submitted in Opposition of EP Patent No. 02795539.2.
Declaration of Roberto Calcedo, PhD dated Sep. 24, 2018, submitted in Opposition of EP Patent No. 02795539.2.
Second declaration of Olivier Danos, Ph.D. dated Sep. 25, 2018, submitted in Opposition of EP Patent No. 02795539.2.
Proprietor's Submission pursuant to Rule 116 prior to oral proceedings dated Aug. 24, 2018 submitted in Opposition of EP Patent No. 02795539.2.
Opposer's Submission pursuant to Rule 116 prior to oral proceedings dated Aug. 24, 2018 submitted in Opposition of EP Patent No. 02795539.2.
Proprietor's Further Submission prior to oral proceedings dated Sep. 26, 2018 submitted in Opposition of EP Patent No. 02795539.2.
Opposer's Further Submission prior to oral proceedings dated Oct. 23, 2018 submitted in Opposition of EP Patent No. 02795539.2.
Interlocutory decision in Opposition proceedings issued in related European Patent No. 1453547 on Nov. 30, 2018.
ClinicalTrials.org, "A Gene Therapy Study for Homozygous Familial Hypercholesterolemia", Jan. 2016.
Messina et al., Adeno-associated viral vectors based on serotype 3b use components of the fibroblast growth factor receptor signaling complex for efficient transduction. Hum Gene Ther. Oct. 2012;23(10):1031-42. Epub Aug. 27, 2012.
Notice of Opposition and Opponent's Brief in European Patent No. 2359869, dated Sep. 26, 2019.
Extended Search Report and Search Opinion dated Apr. 24, 2019 in European Patent Application No. 18212719.1.

\* cited by examiner

FIG. 1A

```
cagagaggga gtggccaact ccatcactag gggtagcgcg aagcgcctcc cacgctgccg      60
cgtcagcgct gacgtaaatt acgtcatagg ggagtggtcc tgtattagct gtcacgtgag     120
tgcttttgcg gcattttgcg acaccacgtg gccatttgag gtatatatgg ccgagtgagc     180

Rep68/78 start
gagcaggatc tccatttga ccgcgaaatt tgaacgagca gcagccatgc cgggcttcta     240
cgagatcgtg atcaaggtgc cgagcgacct ggacgagcac ctgccgggca tttctgactc     300
gtttgtgaac tgggtggccg agaaggaatg ggagctgccc ccggattctg acatggatcg     360
gaatctgatc gagcaggcac ccctgaccgt ggccgagaag ctgcagcgcg acttcctggt     420
ccaatggcgc cgcgtgagta aggccccgga ggccctcttc tttgttcagt tcgagaaggg     480
cgagagctac tttcacctgc acgttctggt cgagaccacg ggggtcaagt ccatggtgct     540
aggccgcttc ctgagtcaga ttcgggaaaa gcttggtcca gaccatctac ccgcggggtc     600
gagccccacc ttgcccaact ggttcgcggt gaccaaagac gcggtaatgg cgccggcggg     660
ggggaacaag gtggtggacg agtgctacat ccccaactac ctcctgccca agactcagcc     720
cgagctgcag tgggcgtgga ctaacatgga ggagtatata agcgcgtgct tgaacctggc     780
cgagcgcaaa cggctcgtgg cgcagcacct gacccacgtc agccagacgc aggagcagaa     840
caaggagaat ctgaacccca attctgacgc gcccgtgatc aggtcaaaaa cctccgcgcg     900

Rep40/52 start
ctatatggag ctggtcgggt ggctggtgga ccggggcatc acctccgaga agcagtggat     960
ccaggaggac caggcctcgt acatctcctt caacgccgcc tccaactcgc ggtcccagat    1020
caaggccgcg ctggacaatg ccggcaagat catggcgctg accaaatccg cgcccgacta    1080
cctggtgggg ccctcgctgc cgcggacat tacccagaac cgcatctacc gcatcctcgc    1140
tctcaacggc tacgaccctg cctacgccgg ctccgtcttt ctggctgggc tcagaaaaa    1200 gttcgggaaa cgcaacacca tctggctgtt tggacccgcc accaccggca agaccaacat    1260
tgcggaagcc atcgcccacg ccgtgccctt ctacggctgc gtcaactgga ccaatgagaa    1320 ctttccttc aatgattgcg tgacaagat ggtgatctgg tgggaggagg gcaagatgac    1380
ggccaaggtc gtggagtccg ccaaggccat tctcggcggc agcaaggtgc gcgtggacca    1440
aaagtgcaag tcgtccgccc agatcgaccc cacccccgtg atcgtcacct ccaacaccaa    1500
```

FIG. 1B

```
catgtgcgcc gtgattgacg ggaacagcac caccttcgag caccagcagc ctctccagga    1560
ccggatgttt aagttcgaac tcacccgccg tctggagcac gactttggca aggtgacaaa    1620
gcaggaagtc aaagagttct tccgctgggc cagtgatcac gtgaccgagg tggcgcatga    1680
gttttacgtc agaaagggcg gagccagcaa aagacccgcc ccgatgacg cggataaaag    1740
cgagcccaag cgggcctgcc cctcagtcgc ggatccatcg acgtcagacg cggaaggagc    1800
tccggtggac tttgccgaca ggtaccaaaa caaatgttct cgtcacgcgg gcatgcttca    1860
gatgctgttt ccctgcaaaa cgtgcgagag aatgaatcag aatttcaaca tttgcttcac    1920
acacggggtc agagactgct cagagtgttt cccggcgtg tcagaatctc aaccggtcgt    1980
cagaaagagg acgtatcgga actctgtgc gattcatcat ctgctgggc gggctcccga    2040
gattgcttgc tcggcctgcg atctggtcaa cgtggacctg gatgactgtg tttctgagca    2100
```
                rep78 stop                    vp1 start
```
ataaatgact taaaccaggt atggctgccg atggttatct tccagattgg ctcgaggaca    2160
acctctctga gggcattcgc gagtggtggg cgctgaaacc tggagcccg aagcccaaag    2220
ccaaccagca aaagcaggac gacggccggg gtctggtgct tcctggctac aagtacctcg    2280
gacccttcaa cggactcgac aaggggagc ccgtcaacgc ggcggacgca gcggccctcg    2340
agcacgacaa ggcctacgac cagcagctgc aggcgggtga caatccgtac ctgcggtata    2400
accacgccga cgccgagttt caggagcgtc tgcaagaaga tacgtctttt ggggcaacc    2460
tcgggcgagc agtcttccag gccaagaagc gggttctcga cctctcggt ctggttgagg    2520
aaggcgctaa gacggctcct ggaaagaaga gaccggtaga gccatcaccc cagcgttctc    2580
```
                 vp2 start
```
cagactcctc tacgggcatc ggcaagaaag ccaacagcc cgccagaaaa agactcaatt    2640
ttggtcagac tggcgactca gagtcagttc cagaccctca acctctcgga gaacctccag    2700
cagcgccctc tggtgtggga cctaatacaa tggctgcagg cggtggcgca ccaatggcag    2760
```
                                    vp3 start
```
acaataacga aggcgccgac ggagtgggta gttcctcggg aaattggcat tgcgattcca    2820
catggctggg cgacagagtc atcaccacca gcacccgaac ctgggcctg cccacctaca    2880
acaaccacct ctacaagcaa atctccaacg ggacatcggg aggagccacc aacgacaaca    2940
```

FIG. 1C

```
cctacttcgg ctacagcacc ccctgggggt attttgactt taacagattc cactgccact   3000
tttcaccacg tgactggcag cgactcatca acaacaactg gggattccgg cccaagagac   3060
tcagcttcaa gctcttcaac atccaggtca aggaggtcac gcagaatgaa ggcaccaaga   3120
ccatcgccaa taacctcacc agcaccatcc aggtgtttac ggactcggag taccagctgc   3180
cgtacgttct cggctctgcc caccagggct gcctgcctcc gttcccggcg gacgtgttca   3240
tgattcccca gtacggctac ctaacactca acaacggtag tcaggccgtg ggacgctcct   3300
ccttctactg cctggaatac tttccttcgc agatgctgag aaccggcaac aacttccagt   3360
ttacttacac cttcgaggac gtgccttttc acagcagcta cgcccacagc cagagcttgg   3420
accggctgat gaatcctctg attgaccagt acctgtacta cttgtctcgg actcaaacaa   3480
caggaggcac ggcaaatacg cagactctgg gcttcagcca aggtgggcct aatacaatgg   3540
ccaatcaggc aaagaactgg ctgccaggac cctgttaccg ccaacaacgc gtctcaacga   3600
caaccgggca aaacaacaat agcaactttg cctggactgc tgggaccaaa taccatctga   3660
atggaagaaa ttcattggct aatcctggca tcgctatggc aacacacaaa gacgacgagg   3720
agcgtttttt tcccagtaac gggatcctga ttttggcaa acaaaatgct gcagagaca    3780
atgcggatta cagcgatgtc atgctcacca gcgaggaaga aatcaaaacc actaaccctg   3840
tggctacaga ggaatacggt atcgtggcag ataacttgca gcagcaaaac acggctcctc   3900
aaattggaac tgtcaacagc cagggggcct acccggtat ggtctggcag aaccgggacg   3960
tgtacctgca gggtcccatc tgggccaaga ttcctcacac ggacggcaac ttccacccgt   4020
ctccgctgat gggcggcttt ggcctgaaac atcctccgcc tcagatcctg atcaagaaca   4080
cgcctgtacc tgcggatcct ccgaccacct tcaaccagtc aaagctgaac tctttcatca   4140
cgcaatacag caccggacag gtcagcgtgg aaattgaatg ggagctgcag aaggaaaaca   4200
gcaagcgctg gaaccccgag atccagtaca cctccaacta ctacaaatct acaagtgtgg   4260
actttgctgt taatacagaa ggcgtgtact ctgaaccccg ccccattggc acccgttacc   4320
                        vp1-3 stop            polyA
tcacccgtaa tctgtaattg cctgttaatc aataaaccgg ttgattcgtt tcagttgaac   4380
tttggtctct gcg                                                     4393
```

Fig. 2A

```
          1                                                          50
AAV_2     MAADGYLPDW LEDTLSEGIR QWWKLKPGPP PPKPAERHKD DSRGLVLPGY
AAV_7     MAADGYLPDW LEDNLSEGIR EWWDLKPGAP KPKANQQKQD NGRGLVLPGY
AAV_8     MAADGYLPDW LEDNLSEGIR EWWALKPGAP KPKANQQKQD DGRGLVLPGY
AAV_1     MAADGYLPDW LEDNLSEGIR EWWDLKPGAP KPKANQQKQD DGRGLVLPGY
AAV_3     MAADGYLPDW LEDNLSEGIR EWWALKPGVP QPKANQQHQD NRRGLVLPGY
AAV_9     MAADGYLPDW LEDNLSEGIR EWWDLKPGAP KPKANQQKQD DGRGLVLPGY 51                                                         100
AAV_2     KYLGPFNGLD KGEPVNEADA AALEHDKAYD RQLDSGDNPY LKYNHADAEF
AAV_7     KYLGPFNGLD KGEPVNAADA AALEHDKAYD QQLKAGDNPY LRYNHADAEF
AAV_8     KYLGPFNGLD KGEPVNAADA AALEHDKAYD QQLQAGDNPY LRYNHADAEF
AAV_1     KYLGPFNGLD KGEPVNAADA AALEHDKAYD QQLKAGDNPY LRYNHADAEF
AAV_3     KYLGPGNGLD KGEPVNEADA AALEHDKAYD QQLKAGDNPY LKYNHADAEF
AAV_9     KYLGPFNGLD KGEPVNAADA AALEHDKAYD QQLKAGDNPY LRYNHADAEF 101                                                        150
AAV_2     QERLKEDTSF GGNLGRAVFQ AKKRVLEPLG LVEEPVKTAP GKKRPVEHSP
AAV_7     QERLQEDTSF GGNLGRAVFQ AKKRVLEPLG LVEEGAKTAP AKKRPVEPSP
AAV_8     QERLQEDTSF GGNLGRAVFQ AKKRVLEPLG LVEEGAKTAP GKKRPVEPSP
AAV_1     QERLQEDTSF GGNLGRAVFQ AKKRVLEPLG LVEEGAKTAP GKKRPVEQSP
AAV_3     QERLQEDTSF GGNLGRAVFQ AKKRILEPLG LVEEAAKTAP GKKGAVDQSP
AAV_9     QERLQEDTSF GGNLGRAVFQ AKKRVLEPLG LVEEGAKTAP GKKRPVEQSP 151                                                        200
AAV_2     .VEPDSSSGT GKAGQQPARK RLNFGQTGDA DSVPDPQPLG QPPAAPSGLG
AAV_7     QRSPDSSTGI GKKGQQPARK RLNFGQTGDS ESVPDPQPLG EPPAAPSSVG
AAV_8     QRSPDSSTGI GKKGQQPARK RLNFGQTGDS ESVPDPQPLG EPPAAPSGVG
AAV_1     .QEPDSSSGI GKTGQQPAKK RLNFGQTGDS ESVPDPQPLG EPPATPAAVG
AAV_3     .QEPDSSSGV GKSGKQPARK RLNFGQTGDS ESVPDPQPLG EPPAAPTSLG
AAV_9     QE.PDSSSGI GKSGQQPAKK RLNFGQTGDS ESVPDPQPLG EPPEAPSGLG 201                                                        250
AAV_2     TNTMATGSGA PMADNNEGAD GVGNSSGNWH CDSTWMGDRV ITTSTRTWAL
AAV_7     SGTVAAGGGA PMADNNEGAD GVGNASGNWH CDSTWLGDRV ITTSTRTWAL
AAV_8     PNTMAAGGGA PMADNNEGAD GVGSSSGNWH CDSTWLGDRV ITTSTRTWAL
AAV_1     PTTMASGGGA PMADNNEGAD GVGNASGNWH CDSTWLGDRV ITTSTRTWAL
AAV_3     SNTMASGGGA PMADNNEGAD GVGNSSGNWH CDSQWLGDRV ITTSTRTWAL
AAV_9     PNTMASGGGA PMADNNEGAD GVGNSSGNWH CDSTWLGDRV ITTSTRTWAL 251                                                        300
AAV_2     PTYNNHLYKQ ISSQS--GAS NDNHYFGYST PWGYFDFNRF HCHFSPRDWQ
AAV_7     PTYNNHLYKQ ISSETA-GST NDNTYFGYST PWGYFDFNRF HCHFSPRDWQ
AAV_8     PTYNNHLYKQ ISNGTSGGAT NDNTYFGYST PWGYFDFNRF HCHFSPRDWQ
AAV_1     PTYNNHLYKQ ISSAST.GAS NDNHYFGYST PWGYFDFNRF HCHFSPRDWQ
AAV_3     PTYNNHLYKQ ISSQS..GAS NDNHYFGYST PWGYFDFNRF HCHFSPRDWQ
AAV_9     PTYNNHLYKQ ISNGTSGGST NDNTYFGYST PWGYFDFNRF HCHFSPRDWQ
```

Fig. 2B

```
       301                                                     350
AAV_2  RLINNNWGFR PKRLNFKLFN IQVKEVTQND GTTTIANNLT STVQVFTDSE
AAV_7  RLINNNWGFR PKKLRFKLFN IQVKEVTTND GVTTIANNLT STIQVFSDSE
AAV_8  RLINNNWGFR PKRLSFKLFN IQVKEVTQNE GTKTIANNLT STIQVFTDSE
AAV_1  RLINNNWGFR PKRLNFKLFN IQVKEVTTND GVTTIANNLT STVQVFSDSE
AAV_3  RLINNNWGFR PKKLSFKLFN IQVRGVTQND GTTTIANNLT STVQVFTDSE
AAV_9  RLINNNWGFR PKRLNFKLFN IQVKEVTTNE GTKTIANNLT STVQVFTDSE 351                                                     400
AAV_2  YQLPYVLGSA HQGCLPPFPA DVFMVPQYGY LTLNNGSQAV GRSSFYCLEY
AAV_7  YQLPYVLGSA HQGCLPPFPA DVFMIPQYGY LTLNNGSQSV GRSSFYCLEY
AAV_8  YQLPYVLGSA HQGCLPPFPA DVFMIPQYGY LTLNNGSQAV GRSSFYCLEY
AAV_1  YQLPYVLGSA HQGCLPPFPA DVFMIPQYGY LTLNNGSQAV GRSSFYCLEY
AAV_3  YQLPYVLGSA HQGCLPPFPA DVFMVPQYGY LTLNNGSQAV GRSSFYCLEY
AAV_9  YQLPYVLGSA HQGCLPPFPA DVFMVPQYGY LTLNNGSQAL GRSSFYCLEY 401                                                     450
AAV_2  FPSQMLRTGN NFTFSYTFED VPFHSSYAHS QSLDRLMNPL IDQYLYYLSR
AAV_7  FPSQMLRTGN NFEFSYSFED VPFHSSYAHS QSLDRLMNPL IDQYLYYLAR
AAV_8  FPSQMLRTGN NFQFTYTFED VPFHSSYAHS QSLDRLMNPL IDQYLYYLSR
AAV_1  FPSQMLRTGN NFTFSYTFEE VPFHSSYAHS QSLDRLMNPL IDQYLYYLNR
AAV_3  FPSQMLRTGN NFQFSYTFED VPFHSSYAHS QSLDRLMNPL IDQYLYYLNR
AAV_9  FPSQMLRTGN NFQFSYTFED VPFHSSYAHS QSLDRLMNPL IDQYLYYLVR 451                                                     500
AAV_2  TNTPSG.TTT QSRLQFSQAG ASDIRDQS RNWLPGPCYRQQ RVSKTSADNN
AAV_7  TQSNPGGTAG NRELQFYQGG PSTMAEQA KNWLPGPCFRQQ RVSKTLDQNN
AAV_8  TQTTGG.TAN TQTLGFSQGG PNTMANQA KNWLPGPCYRQQ RVSTTTGQNN
AAV_1  TQ.NQSGSAQ NKDLLFSRGS PAGMSVQP KNWLPGPCYRQQ RVSKTKTDNN
AAV_3  TQGTTSGTTN QSRLLFSQAG PQSMSLQA RNWLPGPCYRQQ RLSKTANDNN
AAV_9  TQTTG..TGG TQTLAFSQAG PSSMANQA RNWVPGPCYRQQ RVSTTTNQNN 501                                                     550
AAV_2  NSEYSWTGAT KYHLNGRDSL VNPGPAMASH KDDEEKFFPQ SGVLIFGKQG
AAV_7  NSNFAWTGAT KYHLNGRNSL VNPGVAMATH KDDEDRFFPS SGVLIFGKTG
AAV_8  NSNFAWTAGT KYHLNGRNSL ANPGIAMATH KDDEERFFPS NGILIFGKQN
AAV_1  NSNFTWTGAS KYNLNGRESI INPGTAMASH KDDEDKFFPM SGVMIFGKES
AAV_3  NSNFPWTAAS KYHLNGRDSL VNPGPAMASH KDDEEKFFPM HGNLIFGKEG
AAV_9  NSNFAWTGAA KFKLNGRDSL MNPGVAMASH KDDEDRFFPS SGVLIFGKQG 551                                                     600
AAV_2  SEKTNVDIEK VMITDEEEIR T TNPVATEQY GSVSTNLQRG NRQAATADVN
AAV_7  ATNKTT-LEN VLMTNEEEIR P TNPVATEEY GIVSSNLQAA NTAAQTQVVN
AAV_8  AARDNADYSD VMLTSEEEIK T TNPVATEEY GIVADNLQQQ NTAPQIGTVN
AAV_1  AGASNTALDN VMITDEEEIK A TNPVATERF GTVAVNFQSS STDPATGDVH
AAV_3  TTASNAELDN VMITDEEEIR T TNPVATEQY GTVANNLQSS NTAPTTGTVN
AAV_9  AGNDGVDYSQ VLITDEEEIK A TNPVATEEY GAVAINNQAA NTQAQTGLVH
```

Fig. 2C

```
        601                                                    650
AAV_2   TQGVLPGMVW QDRDVYLQGP IWAKIPHTDG HFHPSPLMGG FGLKHPPPQI
AAV_7   NQGALPGMVW QNRDVYLQGP IWAKIPHTDG NFHPSPLMGG FGLKHPPPQI
AAV_8   SQGALPGMVW QNRDVYLQGP IWAKIPHTDG NFHPSPLMGG FGLKHPPPQI
AAV_1   AMGALPGMVW QDRDVYLQGP IWAKIPHTDG HFHPSPLMGG FGLKNPPPQI
AAV_3   HQGALPGMVW QDRDVYLQGP IWAKIPHTDG HFHPSPLMGG FGLKHPPPQI
AAV_9   NQGVIPGMVW QNRDVYLQGP IWAKIPHTDG NFHPSPLMGG FGLKHPPPQI 651                                                    700
AAV_2   LIKNTPVPA NPSTTFSAAKF ASFITQYSTG QVSVEIEWEL QKENSKRWNP
AAV_7   LIKNTPVPA NPPEVFTPAKF ASFITQYSTG QVSVEIEWEL QKENSKRWNP
AAV_8   LIKNTPVPA DPPTTFNQSKL NSFITQYSTG QVSVEIEWEL QKENSKRWNP
AAV_1   LIKNTPVPA NPPAEFSATKF ASFITQYSTG QVSVEIEWEL QKENSKRWNP
AAV_3   MIKNTPVPA NPPTTFSPAKF ASFITQYSTG QVSVEIEWEL QKENSKRWNP
AAV_9   LIKNTPVPA DPPLTFNQAKL NSFITQYSTG QVSVEIEWEL QKENSKRWNP 701                             739
AAV_2   EIQYTSNYNK SVNVDFTVDT NGVYSEPRPI GTRYLTRNL
AAV_7   EIQYTSNFEK QTGVDFAVDS QGVYSEPRPI GTRYLTRNL
AAV_8   EIQYTSNYYK STSVDFAVNT EGVYSEPRPI GTRYLTRNL
AAV_1   EVQYTSNYAK SANVDFTVDN NGLYTEPRPI GTRYLTRPL
AAV_3   EIQYTSNYNK SVNVDFTVDT NGVYSEPRPI GTRYLTRNL
AAV_9   EIQYTSNYYK STNVDFAVNT EGVYSEPRPI GTRYLTRNL
```

Fig. 3A

| | | | | | | | | | | | | | | |
|---|---|---|---|---|---|---|---|---|---|---|---|---|---|---|

Met Pro Gly Phe Tyr Glu Ile Val Ile Lys Val Pro Ser Asp Leu Asp
1   　　　　　　5　　　　　　　　10　　　　　　　　15

Glu His Leu Pro Gly Ile Ser Asp Ser Phe Val Asn Trp Val Ala Glu
　　　　　　20　　　　　　　　25　　　　　　　　30

Lys Glu Trp Glu Leu Pro Pro Asp Ser Asp Met Asp Arg Asn Leu Ile
　　　　　35　　　　　　　　40　　　　　　　　45

Glu Gln Ala Pro Leu Thr Val Ala Glu Lys Leu Gln Arg Asp Phe Leu
　　　50　　　　　　　　55　　　　　　　　60

Val Gln Trp Arg Arg Val Ser Lys Ala Pro Glu Ala Leu Phe Phe Val
65　　　　　　　　70　　　　　　　　75　　　　　　　　80

Gln Phe Glu Lys Gly Glu Ser Tyr Phe His Leu His Val Leu Val Glu
　　　　　　85　　　　　　　　90　　　　　　　　95

Thr Thr Gly Val Lys Ser Met Val Leu Gly Arg Phe Leu Ser Gln Ile
　　　　　　100　　　　　　　105　　　　　　　110

Arg Glu Lys Leu Gly Pro Asp His Leu Pro Ala Gly Ser Ser Pro Thr
　　　　　115　　　　　　　　120　　　　　　　125

Leu Pro Asn Trp Phe Ala Val Thr Lys Asp Ala Val Met Ala Pro Ala
　　　130　　　　　　　　135　　　　　　　　140

Gly Gly Asn Lys Val Val Asp Glu Cys Tyr Ile Pro Asn Tyr Leu Leu
145　　　　　　　　150　　　　　　　　155　　　　　　　　160

Pro Lys Thr Gln Pro Glu Leu Gln Trp Ala Trp Thr Asn Met Glu Glu
　　　　　　　165　　　　　　　　170　　　　　　　　175

Tyr Ile Ser Ala Cys Leu Asn Leu Ala Glu Arg Lys Arg Leu Val Ala
　　　　　　180　　　　　　　　185　　　　　　　　190

Gln His Leu Thr His Val Ser Gln Thr Gln Glu Gln Asn Lys Glu Asn
　　　　　195　　　　　　　　200　　　　　　　　205

Leu Asn Pro Asn Ser Asp Ala Pro Val Ile Arg Ser Lys Thr Ser Ala
　　　210　　　　　　　　215　　　　　　　　220

Fig. 3B

Arg Tyr Met Glu Leu Val Gly Trp Leu Val Asp Arg Gly Ile Thr Ser
225                 230                 235                 240

Glu Lys Gln Trp Ile Gln Glu Asp Gln Ala Ser Tyr Ile Ser Phe Asn
            245                 250                 255

Ala Ala Ser Asn Ser Arg Ser Gln Ile Lys Ala Ala Leu Asp Asn Ala
            260                 265                 270

Gly Lys Ile Met Ala Leu Thr Lys Ser Ala Pro Asp Tyr Leu Val Gly
            275                 280                 285

Pro Ser Leu Pro Ala Asp Ile Thr Gln Asn Arg Ile Tyr Arg Ile Leu
290                 295                 300

Ala Leu Asn Gly Tyr Asp Pro Ala Tyr Ala Gly Ser Val Phe Leu Gly
305                 310                 315                 320

Trp Ala Gln Lys Lys Phe Gly Lys Arg Asn Thr Ile Trp Leu Phe Gly
            325                 330                 335

Pro Ala Thr Thr Gly Lys Thr Asn Ile Ala Glu Ala Ile Ala His Ala
            340                 345                 350

Val Pro Phe Tyr Gly Cys Val Asn Trp Thr Asn Glu Asn Phe Pro Phe
            355                 360                 365

Asn Asp Cys Val Asp Lys Met Val Ile Trp Trp Glu Glu Gly Lys Met
            370                 375                 380

Thr Ala Lys Val Val Glu Ser Ala Lys Ala Ile Leu Gly Gly Ser Lys
385                 390                 395                 400

Val Arg Val Asp Gln Lys Cys Lys Ser Ser Ala Gln Ile Asp Pro Thr
            405                 410                 415

Pro Val Ile Val Thr Ser Asn Thr Asn Met Cys Ala Val Ile Asp Gly
            420                 425                 430

Asn Ser Thr Thr Phe Glu His Gln Gln Pro Leu Gln Asp Arg Met Phe
            435                 440                 445

Fig. 3C

Lys Phe Glu Leu Thr Arg Arg Leu Glu His Asp Phe Gly Lys Val Thr
    450             455             460

Lys Gln Glu Val Lys Glu Phe Phe Arg Trp Ala Ser Asp His Val Thr
465         470             475                 480

Glu Val Ala His Glu Phe Tyr Val Arg Lys Gly Gly Ala Ser Lys Arg
            485             490                 495

Pro Ala Pro Asp Asp Ala Asp Lys Ser Glu Pro Lys Arg Ala Cys Pro
            500             505             510

Ser Val Ala Asp Pro Ser Thr Ser Asp Ala Glu Gly Ala Pro Val Asp
        515             520             525

Phe Ala Asp Arg Tyr Gln Asn Lys Cys Ser Arg His Ala Gly Met Leu
    530             535             540

Gln Met Leu Phe Pro Cys Lys Thr Cys Glu Arg Met Asn Gln Asn Phe
545             550             555             560

Asn Ile Cys Phe Thr His Gly Val Arg Asp Cys Ser Glu Cys Phe Pro
            565             570             575

Gly Val Ser Glu Ser Gln Pro Val Val Arg Lys Arg Thr Tyr Arg Lys
            580             585             590

Leu Cys Ala Ile His His Leu Leu Gly Arg Ala Pro Glu Ile Ala Cys
        595             600             605

Ser Ala Cys Asp Leu Val Asn Val Asp Leu Asp Asp Cys Val Ser Glu
    610             615             620

Gln
625

SEQUENCE LISTING

```
<160> NUMBER OF SEQ ID NOS: 8

<210> SEQ ID NO 1
<211> LENGTH: 4393
<212> TYPE: DNA
<213> ORGANISM: adeno-associated virus serotype 8

<400> SEQUENCE: 1
cagagaggga gtggccaact ccatcactag gggtagcgcg aagcgcctcc cacgctgccg      60
cgtcagcgct gacgtaaatt acgtcatagg ggagtggtcc tgtattagct gtcacgtgag     120
tgcttttgcg gcattttgcg acaccacgtg gccatttgag gtatatatgg ccgagtgagc     180
gagcaggatc tccattttga ccgcgaaatt tgaacgagca gcagccatgc cgggcttcta     240
cgagatcgtg atcaaggtgc cgagcgacct ggacgagcac ctgccgggca tttctgactc     300
gtttgtgaac tgggtggccg agaaggaatg ggagctgccc ccggattctg acatggatcg     360
gaatctgatc gagcaggcac ccctgaccgt ggccgagaag ctgcagcgcg acttcctggt     420
ccaatggcgc cgcgtgagta aggccccgga ggccctcttc tttgttcagt tcgagaaggg     480
cgagagctac tttcacctgc acgttctggt cgagaccacg ggggtcaagt ccatggtgct     540
aggccgcttc ctgagtcaga ttcgggaaaa gcttggtcca gaccatctac ccgcggggtc     600
gagccccacc ttgcccaact ggttcgcggt gaccaaagac gcggtaatgg cgccggcggg     660
ggggaacaag gtggtggacg agtgctacat ccccaactac ctcctgccca agactcagcc     720
cgagctgcag tgggcgtgga ctaacatgga ggagtatata agcgcgtgct tgaacctggc     780
cgagcgcaaa cggctcgtgg cgcagcacct gacccacgtc agccagacgc aggagcagaa     840
caaggagaat ctgaacccca attctgacgc gcccgtgatc aggtcaaaaa cctccgcgcg     900
ctatatggag ctggtcgggt ggctggtgga ccggggcatc acctccgaga agcagtggat     960
ccaggaggac caggcctcgt acatctcctt caacgccgcc tccaactcgc ggtcccagat    1020
caaggccgcg ctgacaatgc ccggcaagat catggcgctg accaaatccg cgcccgacta    1080
cctggtgggg cctcgctgc ccgcggacat tacccagaac cgcatctacc gcatcctcgc    1140
tctcaacggc tacgaccctg cctacgccgg ctccgtcttt ctcggctggg ctcagaaaaa    1200
```

```
gttcgggaaa cgcaacacca tctggctgtt tggacccgcc accaccggca agaccaacat   1260
tgcggaagcc atcgcccacg ccgtgccctt ctacggctgc gtcaactgga ccaatgagaa   1320
ctttcccttc aatgattgcg tcgacaagat ggtgatctgg tgggaggagg gcaagatgac   1380
ggccaaggtc gtggagtccg ccaaggccat tctcggcggc agcaaggtgc gcgtggacca   1440
aaagtgcaag tcgtccgccc agatcgaccc caccccgtg atcgtcacct ccaacaccaa    1500
catgtgcgcc gtgattgacg ggaacagcac caccttcgag caccagcagc ctctccagga   1560
ccggatgttt aagttcgaac tcacccgccg tctggagcac gactttggca aggtgacaaa   1620
gcaggaagtc aaagagttct tccgctgggc cagtgatcac gtgaccgagg tggcgcatga   1680
gttttacgtc agaaagggcg gagccagcaa agacccgcc cccgatgacg cggataaaag    1740
cgagcccaag cgggcctgcc cctcagtcgc ggatccatcg acgtcagacg cggaaggagc   1800
tccggtggac tttgccgaca ggtaccaaaa caaatgttct cgtcacgcgg gcatgcttca   1860
gatgctgttt ccctgcaaaa cgtgcgagag aatgaatcag aatttcaaca tttgcttcac   1920
acacggggtc agagactgct cagagtgttt ccccggcgtg tcagaatctc aaccggtcgt   1980
cagaaagagg acgtatcgga aactctgtgc gattcatcat ctgctggggc gggctcccga   2040
gattgcttgc tcggcctgcg atctggtcaa cgtggacctg gatgactgtg tttctgagca   2100
ataaatgact taaaccaggt atggctgccg atggttatct tccagattgg ctcgaggaca   2160
acctctctga gggcattcgc gagtggtggg cgctgaaacc tggagccccg aagcccaaag   2220
ccaaccagca aaagcaggac gacggccggg gtctggtgct tcctggctac aagtacctcg   2280
gacccttcaa cggactcgac aagggggagc ccgtcaacgc ggcggacgca gcggccctcg   2340
agcacgacaa ggcctacgac cagcagctgc aggcgggtga caatccgtac ctgcggtata   2400
accacgccga cgccgagttt caggagcgtc tgcaagaaga tacgtctttt gggggcaacc   2460
tcgggcgagc agtcttccag gccaagaagc gggttctcga acctctcggt ctggttgagg   2520
aaggcgctaa gacggctcct ggaaagaaga gaccggtaga gccatcaccc cagcgttctc   2580
cagactcctc tacgggcatc ggcaagaaag gccaacagcc cgccagaaaa agactcaatt   2640
ttggtcagac tggcgactca gagtcagttc cagaccctca acctctcgga gaacctccag   2700
cagcgccctc tggtgtggga cctaatacaa tggctgcagg cggtggcgca ccaatggcag   2760
acaataacga aggcgccgac ggagtgggta gttcctcggg aaattggcat tgcgattcca   2820
catggctggg cgacagagtc atcaccacca gcacccgaac ctgggccctg cccacctaca   2880
acaaccacct ctacaagcaa atctccaacg ggacatcggg aggagccacc aacgacaaca   2940
cctacttcgg ctacagcacc ccctgggggt attttgactt taacagattc cactgccact   3000
tttcaccacg tgactggcag cgactcatca acaacaactg gggattccgg cccaagagac   3060
tcagcttcaa gctcttcaac atccaggtca aggaggtcac gcagaatgaa ggcaccaaga   3120
ccatcgccaa taacctcacc agcaccatcc aggtgtttac ggactcggag taccagctgc   3180
cgtacgttct cggctctgcc accagggct gcctgcctcc gttcccggcg acgtgttca     3240 tgattcccca gtacggctac ctaacactca acaacggtag tcaggccgtg gacgctcct    3300 ccttctactg cctggaatac tttccttcgc agatgctgag aaccggcaac aacttccagt   3360
ttacttacac cttcgaggac gtgcctttcc acagcagcta cgcccacagc cagagcttgg   3420
accggctgat gaatcctctg attgaccagt acctgtacta cttgtctcgg actcaaacaa   3480
caggaggcac ggcaaatacg cagactctgg gcttcagcca aggtgggcct aatacaatgg   3540
```

-continued

```
ccaatcaggc aaagaactgg ctgccaggac cctgttaccg ccaacaacgc gtctcaacga    3600
caaccgggca aaacaacaat agcaactttg cctggactgc tgggaccaaa taccatctga    3660
atggaagaaa ttcattggct aatcctggca tcgctatggc aacacacaaa gacgacgagg    3720
agcgtttttt tcccagtaac gggatcctga tttttggcaa acaaaatgct gccagagaca    3780
atgcggatta cagcgatgtc atgctcacca gcgaggaaga aatcaaaacc actaaccctg    3840
tggctacaga ggaatacggt atcgtggcag ataacttgca gcagcaaaac acggctcctc    3900
aaattggaac tgtcaacagc cagggggcct acccggtat ggtctggcag aaccgggacg    3960
tgtacctgca gggtcccatc tgggccaaga ttcctcacac ggacggcaac ttccaccgt    4020 ctccgctgat gggcggcttt ggcctgaaac atcctccgcc tcagatcctg atcaagaaca    4080
cgcctgtacc tgcggatcct ccgaccacct caaccagtc aaagctgaac tctttcatca    4140
cgcaatacag caccggacag gtcagcgtgg aaattgaatg ggagctgcag aaggaaaaca    4200
gcaagcgctg gaaccccgag atccagtaca cctccaacta ctacaaatct acaagtgtgg    4260
actttgctgt taatacagaa ggcgtgtact ctgaaccccg ccccattggc acccgttacc    4320
tcacccgtaa tctgtaattg cctgttaatc aataaaccgg ttgattcgtt tcagttgaac    4380
tttggtctct gcg                                                      4393
```

<210> SEQ ID NO 2
<211> LENGTH: 738
<212> TYPE: PRT
<213> ORGANISM: adeno-associated virus serotype 8

<400> SEQUENCE: 2

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ala Gly Gly
        195                 200                 205

Gly Ala Pro Met Ala Asp Asn Asn Glu Gly Ala Asp Gly Val Gly Ser
    210                 215                 220
```

-continued

```
Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
            245                 250                 255

Leu Tyr Lys Gln Ile Ser Asn Gly Thr Ser Gly Gly Ala Thr Asn Asp
        260                 265                 270

Asn Thr Tyr Phe Gly Tyr Ser Thr Pro Trp Gly Tyr Phe Asp Phe Asn
    275                 280                 285

Arg Phe His Cys His Phe Ser Pro Arg Asp Trp Gln Arg Leu Ile Asn
        290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Gln Phe Thr Tyr
                405                 410                 415

Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Thr Thr Gly Gly Thr Ala Asn Thr Gln Thr Leu Gly
    450                 455                 460

Phe Ser Gln Gly Gly Pro Asn Thr Met Ala Asn Gln Ala Lys Asn Trp
465                 470                 475                 480

Leu Pro Gly Pro Cys Tyr Arg Gln Gln Arg Val Ser Thr Thr Thr Gly
                485                 490                 495

Gln Asn Asn Asn Ser Asn Phe Ala Trp Thr Ala Gly Thr Lys Tyr His
            500                 505                 510

Leu Asn Gly Arg Asn Ser Leu Ala Asn Pro Gly Ile Ala Met Ala Thr
        515                 520                 525

His Lys Asp Asp Glu Glu Arg Phe Phe Pro Ser Asn Gly Ile Leu Ile
    530                 535                 540

Phe Gly Lys Gln Asn Ala Ala Arg Asp Asn Ala Asp Tyr Ser Asp Val
545                 550                 555                 560

Met Leu Thr Ser Glu Glu Glu Ile Lys Thr Thr Asn Pro Val Ala Thr
                565                 570                 575

Glu Glu Tyr Gly Ile Val Ala Asp Asn Leu Gln Gln Asn Thr Ala
            580                 585                 590

Pro Gln Ile Gly Thr Val Asn Ser Gln Gly Ala Leu Pro Gly Met Val
        595                 600                 605

Trp Gln Asn Arg Asp Val Tyr Leu Gln Gly Pro Ile Trp Ala Lys Ile
    610                 615                 620

Pro His Thr Asp Gly Asn Phe His Pro Ser Pro Leu Met Gly Gly Phe
625                 630                 635                 640
```

```
Gly Leu Lys His Pro Pro Gln Ile Leu Ile Lys Asn Thr Pro Val
            645             650                 655
Pro Ala Asp Pro Pro Thr Thr Phe Asn Gln Ser Lys Leu Asn Ser Phe
            660             665             670
Ile Thr Gln Tyr Ser Thr Gly Gln Val Ser Val Glu Ile Glu Trp Glu
        675             680             685
Leu Gln Lys Glu Asn Ser Lys Arg Trp Asn Pro Glu Ile Gln Tyr Thr
    690             695             700
Ser Asn Tyr Tyr Lys Ser Thr Ser Val Asp Phe Ala Val Asn Thr Glu
705             710             715                 720
Gly Val Tyr Ser Glu Pro Arg Pro Ile Gly Thr Arg Tyr Leu Thr Arg
            725             730             735
Asn Leu

<210> SEQ ID NO 3
<211> LENGTH: 625
<212> TYPE: PRT
<213> ORGANISM: adeno-associated virus serotype 8

<400> SEQUENCE: 3

Met Pro Gly Phe Tyr Glu Ile Val Ile Lys Val Pro Ser Asp Leu Asp
1               5                   10                  15
Glu His Leu Pro Gly Ile Ser Asp Ser Phe Val Asn Trp Val Ala Glu
            20                  25                  30
Lys Glu Trp Glu Leu Pro Pro Asp Ser Asp Met Asp Arg Asn Leu Ile
        35                  40                  45
Glu Gln Ala Pro Leu Thr Val Ala Glu Lys Leu Gln Arg Asp Phe Leu
    50                  55                  60
Val Gln Trp Arg Arg Val Ser Lys Ala Pro Glu Ala Leu Phe Phe Val
65                  70                  75                  80
Gln Phe Glu Lys Gly Glu Ser Tyr Phe His Leu His Val Leu Val Glu
                85                  90                  95
Thr Thr Gly Val Lys Ser Met Val Leu Gly Arg Phe Leu Ser Gln Ile
            100                 105                 110
Arg Glu Lys Leu Gly Pro Asp His Leu Pro Ala Gly Ser Ser Pro Thr
        115                 120                 125
Leu Pro Asn Trp Phe Ala Val Thr Lys Asp Ala Val Met Ala Pro Ala
    130                 135                 140
Gly Gly Asn Lys Val Val Asp Glu Cys Tyr Ile Pro Asn Tyr Leu Leu
145                 150                 155                 160
Pro Lys Thr Gln Pro Glu Leu Gln Trp Ala Trp Thr Asn Met Glu Glu
                165                 170                 175
Tyr Ile Ser Ala Cys Leu Asn Leu Ala Glu Arg Lys Arg Leu Val Ala
            180                 185                 190
Gln His Leu Thr His Val Ser Gln Thr Gln Glu Gln Asn Lys Glu Asn
        195                 200                 205
Leu Asn Pro Asn Ser Asp Ala Pro Val Ile Arg Ser Lys Thr Ser Ala
    210                 215                 220
Arg Tyr Met Glu Leu Val Gly Trp Leu Val Asp Arg Gly Ile Thr Ser
225                 230                 235                 240
Glu Lys Gln Trp Ile Gln Glu Asp Gln Ala Ser Tyr Ile Ser Phe Asn
                245                 250                 255
Ala Ala Ser Asn Ser Arg Ser Gln Ile Lys Ala Ala Leu Asp Asn Ala
            260                 265                 270
```

```
Gly Lys Ile Met Ala Leu Thr Lys Ser Ala Pro Asp Tyr Leu Val Gly
            275                 280                 285

Pro Ser Leu Pro Ala Asp Ile Thr Gln Asn Arg Ile Tyr Arg Ile Leu
        290                 295                 300

Ala Leu Asn Gly Tyr Asp Pro Ala Tyr Ala Gly Ser Val Phe Leu Gly
305                 310                 315                 320

Trp Ala Gln Lys Lys Phe Gly Lys Arg Asn Thr Ile Trp Leu Phe Gly
                325                 330                 335

Pro Ala Thr Thr Gly Lys Thr Asn Ile Ala Glu Ala Ile Ala His Ala
            340                 345                 350

Val Pro Phe Tyr Gly Cys Val Asn Trp Thr Asn Glu Asn Phe Pro Phe
        355                 360                 365

Asn Asp Cys Val Asp Lys Met Val Ile Trp Trp Glu Glu Gly Lys Met
370                 375                 380

Thr Ala Lys Val Val Glu Ser Ala Lys Ala Ile Leu Gly Gly Ser Lys
385                 390                 395                 400

Val Arg Val Asp Gln Lys Cys Lys Ser Ser Ala Gln Ile Asp Pro Thr
                405                 410                 415

Pro Val Ile Val Thr Ser Asn Thr Asn Met Cys Ala Val Ile Asp Gly
            420                 425                 430

Asn Ser Thr Thr Phe Glu His Gln Gln Pro Leu Gln Asp Arg Met Phe
        435                 440                 445

Lys Phe Glu Leu Thr Arg Arg Leu Glu His Asp Phe Gly Lys Val Thr
        450                 455                 460

Lys Gln Glu Val Lys Glu Phe Phe Arg Trp Ala Ser Asp His Val Thr
465                 470                 475                 480

Glu Val Ala His Glu Phe Tyr Val Arg Lys Gly Gly Ala Ser Lys Arg
                485                 490                 495

Pro Ala Pro Asp Asp Ala Asp Lys Ser Glu Pro Lys Arg Ala Cys Pro
            500                 505                 510

Ser Val Ala Asp Pro Ser Thr Ser Asp Ala Glu Gly Ala Pro Val Asp
        515                 520                 525

Phe Ala Asp Arg Tyr Gln Asn Lys Cys Ser Arg His Ala Gly Met Leu
530                 535                 540

Gln Met Leu Phe Pro Cys Lys Thr Cys Glu Arg Met Asn Gln Asn Phe
545                 550                 555                 560

Asn Ile Cys Phe Thr His Gly Val Arg Asp Cys Ser Glu Cys Phe Pro
                565                 570                 575

Gly Val Ser Glu Ser Gln Pro Val Val Arg Lys Arg Thr Tyr Arg Lys
            580                 585                 590

Leu Cys Ala Ile His His Leu Leu Gly Arg Ala Pro Glu Ile Ala Cys
        595                 600                 605

Ser Ala Cys Asp Leu Val Asn Val Asp Leu Asp Asp Cys Val Ser Glu
        610                 615                 620

Gln
625

<210> SEQ ID NO 4
<211> LENGTH: 735
<212> TYPE: PRT
<213> ORGANISM: adeno-associated virus serotype 2

<400> SEQUENCE: 4

Met Ala Ala Asp Gly Tyr Leu Pro Asp Trp Leu Glu Asp Thr Leu Ser
1               5                   10                  15
```

```
Glu Gly Ile Arg Gln Trp Trp Lys Leu Lys Pro Gly Pro Pro Pro
                 20                  25                  30
Lys Pro Ala Glu Arg His Lys Asp Asp Ser Arg Gly Leu Val Leu Pro
             35                  40                  45
Gly Tyr Lys Tyr Leu Gly Pro Phe Asn Gly Leu Asp Lys Gly Glu Pro
 50                  55                  60
Val Asn Glu Ala Asp Ala Ala Leu Glu His Asp Lys Ala Tyr Asp
 65              70                  75                  80
Arg Gln Leu Asp Ser Gly Asp Asn Pro Tyr Leu Lys Tyr Asn His Ala
                 85                  90                  95
Asp Ala Glu Phe Gln Glu Arg Leu Lys Glu Asp Thr Ser Phe Gly Gly
            100                 105                 110
Asn Leu Gly Arg Ala Val Phe Gln Ala Lys Lys Arg Val Leu Glu Pro
            115                 120                 125
Leu Gly Leu Val Glu Glu Pro Val Lys Thr Ala Pro Gly Lys Lys Arg
130                 135                 140
Pro Val Glu His Ser Pro Val Glu Pro Asp Ser Ser Ser Gly Thr Gly
145                 150                 155                 160
Lys Ala Gly Gln Gln Pro Ala Arg Lys Arg Leu Asn Phe Gly Gln Thr
                165                 170                 175
Gly Asp Ala Asp Ser Val Pro Asp Pro Gln Pro Leu Gly Gln Pro Pro
            180                 185                 190
Ala Ala Pro Ser Gly Leu Gly Thr Asn Thr Met Ala Thr Gly Ser Gly
            195                 200                 205
Ala Pro Met Ala Asp Asn Asn Glu Gly Ala Asp Gly Val Gly Asn Ser
            210                 215                 220
Ser Gly Asn Trp His Cys Asp Ser Thr Trp Met Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Ser Gln Ser Gly Ala Ser Asn Asp Asn His Tyr
            260                 265                 270
Phe Gly Tyr Ser Thr Pro Trp Gly Tyr Phe Asp Phe Asn Arg Phe His
            275                 280                 285
Cys His Phe Ser Pro Arg Asp Trp Gln Arg Leu Ile Asn Asn Asn Trp
290                 295                 300
Gly Phe Arg Pro Lys Arg Leu Asn Phe Lys Leu Phe Asn Ile Gln Val
305                 310                 315                 320
Lys Glu Val Thr Gln Asn Asp Gly Thr Thr Thr Ile Ala Asn Asn Leu
                325                 330                 335
Thr Ser Thr Val Gln Val Phe Thr Asp Ser Glu Tyr Gln Leu Pro Tyr
            340                 345                 350
Val Leu Gly Ser Ala His Gln Gly Cys Leu Pro Pro Phe Pro Ala Asp
            355                 360                 365
Val Phe Met Val Pro Gln Tyr Gly Tyr Leu Thr Leu Asn Asn Gly Ser
            370                 375                 380
Gln Ala Val Gly Arg Ser Ser Phe Tyr Cys Leu Glu Tyr Phe Pro Ser
385                 390                 395                 400
Gln Met Leu Arg Thr Gly Asn Asn Phe Thr Phe Ser Tyr Thr Phe Glu
                405                 410                 415
Asp Val Pro Phe His Ser Ser Tyr Ala His Ser Gln Ser Leu Asp Arg
            420                 425                 430
```

```
Leu Met Asn Pro Leu Ile Asp Gln Tyr Leu Tyr Tyr Leu Ser Arg Thr
            435                 440                 445

Asn Thr Pro Ser Gly Thr Thr Thr Gln Ser Arg Leu Gln Phe Ser Gln
450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
        515                 520                 525

Asp Glu Glu Lys Phe Phe Pro Gln Ser Gly Val Leu Ile Phe Gly Lys
    530                 535                 540

Gln Gly Ser Glu Lys Thr Asn Val Asp Ile Glu Lys Val Met Ile Thr
545                 550                 555                 560

Asp Glu Glu Ile Arg Thr Thr Asn Pro Val Ala Thr Glu Gln Tyr
                565                 570                 575

Gly Ser Val Ser Thr Asn Leu Gln Arg Gly Asn Arg Gln Ala Ala Thr
            580                 585                 590

Ala Asp Val Asn Thr Gln Gly Val Leu Pro Gly Met Val Trp Gln Asp
        595                 600                 605

Arg Asp Val Tyr Leu Gln Gly Pro Ile Trp Ala Lys Ile Pro His Thr
    610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Ser Thr Thr Phe Ser Ala Ala Lys Phe Ala Ser Phe Ile Thr Gln
            660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Ile Gln Tyr Thr Ser Asn Tyr
    690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                725                 730                 735

<210> SEQ ID NO 5
<211> LENGTH: 736
<212> TYPE: PRT
<213> ORGANISM: adeno-associated virus serotype 1

<400> SEQUENCE: 5

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80
```

-continued

```
Gln Gln Leu Lys Ala Gly Asp Asn Pro Tyr Leu Arg Tyr Asn His Ala
            85                  90                  95
Asp Ala Glu Phe Gln Glu Arg Leu Gln Glu Asp Thr Ser Phe Gly Gly
                100                 105                 110
Asn Leu Gly Arg Ala Val Phe Gln Ala Lys Lys Arg Val Leu Glu Pro
            115                 120                 125
Leu Gly Leu Val Glu Glu Gly Ala Lys Thr Ala Pro Gly Lys Lys Arg
    130                 135                 140
Pro Val Glu Gln Ser Pro Gln Glu Pro Asp Ser Ser Ser Gly Ile Gly
145                 150                 155                 160
Lys Thr Gly Gln Gln Pro Ala Lys Lys Arg Leu Asn Phe Gly Gln Thr
                165                 170                 175
Gly Asp Ser Glu Ser Val Pro Asp Pro Gln Pro Leu Gly Glu Pro Pro
            180                 185                 190
Ala Thr Pro Ala Ala Val Gly Pro Thr Thr Met Ala Ser Gly Gly Gly
            195                 200                 205
Ala Pro Met Ala Asp Asn Asn Glu Gly Ala Asp Gly Val Gly Asn Ala
        210                 215                 220
Ser Gly Asn Trp His Cys Asp Ser Thr Trp Leu Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Ser Ala Ser Thr Gly Ala Ser Asn Asp Asn His
                260                 265                 270
Tyr Phe Gly Tyr Ser Thr Pro Trp Gly Tyr Phe Asp Phe Asn Arg Phe
            275                 280                 285
His Cys His Phe Ser Pro Arg Asp Trp Gln Arg Leu Ile Asn Asn Asn
        290                 295                 300
Trp Gly Phe Arg Pro Lys Arg Leu Asn Phe Lys Leu Phe Asn Ile Gln
305                 310                 315                 320
Val Lys Glu Val Thr Thr Asn Asp Gly Val Thr Thr Ile Ala Asn Asn
                325                 330                 335
Leu Thr Ser Thr Val Gln Val Phe Ser Asp Ser Glu Tyr Gln Leu Pro
            340                 345                 350
Tyr Val Leu Gly Ser Ala His Gln Gly Cys Leu Pro Pro Phe Pro Ala
            355                 360                 365
Asp Val Phe Met Ile Pro Gln Tyr Gly Tyr Leu Thr Leu Asn Asn Gly
    370                 375                 380
Ser Gln Ala Val Gly Arg Ser Ser Phe Tyr Cys Leu Glu Tyr Phe Pro
385                 390                 395                 400
Ser Gln Met Leu Arg Thr Gly Asn Asn Phe Thr Phe Ser Tyr Thr Phe
                405                 410                 415
Glu Glu Val Pro Phe His Ser Ser Tyr Ala His Ser Gln Ser Leu Asp
            420                 425                 430
Arg Leu Met Asn Pro Leu Ile Asp Gln Tyr Leu Tyr Tyr Leu Asn Arg
        435                 440                 445
Thr Gln Asn Gln Ser Gly Ser Ala Gln Asn Lys Asp Leu Leu Phe Ser
    450                 455                 460
Arg Gly Ser Pro Ala Gly Met Ser Val Gln Pro Lys Asn Trp Leu Pro
465                 470                 475                 480
Gly Pro Cys Tyr Arg Gln Gln Arg Val Ser Lys Thr Lys Thr Asp Asn
                485                 490                 495
```

Asn Asn Ser Asn Phe Thr Trp Thr Gly Ala Ser Lys Tyr Asn Leu Asn
                500                 505                 510

Gly Arg Glu Ser Ile Ile Asn Pro Gly Thr Ala Met Ala Ser His Lys
            515                 520                 525

Asp Asp Glu Asp Lys Phe Phe Pro Met Ser Gly Val Met Ile Phe Gly
        530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Phe Gln Ser Ser Thr Asp Pro Ala
            580                 585                 590

Thr Gly Asp Val His Ala Met Gly Ala Leu Pro Gly Met Val Trp Gln
        595                 600                 605

Asp Arg Asp Val Tyr Leu Gln Gly Pro Ile Trp Ala Lys Ile Pro His
        610                 615                 620

Thr Asp Gly His Phe His Pro Ser Pro Leu Met Gly Gly Phe Gly Leu
625                 630                 635                 640

Lys Asn Pro Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Val Gln Tyr Thr Ser Asn
690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735

<210> SEQ ID NO 6
<211> LENGTH: 736
<212> TYPE: PRT
<213> ORGANISM: adeno-associated virus serotype 3

<400> SEQUENCE: 6

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Val Pro Gln Pro
            20                  25                  30

Lys Ala Asn Gln Gln His Gln Asp Asn Arg Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Ile Leu Glu Pro
        115                 120                 125

Leu Gly Leu Val Glu Glu Ala Ala Lys Thr Ala Pro Gly Lys Lys Gly
    130                 135                 140

```
Ala Val Asp Gln Ser Pro Gln Glu Pro Asp Ser Ser Gly Val Gly
145                 150                 155                 160

Lys Ser Gly Lys Gln Pro Ala Arg Lys Arg Leu Asn Phe Gly Gln Thr
                165                 170                 175

Gly Asp Ser Glu Ser Val Pro Asp Pro Gln Pro Leu Gly Glu Pro Pro
                180                 185                 190

Ala Ala Pro Thr Ser Leu Gly Ser Asn Thr Met Ala Ser Gly Gly Gly
                195                 200                 205

Ala Pro Met Ala Asp Asn Asn Glu Gly Ala Asp Gly Val Gly Asn Ser
            210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
                260                 265                 270

Phe Gly Tyr Ser Thr Pro Trp Gly Tyr Phe Asp Phe Asn Arg Phe His
            275                 280                 285

Cys His Phe Ser Pro Arg Asp Trp Gln Arg Leu Ile Asn Asn Asn Trp
    290                 295                 300

Gly Phe Arg Pro Lys Lys Leu Ser Phe Lys Leu Phe Asn Ile Gln Val
305                 310                 315                 320

Arg Gly Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
                340                 345                 350

Val Leu Gly Ser Ala His Gln Gly Cys Leu Pro Pro Phe Pro Ala Asp
            355                 360                 365

Val Phe Met Val Pro Gln Tyr Gly Tyr Leu Thr Leu Asn Asn Gly Ser
    370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Gln Phe Ser Tyr Thr Phe Glu
                405                 410                 415

Asp Val Pro Phe His Ser Ser Tyr Ala His Ser Gln Ser Leu Asp Arg
                420                 425                 430

Leu Met Asn Pro Leu Ile Asp Gln Tyr Leu Tyr Tyr Leu Asn Arg Thr
            435                 440                 445

Gln Gly Thr Thr Ser Gly Thr Thr Asn Gln Ser Arg Leu Leu Phe Ser
450                 455                 460

Gln Ala Gly Pro Gln Ser Met Ser Leu Gln Ala Arg Asn Trp Leu Pro
465                 470                 475                 480

Gly Pro Cys Tyr Arg Gln Gln Arg Leu Ser Lys Thr Ala Asn Asp Asn
                485                 490                 495

Asn Asn Ser Asn Phe Pro Trp Thr Ala Ala Ser Lys Tyr His Leu Asn
                500                 505                 510

Gly Arg Asp Ser Leu Val Asn Pro Gly Pro Ala Met Ala Ser His Lys
            515                 520                 525

Asp Asp Glu Glu Lys Phe Phe Pro Met His Gly Asn Leu Ile Phe Gly
    530                 535                 540

Lys Glu Gly Thr Thr Ala Ser Asn Ala Glu Leu Asp Asn Val Met Ile
545                 550                 555                 560
```

-continued

Thr Asp Glu Glu Ile Arg Thr Thr Asn Pro Val Ala Thr Glu Gln
            565                 570                 575

Tyr Gly Thr Val Ala Asn Asn Leu Gln Ser Ser Asn Thr Ala Pro Thr
        580                 585                 590

Thr Gly Thr Val Asn His Gln Gly Ala Leu Pro Gly Met Val Trp Gln
        595                 600                 605

Asp Arg Asp Val Tyr Leu Gln Gly Pro Ile Trp Ala Lys Ile Pro His
            610                 615                 620

Thr Asp Gly His Phe His Pro Ser Pro Leu Met Gly Gly Phe Gly Leu
625                 630                 635                 640

Lys His Pro Pro Pro Gln Ile Met Ile Lys Asn Thr Pro Val Pro Ala
            645                 650                 655

Asn Pro Pro Thr Thr Phe Ser Pro Ala Lys Phe Ala Ser Phe Ile Thr
            660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Ile Gln Tyr Thr Ser Asn
        690                 695                 700

Tyr Asn Lys Ser Val Asn Val Asp Phe Thr Val Asp Thr Asn Gly Val
705                 710                 715                 720

Tyr Ser Glu Pro Arg Pro Ile Gly Thr Arg Tyr Leu Thr Arg Asn Leu
            725                 730                 735

<210> SEQ ID NO 7
<211> LENGTH: 736
<212> TYPE: PRT
<213> ORGANISM: adeno-associated virus serotype 9

<400> SEQUENCE: 7

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Ser Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Glu Ala Pro Ser Gly Leu Gly Pro Asn Thr Met Ala Ser Gly Gly Gly
        195                 200                 205

```
Ala Pro Met Ala Asp Asn Asn Glu Gly Ala Asp Gly Val Gly Asn Ser
    210                 215                 220
Ser Gly Asn Trp His Cys Asp Ser Thr Trp Leu Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Asn Gly Thr Ser Gly Ser Thr Asn Asp Asn
            260                 265                 270
Thr Tyr Phe Gly Tyr Ser Thr Pro Trp Gly Tyr Phe Asp Phe Asn Arg
        275                 280                 285
Phe His Cys His Phe Ser Pro Arg Asp Trp Gln Arg Leu Ile Asn Asn
    290                 295                 300
Asn Trp Gly Phe Arg Pro Lys Arg Leu Asn Phe Lys Leu Phe Asn Ile
305                 310                 315                 320
Gln Val Lys Glu Val Thr Thr Asn Gly Thr Lys Thr Ile Ala Asn
                325                 330                 335
Asn Leu Thr Ser Thr Val Gln Val Phe Thr Asp Ser Glu Tyr Gln Leu
            340                 345                 350
Pro Tyr Val Leu Gly Ser Ala His Gln Gly Cys Leu Pro Pro Phe Pro
        355                 360                 365
Ala Asp Val Phe Met Val Pro Gln Tyr Gly Tyr Leu Thr Leu Asn Asn
    370                 375                 380
Gly Ser Gln Ala Leu Gly Arg Ser Ser Phe Tyr Cys Leu Glu Tyr Phe
385                 390                 395                 400
Pro Ser Gln Met Leu Arg Thr Gly Asn Asn Phe Gln Phe Ser Tyr Thr
                405                 410                 415
Phe Glu Asp Val Pro Phe His Ser Ser Tyr Ala His Ser Gln Ser Leu
            420                 425                 430
Asp Arg Leu Met Asn Pro Leu Ile Asp Gln Tyr Leu Tyr Tyr Leu Val
        435                 440                 445
Arg Thr Gln Thr Thr Gly Thr Gly Gly Thr Gln Thr Leu Ala Phe Ser
    450                 455                 460
Gln Ala Gly Pro Ser Ser Met Ala Asn Gln Ala Arg Asn Trp Val Pro
465                 470                 475                 480
Gly Pro Cys Tyr Arg Gln Gln Arg Val Ser Thr Thr Thr Asn Gln Asn
                485                 490                 495
Asn Asn Ser Asn Phe Ala Trp Thr Gly Ala Ala Lys Phe Lys Leu Asn
            500                 505                 510
Gly Arg Asp Ser Leu Met Asn Pro Gly Val Ala Met Ala Ser His Lys
        515                 520                 525
Asp Asp Glu Asp Arg Phe Phe Pro Ser Ser Gly Val Leu Ile Phe Gly
    530                 535                 540
Lys Gln Gly Ala Gly Asn Asp Gly Val Asp Tyr Ser Gln Val Leu Ile
545                 550                 555                 560
Thr Asp Glu Glu Glu Ile Lys Ala Thr Asn Pro Val Ala Thr Glu Glu
                565                 570                 575
Tyr Gly Ala Val Ala Ile Asn Asn Gln Ala Ala Asn Thr Gln Ala Gln
            580                 585                 590
Thr Gly Leu Val His Asn Gln Gly Val Ile Pro Gly Met Val Trp Gln
        595                 600                 605
Asn Arg Asp Val Tyr Leu Gln Gly Pro Ile Trp Ala Lys Ile Pro His
    610                 615                 620
```

```
Thr Asp Gly Asn Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                645                 650                 655

Asp Pro Pro Leu Thr Phe Asn Gln Ala Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Thr Asn Val Asp Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735
```

<210> SEQ ID NO 8
<211> LENGTH: 737
<212> TYPE: PRT
<213> ORGANISM: adeno-associated virus serotpye 7

<400> SEQUENCE: 8

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asn Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Ala Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Ser Val Gly Ser Gly Thr Val Ala Ala Gly Gly
        195                 200                 205

Gly Ala Pro Met Ala Asp Asn Asn Glu Gly Ala Asp Gly Val Gly Asn
    210                 215                 220

Ala Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Ser Glu Thr Ala Gly Ser Thr Asn Asp Asn
            260                 265                 270
```

-continued

```
Thr Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Lys Leu Arg Phe Lys Leu Phe Asn Ile
305                 310                 315                 320

Gln Val Lys Glu Val Thr Thr Asn Asp Gly Val Thr Thr Ile Ala Asn
                325                 330                 335

Asn Leu Thr Ser Thr Ile Gln Val Phe Ser Asp Ser Glu Tyr Gln Leu
            340                 345                 350

Pro Tyr Val Leu Gly Ser Ala His Gln Gly Cys Leu Pro Pro Phe Pro
        355                 360                 365

Ala Asp Val Phe Met Ile Pro Gln Tyr Gly Tyr Leu Thr Leu Asn Asn
    370                 375                 380

Gly Ser Gln Ser Val Gly Arg Ser Ser Phe Tyr Cys Leu Glu Tyr Phe
385                 390                 395                 400

Pro Ser Gln Met Leu Arg Thr Gly Asn Asn Phe Glu Phe Ser Tyr Ser
                405                 410                 415

Phe Glu Asp Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ala
        435                 440                 445

Arg Thr Gln Ser Asn Pro Gly Gly Thr Ala Gly Asn Arg Glu Leu Gln
    450                 455                 460

Phe Tyr Gln Gly Gly Pro Ser Thr Met Ala Glu Gln Ala Lys Asn Trp
465                 470                 475                 480

Leu Pro Gly Pro Cys Phe Arg Gln Gln Arg Val Ser Lys Thr Leu Asp
                485                 490                 495

Gln Asn Asn Asn Ser Asn Phe Ala Trp Thr Gly Ala Thr Lys Tyr His
            500                 505                 510

Leu Asn Gly Arg Asn Ser Leu Val Asn Pro Gly Val Ala Met Ala Thr
        515                 520                 525

His Lys Asp Asp Glu Asp Arg Phe Phe Pro Ser Ser Gly Val Leu Ile
    530                 535                 540

Phe Gly Lys Thr Gly Ala Thr Asn Lys Thr Thr Leu Glu Asn Val Leu
545                 550                 555                 560

Met Thr Asn Glu Glu Glu Ile Arg Pro Thr Asn Pro Val Ala Thr Glu
                565                 570                 575

Glu Tyr Gly Ile Val Ser Ser Asn Leu Gln Ala Ala Asn Thr Ala Ala
            580                 585                 590

Gln Thr Gln Val Val Asn Asn Gln Gly Ala Leu Pro Gly Met Val Trp
        595                 600                 605

Gln Asn Arg Asp Val Tyr Leu Gln Gly Pro Ile Trp Ala Lys Ile Pro
    610                 615                 620

His Thr Asp Gly Asn Phe His Pro Ser Pro Leu Met Gly Gly Phe Gly
625                 630                 635                 640

Leu Lys His Pro Pro Pro Gln Ile Leu Ile Lys Asn Thr Pro Val Pro
                645                 650                 655

Ala Asn Pro Pro Glu Val Phe Thr Pro Ala Lys Phe Ala Ser Phe Ile
            660                 665                 670

Thr Gln Tyr Ser Thr Gly Gln Val Ser Val Glu Ile Glu Trp Glu Leu
        675                 680                 685
```

-continued

```
Gln Lys Glu Asn Ser Lys Arg Trp Asn Pro Glu Ile Gln Tyr Thr Ser
    690             695             700

Asn Phe Glu Lys Gln Thr Gly Val Asp Phe Ala Val Asp Ser Gln Gly
705             710             715             720

Val Tyr Ser Glu Pro Arg Pro Ile Gly Thr Arg Tyr Leu Thr Arg Asn
                725             730             735

Leu
```

ADENO-ASSOCIATED VIRUS (AAV) SEROTYPE 8 SEQUENCES, VECTORS CONTAINING SAME, AND USES THEREFOR

CROSS-REFERENCE TO RELATED APPLICATIONS

This application is a continuation of U.S. patent application Ser. No. 15/298,760, filed Oct. 20, 2016, which is a divisional of U.S. patent application Ser. No. 14/598,462, filed Jan. 16, 2015, now U.S. Pat. No. 9,493,788, issued Nov. 15, 2016, which is a divisional of U.S. patent application Ser. No. 11/981,022, filed Oct. 31, 2007, now U.S. Pat. No. 8,962,330, issued Feb. 24, 2015, which is a continuation of U.S. patent application Ser. No. 11/899,500, filed Sep. 6, 2007, now U.S. Pat. No. 7,790,449, issued Sep. 7, 2010, which is a continuation of U.S. patent application Ser. No. 10/423,704, filed Apr. 25, 2003, now U.S. Pat. No. 7,282,199, issued Oct. 16, 2007, which is a continuation-in-part of International Patent Application No. PCT/US02/33630, filed Nov. 12, 2002, which claims the benefit under 35 USC 119(e) of US Provisional Patent Application No. 60/386,122, filed Jun. 5, 2002, US Provisional Patent Application No. 60/377,133, filed May 1, 2002, and US Provisional Patent Application No. 60/341,151, filed Dec. 17, 2001, which applications are incorporated herein by reference in their entireties.

STATEMENT REGARDING FEDERALLY SPONSORED RESEARCH OR DEVELOPMENT

This invention was made with government support under DK047757 and HL059407 awarded by the National Institutes of Health. The government has certain rights in the invention.

INCORPORATION-BY-REFERENCE OF MATERIAL SUBMITTED IN ELECTRONIC FORM

The Sequence Listing material filed in electronic form herewith is hereby incorporated by reference. This file is labeled "UPN-02733USC7_ST25.txt", was created on Aug. 31, 2018, and is 50,057 bytes (48.8 KB).

BACKGROUND OF THE INVENTION

Adeno-associated virus (AAV), a member of the Parvovirus family, is a small nonenveloped, icosahedral virus with single-stranded linear DNA genomes of 4.7 kilobases (kb) to 6 kb. AAV is assigned to the genus, *Dependovirus*, because the virus was discovered as a contaminant in purified adenovirus stocks. AAV's life cycle includes a latent phase at which AAV genomes, after infection, are site specifically integrated into host chromosomes and an infectious phase in which, following either adenovirus or herpes simplex virus infection, the integrated genomes are subsequently rescued, replicated, and packaged into infectious viruses. The properties of non-pathogenicity, broad host range of infectivity, including non-dividing cells, and potential site-specific chromosomal integration make AAV an attractive tool for gene transfer.

Recent studies suggest that AAV vectors may be the preferred vehicle for gene delivery. To date, there have been 6 different serotypes of AAVs isolated from human or non-human primates (NHP) and well characterized. Among them, human serotype 2 is the first AAV that was developed as a gene transfer vector; it has been widely used for efficient gene transfer experiments in different target tissues and animal models. Clinical trials of the experimental application of AAV2 based vectors to some human disease models are in progress, and include such diseases as cystic fibrosis and hemophilia B.

What are desirable are AAV-based constructs for gene delivery.

SUMMARY OF THE INVENTION

In one aspect, the invention provides novel AAV sequences, compositions containing these sequences, and uses therefor. Advantageously, these compositions are particularly well suited for use in compositions requiring re-administration of rAAV for therapeutic or prophylactic purposes.

These and other aspects of the invention will be readily apparent from the following detailed description of the invention.

BRIEF DESCRIPTION OF THE DRAWINGS

FIGS. 1A through 1C are the nucleic acid sequences of the rep and cap regions of AAV8 [SEQ ID NO:1].

FIGS. 2A through 2C are the amino acid sequences of the AAV8 capsid vp1 protein [SEQ ID NO:2], provided in alignment with the vp1 of the published sequences of AAV2 [SEQ ID NO:4], AAV1 [SEQ ID NO:5], and AAV3 [SEQ ID NO:6], and newly identified AAV serotypes AAV7 [SEQ ID NO: 8] and AAV9 [SEQ ID NO:7]. The alignment was performed using the Clustal W program, with the number of AAV2 used for reference. Underlining and bold at the bottom sequence of the alignment indicates cassettes of identity. The dots in the alignment indicate that the amino acids are missing at the positions in the alignment as compared to AAV2 VP1.

FIGS. 3A through 3C are the amino acid sequences of the AAV8 rep proteins [SEQ ID NO:3].

DETAILED DESCRIPTION OF THE INVENTION

The invention provides the nucleic acid sequences and amino acids of a novel AAV serotype, AAV8. Also provided are fragments of these AAV sequences. Each of these fragments may be readily utilized in a variety of vector systems and host cells. Among desirable AAV8 fragments are the cap proteins, including the vp1, vp2, vp3 and hypervariable regions, the rep proteins, including rep 78, rep 68, rep 52, and rep 40, and the sequences encoding these proteins. These fragments may be readily utilized in a variety of vector systems and host cells. Such fragments may be used alone, in combination with other AAV8 sequences or fragments, or in combination with elements from other AAV or non-AAV viral sequences. In one particularly desirable embodiment, a vector contains the AAV8 cap and/or rep sequences of the invention.

The AAV8 sequences and fragments thereof are useful in production of rAAV, and are also useful as antisense delivery vectors, gene therapy vectors, or vaccine vectors. The invention further provides nucleic acid molecules, gene delivery vectors, and host cells which contain the AAV8 sequences of the invention.

Suitable fragments can be determined using the information provided herein. Alignments are performed using any of a variety of publicly or commercially available Multiple Sequence Alignment Programs, such as AClustal W≅, accessible through Web Servers on the internet. Alternatively, Vector NTI utilities are also used. There are also a number of algorithms known in the art which can be used to measure nucleotide sequence identity, including those contained in the programs described above. As another example, polynucleotide sequences can be compared using Fasta, a program in GCG Version 6.1. Fasta provides alignments and percent sequence identity of the regions of the best overlap between the query and search sequences. For instance, percent sequence identity between nucleic acid sequences can be determined using Fasta with its default parameters (a word size of 6 and the NOPAM factor for the scoring matrix) as provided in GCG Version 6.1, herein incorporated by reference. Similar programs are available for amino acid sequences, e.g., the "Clustal X" program. Generally, any of these programs are used at default settings, although one of skill in the art can alter these settings as needed. Alternatively, one of skill in the art can utilize another algorithm or computer program which provides at least the level of identity or alignment as that provided by the referenced algorithms and programs.

The term "substantial homology" or "substantial similarity," when referring to a nucleic acid, or fragment thereof, indicates that, when optimally aligned with appropriate nucleotide insertions or deletions with another nucleic acid (or its complementary strand), there is nucleotide sequence identity in at least about 95 to 99% of the aligned sequences. Preferably, the homology is over full-length sequence, or an open reading frame thereof, or another suitable fragment which is at least 15 nucleotides in length. Examples of suitable fragments are described herein.

The term "substantial homology" or "substantial similarity," when referring to amino acids or fragments thereof, indicates that, when optimally aligned with appropriate amino acid insertions or deletions with another amino acid (or its complementary strand), there is amino acid sequence identity in at least about 95 to 99% of the aligned sequences. Preferably, the homology is over full-length sequence, or a protein thereof, e.g., a cap protein, a rep protein, or a fragment thereof which is at least 8 amino acids, or more desirably, at least 15 amino acids in length. Examples of suitable fragments are described herein.

By the term "highly conserved" is meant at least 80% identity, preferably at least 90% identity, and more preferably, over 97% identity. Identity is readily determined by one of skill in the art by resort to algorithms and computer programs known by those of skill in the art.

The term "percent sequence identity" or "identical" in the context of nucleic acid sequences refers to the residues in the two sequences which are the same when aligned for maximum correspondence. The length of sequence identity comparison may be over the full-length of the genome, the full-length of a gene coding sequence, or a fragment of at least about 500 to 5000 nucleotides, is desired. However, identity among smaller fragments, e.g. of at least about nine nucleotides, usually at least about 20 to 24 nucleotides, at least about 28 to 32 nucleotides, at least about 36 or more nucleotides, may also be desired. Similarly, "percent sequence identity" may be readily determined for amino acid sequences, over the full-length of a protein, or a fragment thereof. Suitably, a fragment is at least about 8 amino acids in length, and may be up to about 700 amino acids. Examples of suitable fragments are described herein.

As described herein, the vectors of the invention containing the AAV capsid proteins of the invention are particularly well suited for use in applications in which the neutralizing antibodies diminish the effectiveness of other AAV serotype based vectors, as well as other viral vectors. The rAAV vectors of the invention are particularly advantageous in rAAV readministration and repeat gene therapy.

These and other embodiments and advantages of the invention are described in more detail below. As used throughout this specification and the claims, the terms "comprising" and "including" are inclusive of other components, elements, integers, steps and the like. Conversely, the term "consisting" and its variants are exclusive of other components, elements, integers, steps and the like.

I. AAV Serotype 8 Sequences

A. Nucleic Acid Sequences

The AAV8 nucleic acid sequences of the invention include the DNA sequences of FIG. 1 [SEQ ID NO: 1], which consists of 4396 nucleotides. The AAV8 nucleic acid sequences of the invention further encompass the strand which is complementary to FIG. 1 [SEQ ID NO: 1], as well as the RNA and cDNA sequences corresponding to FIG. 1 [SEQ ID NO: 1] and its complementary strand. Also included in the nucleic acid sequences of the invention are natural variants and engineered modifications of FIG. 1 [SEQ ID NO: 1] and its complementary strand. Such modifications include, for example, labels which are known in the art, methylation, and substitution of one or more of the naturally occurring nucleotides with a degenerate nucleotide.

Further included in this invention are nucleic acid sequences which are greater than about 90%, more preferably at least about 95%, and most preferably at least about 98 to 99% identical or homologous to FIG. 1 [SEQ ID NO:1].

Also included within the invention are fragments of FIG. 1 [SEQ ID NO: 1], its complementary strand, cDNA and RNA complementary thereto. Suitable fragments are at least 15 nucleotides in length, and encompass functional fragments, i.e., fragments which are of biological interest. Such fragments include the sequences encoding the three variable proteins (vp) of the AAV8 capsid which are alternative splice variants: vp1 [nt 2121 to 4335 of FIG. 1, SEQ ID NO:1]; vp2 [nt 2532 to 4335 of FIG. 1, SEQ ID NO:1]; and vp 3 [nt 2730 to 4335 of FIG. 1, SEQ ID NO:1]. Other suitable fragments of FIG. 1 [SEQ ID NO:1], include the fragment which contains the start codon for the AAV8 capsid protein, and the fragments encoding the hypervariable regions of the vp1 capsid protein, which are described herein.

Still other fragments include those encoding the rep proteins, including rep 78 [initiation codon located at nt 227 of FIG. 1, SEQ ID NO:1], rep 68 [initiation codon located at nt 227 of FIG. 1, SEQ ID NO:1], rep 52 [initiation codon located at nt 905 of FIG. 1, SEQ ID NO:1], and rep 40 [initiation codon located at nt 905 of FIG. 1, SEQ ID NO:1]. Other fragments of interest may include the AAV8 inverted terminal repeat which can be identified by the methods described herein, AAV P19 sequences, AAV8 P40 sequences, the rep binding site, and the terminal resolute site (TRS). Still other suitable fragments will be readily apparent to those of skill in the art.

In addition to including the nucleic acid sequences provided in the figures and Sequence Listing, the present invention includes nucleic acid molecules and sequences which are designed to express the amino acid sequences, proteins and peptides of the AAV serotypes of the invention. Thus, the invention includes nucleic acid sequences which encode the following novel AAV amino acid sequences and artificial AAV serotypes generated using these sequences and/or unique fragments thereof.

As used herein, artificial AAV serotypes include, without limitation, AAV with a non-naturally occurring capsid protein. Such an artificial capsid may be generated by any suitable technique, using a novel AAV sequence of the invention (e.g., a fragment of a vp1 capsid protein) in combination with heterologous sequences which may be obtained from another AAV serotype (known or novel), non-contiguous portions of the same AAV serotype, from a non-AAV viral source, or from a non-viral source. An artificial AAV serotype may be, without limitation, a chimeric AAV capsid, a recombinant AAV capsid, or a "humanized" AAV capsid.

B. AAV8 Amino Acid Sequences, Proteins and Peptides

The invention further provides proteins and fragments thereof which are encoded by the AAV8 nucleic acids of the invention, and AAV8 amino acids which are generated by other methods. The invention further encompasses AAV serotypes generated using sequences of the novel AAV serotype of the invention, which are generated using synthetic, recombinant or other techniques known to those of skill in the art. The invention is not limited to novel AAV amino acid sequences, peptides and proteins expressed from the novel AAV nucleic acid sequences of the invention and encompasses amino acid sequences, peptides and proteins generated by other methods known in the art, including, e.g., by chemical synthesis, by other synthetic techniques, or by other methods. For example, the sequences of any of be readily generated using a variety of techniques.

Suitable production techniques are well known to those of skill in the art. See, e.g., Sambrook et al, Molecular Cloning: A Laboratory Manual, Cold Spring Harbor Press (Cold Spring Harbor, N.Y.). Alternatively, peptides can also be synthesized by the well known solid phase peptide synthesis methods (Merrifield, *J. Am. Chem. Soc.*, 85:2149 (1962); Stewart and Young, Solid Phase Peptide Synthesis (Freeman, San Francisco, 1969) pp. 27-62). These and other suitable production methods are within the knowledge of those of skill in the art and are not a limitation of the present invention.

Particularly desirable proteins include the AAV capsid proteins, which are encoded by the nucleotide sequences identified above. The AAV capsid is composed of three proteins, vp1, vp2 and vp3, which are alternative splice variants. The full-length sequence provided in FIG. 2 is that of vp1. The AAV8 capsid proteins include vp1 [aa 1 to 737 of SEQ ID NO:2], vp2 [aa 138 to 737 of SEQ ID NO:2], and vp3 [aa 203 to 737 of SEQ ID NO: 2] and functional fragments thereof. Other desirable fragments of the capsid protein include the constant and variable regions, located between hypervariable regions (HPV). Other desirable fragments of the capsid protein include the HPV themselves.

An algorithm developed to determine areas of sequence divergence in AAV2 has yielded 12 hypervariable regions (HVR) of which 5 overlap or are part of the four previously described variable regions. [Chiorini et al, *J. Virol*, 73:1309-19 (1999); Rutledge et al, *J. Virol.*, 72:309-319] Using this algorithm and/or the alignment techniques described herein, the HVR of the novel AAV serotypes are determined. For example, with respect to the number of the AAV2 vp1 [SEQ ID NO:4], the HVR are located as follows: HVR1, aa 146-152; HVR2, aa 182-186; HVR3, aa 262-264; HVR4, aa 381-383; HVR5, aa 450-474; HVR6, aa 490-495; HVR7, aa500-504; HVR8, aa 514-522; HVR9, aa 534-555; HVR10, aa 581-594; HVR11, aa 658-667; and HVR12, aa 705-719. Using the alignment provided herein performed using the Clustal X program at default settings, or using other commercially or publicly available alignment programs at default settings, one of skill in the art can readily determine corresponding fragments of the novel AAV capsids of the invention.

Still other desirable fragments of the AAV8 capsid protein include amino acids 1 to 184 of SEQ ID NO: 2, amino acids 199 to 259; amino acids 274 to 446; amino acids 603 to 659; amino acids 670 to 706; amino acids 724 to 736 of SEQ ID NO:2; aa 185-198; aa 260-273; aa447-477; aa495-602; aa660-669; and aa707-723. Additionally, examples of other suitable fragments of AAV capsids include, with respect to the numbering of AAV2 [SEQ ID NO:4], aa 24-42, aa 25-28; aa 81-85; aa133-165; aa 134-165; aa 137-143; aa 154-156; aa 194-208; aa 261-274; aa 262-274; aa 171-173; aa 413-417; aa 449-478; aa 494-525; aa 534-571; aa 581-601; aa 660-671; aa 709-723. Still other desirable fragments include, for example, in AAV7, amino acids 1 to 184 of SEQ ID NO:2, amino acids 199 to 259; amino acids 274 to 446; amino acids 603 to 659; amino acids 670 to 706; amino acids 724 to 736; aa 185 to 198; aa 260 to 273; aa447 to 477; aa495 to 602; aa660 to 669; and aa707 to 723. Using the alignment provided herein performed using the Clustal X program at default settings, or using other commercially or publicly available alignment programs at default settings, one of skill in the art can readily determine corresponding fragments of the novel AAV capsids of the invention.

Still other desirable AAV8 proteins include the rep proteins include rep68/78 and rep40/52 [located within aa 1 to 625 of SEQ ID NO: 3]. Suitable fragments of the rep proteins may include aa 1 to 102; aa 103 to 140; aa 141 to 173; aa 174 to 226; aa 227 to 275; aa 276 to 374; aa 375 to 383; aa 384 to 446; aa 447 to 542; aa 543 to 555; aa 556 to 625, of SEQ ID NO: 3.

Suitably, fragments are at least 8 amino acids in length. However, fragments of other desired lengths may be readily utilized. Such fragments may be produced recombinantly or by other suitable means, e.g., chemical synthesis.

The invention further provides other AAV8 sequences which are identified using the sequence information provided herein. For example, given the AAV8 sequences provided herein, infectious AAV8 may be isolated using genome walking technology (Siebert et al., 1995, *Nucleic Acid Research*, 23:1087-1088, Friezner-Degen et al., 1986, *J. Biol. Chem.* 261:6972-6985, BD Biosciences Clontech, Palo Alto, Calif.). Genome walking is particularly well suited for identifying and isolating the sequences adjacent to the novel sequences identified according to the method of the invention. This technique is also useful for isolating inverted terminal repeat (ITRs) of the novel AAV8 serotype, based upon the novel AAV capsid and rep sequences provided herein.

The sequences, proteins, and fragments of the invention may be produced by any suitable means, including recombinant production, chemical synthesis, or other synthetic means. Such production methods are within the knowledge of those of skill in the art and are not a limitation of the present invention.

IV. Production of rAAV with AAV8 Capsids

The invention encompasses novel, wild-type AAV8, the sequences of which are free of DNA and/or cellular material with these viruses are associated in nature. In another aspect, the present invention provides molecules which utilize the novel AAV sequences of the invention, including fragments thereof, for production of molecules useful in delivery of a heterologous gene or other nucleic acid sequences to a target cell.

In another aspect, the present invention provides molecules which utilize the AAV8 sequences of the invention, including fragments thereof, for production of viral vectors useful in delivery of a heterologous gene or other nucleic acid sequences to a target cell.

The molecules of the invention which contain AAV8 sequences include any genetic element (vector) which may be delivered to a host cell, e.g., naked DNA, a plasmid, phage, transposon, cosmid, episome, a protein in a non-viral delivery vehicle (e.g., a lipid-based carrier), virus, etc. which transfer the sequences carried thereon. The selected vector may be delivered by any suitable method, including transfection, electroporation, liposome delivery, membrane fusion techniques, high velocity DNA-coated pellets, viral infection and protoplast fusion. The methods used to construct any embodiment of this invention are known to those with skill in nucleic acid manipulation and include genetic engineering, recombinant engineering, and synthetic techniques. See, e.g., Sambrook et al, Molecular Cloning: A Laboratory Manual, Cold Spring Harbor Press, Cold Spring Harbor, N.Y.

In one embodiment, the vectors of the invention contain, at a minimum, sequences encoding an AAV8 capsid or a fragment thereof. In another embodiment, the vectors of the invention contain, at a minimum, sequences encoding an AAV8 rep protein or a fragment thereof. Optionally, such vectors may contain both AAV cap and rep proteins. In vectors in which both AAV rep and cap are provides, the AAV rep and AAV cap sequences can both be of AAV8 origin. Alternatively, the present invention provides vectors in which the rep sequences are from an AAV serotype which differs from that which is providing the cap sequences. In one embodiment, the rep and cap sequences are expressed from separate sources (e.g., separate vectors, or a host cell and a vector). In another embodiment, these rep sequences are fused in frame to cap sequences of a different AAV serotype to form a chimeric AAV vector. Optionally, the vectors of the invention further contain a minigene comprising a selected transgene which is flanked by AAV 5' ITR and AAV 3' ITR.

Thus, in one embodiment, the vectors described herein contain nucleic acid sequences encoding an intact AAV capsid which may be from a single AAV serotype (e.g., AAV8). Such a capsid may comprise amino acids 1 to 738 of SEQ ID NO:2. Alternatively, these vectors contain sequences encoding artificial capsids which contain one or more fragments of the AAV8 capsid fused to heterologous AAV or non-AAV capsid proteins (or fragments thereof). These artificial capsid proteins are selected from non-contiguous portions of the AAV8 capsid or from capsids of other AAV serotypes. For example, a rAAV may have a capsid protein comprising one or more of the AAV8 capsid regions selected from the vp2 and/or vp3, or from vp 1, or fragments thereof selected from amino acids 1 to 184, amino acids 199 to 259; amino acids 274 to 446; amino acids 603 to 659; amino acids 670 to 706; amino acids 724 to 738 of the AAV8 capsid, SEQ ID NO: 2. In another example, it may be desirable to alter the start codon of the vp3 protein to GTG. Alternatively, the rAAV may contain one or more of the AAV serotype 8 capsid protein hypervariable regions which are identified herein, or other fragment including, without limitation, aa 185-198; aa 260-273; aa447-477; aa495-602; aa660-669; and aa707-723 of the AAV8 capsid. See, SEQ ID NO: 2. These modifications may be to increase expression, yield, and/or to improve purification in the selected expression systems, or for another desired purpose (e.g., to change tropism or alter neutralizing antibody epitopes).

The vectors described herein, e.g., a plasmid, are useful for a variety of purposes, but are particularly well suited for use in production of a rAAV containing a capsid comprising AAV sequences or a fragment thereof. These vectors, including rAAV, their elements, construction, and uses are described in detail herein.

In one aspect, the invention provides a method of generating a recombinant adeno-associated virus (AAV) having an AAV serotype 8 capsid, or a portion thereof. Such a method involves culturing a host cell which contains a nucleic acid sequence encoding an adeno-associated virus (AAV) serotype 8 capsid protein, or fragment thereof, as defined herein; a functional rep gene; a minigene composed of, at a minimum, AAV inverted terminal repeats (ITRs) and a transgene; and sufficient helper functions to permit packaging of the minigene into the AAV8 capsid protein.

The components required to be cultured in the host cell to package an AAV minigene in an AAV capsid may be provided to the host cell in trans. Alternatively, any one or more of the required components (e.g., minigene, rep sequences, cap sequences, and/or helper functions) may be provided by a stable host cell which has been engineered to contain one or more of the required components using methods known to those of skill in the art. Most suitably, such a stable host cell will contain the required component(s) under the control of an inducible promoter. However, the required component(s) may be under the control of a constitutive promoter. Examples of suitable inducible and constitutive promoters are provided herein, in the discussion of regulatory elements suitable for use with the transgene. In still another alternative, a selected stable host cell may contain selected component(s) under the control of a constitutive promoter and other selected component(s) under the control of one or more inducible promoters. For example, a stable host cell may be generated which is derived from 293 cells (which contain E1 helper functions under the control of a constitutive promoter), but which contains the rep and/or cap proteins under the control of inducible promoters. Still other stable host cells may be generated by one of skill in the art.

The minigene, rep sequences, cap sequences, and helper functions required for producing the rAAV of the invention may be delivered to the packaging host cell in the form of any genetic element which transfer the sequences carried thereon. The selected genetic element may be delivered by any suitable method, including those described herein. The methods used to construct any embodiment of this invention are known to those with skill in nucleic acid manipulation and include genetic engineering, recombinant engineering, and synthetic techniques. See, e.g., Sambrook et al, Molecular Cloning: A Laboratory Manual, Cold Spring Harbor Press, Cold Spring Harbor, N.Y. Similarly, methods of generating rAAV virions are well known and the selection of a suitable method is not a limitation on the present invention. See, e.g., K. Fisher et al, *J. Virol.*, 70:520-532 (1993) and U.S. Pat. No. 5,478,745.

Unless otherwise specified, the AAV ITRs, and other selected AAV components described herein, may be readily selected from among any AAV serotype, including, without limitation, AAV1, AAV2, AAV3, AAV4, AAV5, AAV6, AAV7, AAV9 and the novel serotype of the invention, AAV8. These ITRs or other AAV components may be readily isolated using techniques available to those of skill in the art from an AAV serotype. Such AAV may be isolated or obtained from academic, commercial, or public sources (e.g., the American Type Culture Collection, Manassas, Va.). Alternatively, the AAV sequences may be obtained through synthetic or other suitable means by reference to published sequences such as are available in the literature or in databases such as, e.g., GenBank, PubMed, or the like.

A. The Minigene

The minigene is composed of, at a minimum, a transgene and its regulatory sequences, and 5' and 3' AAV inverted terminal repeats (ITRs). In one desirable embodiment, the ITRs of AAV serotype 2 are used. However, ITRs from other suitable serotypes may be selected. It is this minigene which is packaged into a capsid protein and delivered to a selected host cell.

1. The transgene

The transgene is a nucleic acid sequence, heterologous to the vector sequences flanking the transgene, which encodes a polypeptide, protein, or other product, of interest. The nucleic acid coding sequence is operatively linked to regulatory components in a manner which permits transgene transcription, translation, and/or expression in a host cell.

The composition of the transgene sequence will depend upon the use to which the resulting vector will be put. For example, one type of transgene sequence includes a reporter sequence, which upon expression produces a detectable signal. Such reporter sequences include, without limitation, DNA sequences encoding β-lactamase, β-galactosidase (LacZ), alkaline phosphatase, thymidine kinase, green fluorescent protein (GFP), chloramphenicol acetyltransferase (CAT), luciferase, membrane bound proteins including, for example, CD2, CD4, CD8, the influenza hemagglutinin protein, and others well known in the art, to which high affinity antibodies directed thereto exist or can be produced by conventional means, and fusion proteins comprising a membrane bound protein appropriately fused to an antigen tag domain from, among others, hemagglutinin or Myc.

These coding sequences, when associated with regulatory elements which drive their expression, provide signals detectable by conventional means, including enzymatic, radiographic, colorimetric, fluorescence or other spectrographic assays, fluorescent activating cell sorting assays and immunological assays, including enzyme linked immunosorbent assay (ELISA), radioimmunoassay (RIA) and immunohistochemistry. For example, where the marker sequence is the LacZ gene, the presence of the vector carrying the signal is detected by assays for beta-galactosidase activity. Where the transgene is green fluorescent protein or luciferase, the vector carrying the signal may be measured visually by color or light production in a luminometer.

However, desirably, the transgene is a non-marker sequence encoding a product which is useful in biology and medicine, such as proteins, peptides, RNA, enzymes, dominant negative mutants, or catalytic RNAs. Desirable RNA molecules include tRNA, dsRNA, ribosomal RNA, catalytic RNAs, siRNA, small hairpin RNA, trans-splicing RNA, and antisense RNAs. One example of a useful RNA sequence is a sequence which inhibits or extinguishes expression of a targeted nucleic acid sequence in the treated animal. Typically, suitable target sequences in include oncologic targets and viral diseases. See, for examples of such targets the oncologic targets and viruses identified below in the section relating to immunogens.

The transgene may be used to correct or ameliorate gene deficiencies, which may include deficiencies in which normal genes are expressed at less than normal levels or deficiencies in which the functional gene product is not expressed. A preferred type of transgene sequence encodes a therapeutic protein or polypeptide which is expressed in a host cell. The invention further includes using multiple transgenes, e.g., to correct or ameliorate a gene defect caused by a multi-subunit protein. In certain situations, a different transgene may be used to encode each subunit of a protein, or to encode different peptides or proteins. This is desirable when the size of the DNA encoding the protein subunit is large, e.g., for an immunoglobulin, the platelet-derived growth factor, or a dystrophin protein. In order for the cell to produce the multi-subunit protein, a cell is infected with the recombinant virus containing each of the different subunits. Alternatively, different subunits of a protein may be encoded by the same transgene. In this case, a single transgene includes the DNA encoding each of the subunits, with the DNA for each subunit separated by an internal ribozyme entry site (IRES). This is desirable when the size of the DNA encoding each of the subunits is small, e.g., the total size of the DNA encoding the subunits and the IRES is less than five kilobases. As an alternative to an IRES, the DNA may be separated by sequences encoding a 2A peptide, which self-cleaves in a post-translational event. See, e.g., M. L. Donnelly, et al, *J. Gen. Virol.*, 78(Pt 1):13-21 (January 1997); Furler, S., et al, *Gene Ther.*, 8(11):864-873 (June 2001); Klump H., et al., *Gene Ther.*, 8(10):811-817 (May 2001). This 2A peptide is significantly smaller than an IRES, making it well suited for use when space is a limiting factor. More often, when the transgene is large, consists of multi-subunits, or two transgenes are co-delivered, rAAV carrying the desired transgene(s) or subunits are co-administered to allow them to concatamerize in vivo to form a single vector genome. In such an embodiment, a first AAV may carry an expression cassette which expresses a single transgene and a second AAV may carry an expression cassette which expresses a different transgene for co-expression in the host cell. However, the selected transgene may encode any biologically active product or other product, e.g., a product desirable for study.

Suitable transgenes may be readily selected by one of skill in the art. The selection of the transgene is not considered to be a limitation of this invention.

2. Regulatory Elements

In addition to the major elements identified above for the minigene, the vector also includes conventional control elements which are operably linked to the transgene in a manner which permits its transcription, translation and/or expression in a cell transfected with the plasmid vector or infected with the virus produced by the invention. As used herein, "operably linked" sequences include both expression control sequences that are contiguous with the gene of interest and expression control sequences that act in trans or at a distance to control the gene of interest.

Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A great number of expression control sequences, including promoters which are native, constitutive, inducible and/or tissue-specific, are known in the art and may be utilized.

Examples of constitutive promoters include, without limitation, the retroviral Rous sarcoma virus (RSV) LTR promoter (optionally with the RSV enhancer), the cytomegalovirus (CMV) promoter (optionally with the CMV enhancer) [see, e.g., Boshart et al, *Cell*, 41:521-530 (1985)], the SV40 promoter, the dihydrofolate reductase promoter, the β-actin promoter, the phosphoglycerol kinase (PGK) promoter, and the EF1 promoter [Invitrogen]. Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech and Ariad. Many other systems have been described and can be readily selected by one of skill in the art. Examples of inducible promoters regulated by exogenously supplied compounds, include, the zinc-inducible sheep metallothionine (MT) promoter, the dexamethasone (Dex)-inducible mouse mammary tumor virus (MMTV) promoter, the T7 polymerase promoter system [WO 98/10088]; the ecdysone insect promoter [No et al, Proc. Natl. Acad. Sci. USA, 93:3346-3351 (1996)], the tetracycline-repressible system [Gossen et al, Proc. Natl. Acad. Sci. USA, 89:5547-5551 (1992)], the tetracycline-inducible system [Gossen et al, Science, 268:1766-1769 (1995), see also Harvey et al, Curr. Opin. Chem. Biol., 2:512-518 (1998)], the RU486-inducible system [Wang et al, Nat. Biotech., 15:239-243 (1997) and Wang et al, Gene Ther., 4:432-441 (1997)] and the rapamycin-inducible system [Magari et al, J. Clin. Invest., 100:2865-2872 (1997)]. Other types of inducible promoters which may be useful in this context are those which are regulated by a specific physiological state, e.g., temperature, acute phase, a particular differentiation state of the cell, or in replicating cells only.

In another embodiment, the native promoter for the transgene will be used. The native promoter may be preferred when it is desired that expression of the transgene should mimic the native expression. The native promoter may be used when expression of the transgene must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic the native expression.

Another embodiment of the transgene includes a gene operably linked to a tissue-specific promoter. For instance, if expression in skeletal muscle is desired, a promoter active in muscle should be used. These include the promoters from genes encoding skeletal β-actin, myosin light chain 2A, dystrophin, muscle creatine kinase, as well as synthetic muscle promoters with activities higher than naturally-occurring promoters (see Li et al., Nat. Biotech., 17:241-245 (1999)). Examples of promoters that are tissue-specific are known for liver (albumin, Miyatake et al., J. Virol., 71:5124-32 (1997); hepatitis B virus core promoter, Sandig et al., Gene Ther., 3:1002-9 (1996); alpha-fetoprotein (AFP), Arbuthnot et al., Hum. Gene Ther., 7:1503-14 (1996)), bone osteocalcin (Stein et al., Mol. Biol. Rep., 24:185-96 (1997)); bone sialoprotein (Chen et al., J. Bone Miner. Res., 11:654-64 (1996)), lymphocytes (CD2, Hansal et al., J. Immunol., 161:1063-8 (1998); immunoglobulin heavy chain; T cell receptor chain), neuronal such as neuron-specific enolase (NSE) promoter (Andersen et al., Cell. Mol. Neurobiol., 13:503-15 (1993)), neurofilament light-chain gene (Piccioli et al., Proc. Natl. Acad. Sci. USA, 88:5611-5 (1991)), and the neuron-specific vgf gene (Piccioli et al., Neuron, 15:373-84 (1995)), among others.

Optionally, plasmids carrying therapeutically useful transgenes may also include selectable markers or reporter genes may include sequences encoding geneticin, hygromicin or purimycin resistance, among others. Such selectable reporters or marker genes (preferably located outside the viral genome to be rescued by the method of the invention) can be used to signal the presence of the plasmids in bacterial cells, such as ampicillin resistance. Other components of the plasmid may include an origin of replication. Selection of these and other promoters and vector elements are conventional and many such sequences are available [see, e.g., Sambrook et al, and references cited therein].

The combination of the transgene, promoter/enhancer, and 5' and 3' ITRs is referred to as a "minigene" for ease of reference herein. Provided with the teachings of this invention, the design of such a minigene can be made by resort to conventional techniques.

3. Delivery of the Minigene to a Packaging Host Cell

The minigene can be carried on any suitable vector, e.g., a plasmid, which is delivered to a host cell. The plasmids useful in this invention may be engineered such that they are suitable for replication and, optionally, integration in prokaryotic cells, mammalian cells, or both. These plasmids (or other vectors carrying the 5' AAV ITR-heterologous molecule-3'ITR) contain sequences permitting replication of the minigene in eukaryotes and/or prokaryotes and selection markers for these systems. Selectable markers or reporter genes may include sequences encoding geneticin, hygromicin or purimycin resistance, among others. The plasmids may also contain certain selectable reporters or marker genes that can be used to signal the presence of the vector in bacterial cells, such as ampicillin resistance. Other components of the plasmid may include an origin of replication and an amplicon, such as the amplicon system employing the Epstein Barr virus nuclear antigen. This amplicon system, or other similar amplicon components permit high copy episomal replication in the cells. Preferably, the molecule carrying the minigene is transfected into the cell, where it may exist transiently. Alternatively, the minigene (carrying the 5' AAV ITR-heterologous molecule-3' ITR) may be stably integrated into the genome of the host cell, either chromosomally or as an episome. In certain embodiments, the minigene may be present in multiple copies, optionally in head-to-head, head-to-tail, or tail-to-tail concatamers. Suitable transfection techniques are known and may readily be utilized to deliver the minigene to the host cell.

Generally, when delivering the vector comprising the minigene by transfection, the vector is delivered in an amount from about 5 µg to about 100 µg DNA, about 10 to about 50 µg DNA to about $1 \times 10^4$ cells to about $1 \times 10^{13}$ cells, or about $10^5$ cells. However, the relative amounts of vector DNA to host cells may be adjusted, taking into consideration such factors as the selected vector, the delivery method and the host cells selected.

B. Rep and Cap Sequences

In addition to the minigene, the host cell contains the sequences which drive expression of the AAV8 capsid protein (or a capsid protein comprising a fragment of the AAV8 capsid) in the host cell and rep sequences of the same serotype as the serotype of the AAV ITRs found in the minigene, or a cross-complementing serotype. The AAV cap and rep sequences may be independently obtained from an AAV source as described above and may be introduced into the host cell in any manner known to one in the art as described above. Additionally, when pseudotyping an AAV vector in an AAV8 capsid, the sequences encoding each of the essential rep proteins may be supplied by AAV8, or the sequences encoding the rep proteins may be supplied by different AAV serotypes (e.g., AAV1, AAV2, AAV3, AAV4, AAV5, AAV6, AAV7, AAV9). For example, the rep78/68 sequences may be from AAV2, whereas the rep52/40 sequences may be from AAV8.

In one embodiment, the host cell stably contains the capsid protein under the control of a suitable promoter, such as those described above. Most desirably, in this embodiment, the capsid protein is expressed under the control of an inducible promoter. In another embodiment, the capsid protein is supplied to the host cell in trans. When delivered to the host cell in trans, the capsid protein may be delivered via a plasmid which contains the sequences necessary to direct expression of the selected capsid protein in the host cell. Most desirably, when delivered to the host cell in trans, the plasmid carrying the capsid protein also carries other sequences required for packaging the rAAV, e.g., the rep sequences.

In another embodiment, the host cell stably contains the rep sequences under the control of a suitable promoter, such as those described above. Most desirably, in this embodiment, the essential rep proteins are expressed under the control of an inducible promoter. In another embodiment, the rep proteins are supplied to the host cell in trans. When delivered to the host cell in trans, the rep proteins may be delivered via a plasmid which contains the sequences necessary to direct expression of the selected rep proteins in the host cell. Most desirably, when delivered to the host cell in trans, the plasmid carrying the capsid protein also carries other sequences required for packaging the rAAV, e.g., the rep and cap sequences.

Thus, in one embodiment, the rep and cap sequences may be transfected into the host cell on a single nucleic acid molecule and exist stably in the cell as an episome. In another embodiment, the rep and cap sequences are stably integrated into the chromosome of the cell. Another embodiment has the rep and cap sequences transiently expressed in the host cell. For example, a useful nucleic acid molecule for such transfection comprises, from 5' to 3', a promoter, an optional spacer interposed between the promoter and the start site of the rep gene sequence, an AAV rep gene sequence, and an AAV cap gene sequence.

Optionally, the rep and/or cap sequences may be supplied on a vector that contains other DNA sequences that are to be introduced into the host cells. For instance, the vector may contain the rAAV construct comprising the minigene. The vector may comprise one or more of the genes encoding the helper functions, e.g., the adenoviral proteins E1, E2a, and E4ORF6, and the gene for VAI RNA.

Preferably, the promoter used in this construct may be any of the constitutive, inducible or native promoters known to one of skill in the art or as discussed above. In one embodiment, an AAV P5 promoter sequence is employed. The selection of the AAV to provide any of these sequences does not limit the invention.

In another preferred embodiment, the promoter for rep is an inducible promoter, such as are discussed above in connection with the transgene regulatory elements. One preferred promoter for rep expression is the T7 promoter. The vector comprising the rep gene regulated by the T7 promoter and the cap gene, is transfected or transformed into a cell which either constitutively or inducibly expresses the T7 polymerase. See WO 98/10088, published Mar. 12, 1998.

The spacer is an optional element in the design of the vector. The spacer is a DNA sequence interposed between the promoter and the rep gene ATG start site. The spacer may have any desired design; that is, it may be a random sequence of nucleotides, or alternatively, it may encode a gene product, such as a marker gene. The spacer may contain genes which typically incorporate start/stop and polyA sites. The spacer may be a non-coding DNA sequence from a prokaryote or eukaryote, a repetitive non-coding sequence, a coding sequence without transcriptional controls or a coding sequence with transcriptional controls. Two exemplary sources of spacer sequences are the phage ladder sequences or yeast ladder sequences, which are available commercially, e.g., from Gibco or Invitrogen, among others. The spacer may be of any size sufficient to reduce expression of the rep78 and rep68 gene products, leaving the rep52, rep40 and cap gene products expressed at normal levels. The length of the spacer may therefore range from about 10 bp to about 10.0 kbp, preferably in the range of about 100 bp to about 8.0 kbp. To reduce the possibility of recombination, the spacer is preferably less than 2 kbp in length; however, the invention is not so limited.

Although the molecule(s) providing rep and cap may exist in the host cell transiently (i.e., through transfection), it is preferred that one or both of the rep and cap proteins and the promoter(s) controlling their expression be stably expressed in the host cell, e.g., as an episome or by integration into the chromosome of the host cell. The methods employed for constructing embodiments of this invention are conventional genetic engineering or recombinant engineering techniques such as those described in the references above. While this specification provides illustrative examples of specific constructs, using the information provided herein, one of skill in the art may select and design other suitable constructs, using a choice of spacers, P5 promoters, and other elements, including at least one translational start and stop signal, and the optional addition of polyadenylation sites.

In another embodiment of this invention, the rep or cap protein may be provided stably by a host cell.

C. The Helper Functions

The packaging host cell also requires helper functions in order to package the rAAV of the invention. Optionally, these functions may be supplied by a herpesvirus. Most desirably, the necessary helper functions are each provided from a human or non-human primate adenovirus source, such as those described above and/or are available from a variety of sources, including the American Type Culture Collection (ATCC), Manassas, Va. (US). In one currently preferred embodiment, the host cell is provided with and/or contains an E1a gene product, an E1b gene product, an E2a gene product, and/or an E4 ORF6 gene product. The host cell may contain other adenoviral genes such as VAI RNA, but these genes are not required. In a preferred embodiment, no other adenovirus genes or gene functions are present in the host cell.

By "adenoviral DNA which expresses the E1a gene product", it is meant any adenovirus sequence encoding E1a or any functional E1a portion. Adenoviral DNA which expresses the E2a gene product and adenoviral DNA which expresses the E4 ORF6 gene products are defined similarly. Also included are any alleles or other modifications of the adenoviral gene or functional portion thereof. Such modifications may be deliberately introduced by resort to conventional genetic engineering or mutagenic techniques to enhance the adenoviral function in some manner, as well as naturally occurring allelic variants thereof. Such modifications and methods for manipulating DNA to achieve these adenovirus gene functions are known to those of skill in the art.

The adenovirus E1a, E1b, E2a, and/or E4ORF6 gene products, as well as any other desired helper functions, can be provided using any means that allows their expression in a cell. Each of the sequences encoding these products may be on a separate vector, or one or more genes may be on the same vector. The vector may be any vector known in the art or disclosed above, including plasmids, cosmids and viruses.

Introduction into the host cell of the vector may be achieved by any means known in the art or as disclosed above, including transfection, infection, electroporation, liposome delivery, membrane fusion techniques, high velocity DNA-coated pellets, viral infection and protoplast fusion, among others. One or more of the adenoviral genes may be stably integrated into the genome of the host cell, stably expressed as episomes, or expressed transiently. The gene products may all be expressed transiently, on an episome or stably integrated, or some of the gene products may be expressed stably while others are expressed transiently. Furthermore, the promoters for each of the adenoviral genes may be selected independently from a constitutive promoter, an inducible promoter or a native adenoviral promoter. The promoters may be regulated by a specific physiological state of the organism or cell (i.e., by the differentiation state or in replicating or quiescent cells) or by exogenously added factors, for example.

D. Host Cells And Packaging Cell Lines

The host cell itself may be selected from any biological organism, including prokaryotic (e.g., bacterial) cells, and eukaryotic cells, including, insect cells, yeast cells and mammalian cells. Particularly desirable host cells are selected from among any mammalian species, including, without limitation, cells such as A549, WEHI, 3T3, 10T1/2, BHK, MDCK, COS 1, COS 7, BSC 1, BSC 40, BMT 10, VERO, WI38, HeLa, 293 cells (which express functional adenoviral E1), Saos, C2C12, L cells, HT1080, HepG2 and primary fibroblast, hepatocyte and myoblast cells derived from mammals including human, monkey, mouse, rat, rabbit, and hamster. The selection of the mammalian species providing the cells is not a limitation of this invention; nor is the type of mammalian cell, i.e., fibroblast, hepatocyte, tumor cell, etc. The requirements for the cell used is that it not carry any adenovirus gene other than E1, E2a and/or E4 ORF6; it not contain any other virus gene which could result in homologous recombination of a contaminating virus during the production of rAAV; and it is capable of infection or transfection of DNA and expression of the transfected DNA. In a preferred embodiment, the host cell is one that has rep and cap stably transfected in the cell.

One host cell useful in the present invention is a host cell stably transformed with the sequences encoding rep and cap, and which is transfected with the adenovirus E1, E2a, and E4ORF6 DNA and a construct carrying the minigene as described above. Stable rep and/or cap expressing cell lines, such as B-50 (PCT/US98/19463), or those described in U.S. Pat. No. 5,658,785, may also be similarly employed. Another desirable host cell contains the minimum adenoviral DNA which is sufficient to express E4 ORF6. Yet other cell lines can be constructed using the AAV8 rep and/or AAV8 cap sequences of the invention.

The preparation of a host cell according to this invention involves techniques such as assembly of selected DNA sequences. This assembly may be accomplished utilizing conventional techniques. Such techniques include cDNA and genomic cloning, which are well known and are described in Sambrook et al., cited above, use of overlapping oligonucleotide sequences of the adenovirus and AAV genomes, combined with polymerase chain reaction, synthetic methods, and any other suitable methods which provide the desired nucleotide sequence.

Introduction of the molecules (as plasmids or viruses) into the host cell may also be accomplished using techniques known to the skilled artisan and as discussed throughout the specification. In preferred embodiment, standard transfection techniques are used, e.g., $CaPO_4$ transfection or electroporation, and/or infection by hybrid adenovirus/AAV vectors into cell lines such as the human embryonic kidney cell line HEK 293 (a human kidney cell line containing functional adenovirus E1 genes which provides trans-acting E1 proteins).

The AAV8 based vectors which are generated by one of skill in the art are beneficial for gene delivery to selected host cells and gene therapy patients since no neutralization antibodies to AAV8 have been found in the human population. One of skill in the art may readily prepare other rAAV viral vectors containing the AAV8 capsid proteins provided herein using a variety of techniques known to those of skill in the art. One may similarly prepare still other rAAV viral vectors containing AAV8 sequence and AAV capsids of another serotype.

One of skill in the art will readily understand that the AAV8 sequences of the invention can be readily adapted for use in these and other viral vector systems for in vitro, ex vivo or in vivo gene delivery. Similarly, one of skill in the art can readily select other fragments of the AAV8 genome of the invention for use in a variety of rAAV and non-rAAV vector systems. Such vectors systems may include, e.g., lentiviruses, retroviruses, poxviruses, vaccinia viruses, and adenoviral systems, among others. Selection of these vector systems is not a limitation of the present invention.

Thus, the invention further provides vectors generated using the nucleic acid and amino acid sequences of the novel AAV of the invention. Such vectors are useful for a variety of purposes, including for delivery of therapeutic molecules and for use in vaccine regimens. Particularly desirable for delivery of therapeutic molecules are recombinant AAV containing capsids of the novel AAV of the invention. These, or other vector constructs containing novel AAV sequences of the invention may be used in vaccine regimens, e.g., for co-delivery of a cytokine, or for delivery of the immunogen itself V. Recombinant Viruses And Uses Therefor Using the techniques described herein, one of skill in the art can generate a rAAV having a capsid of a serotype 8 of the invention or having a capsid containing one or more fragments of AAV8. In one embodiment, a full-length capsid from a single serotype, e.g., AAV8 [SEQ ID NO: 2] can be utilized. In another embodiment, a full-length capsid may be generated which contains one or more fragments of AAV8 fused in frame with sequences from another selected AAV serotype, or from heterologous portions of AAV8. For example, a rAAV may contain one or more of the novel hypervariable region sequences of AAV8. Alternatively, the unique AAV8 sequences of the invention may be used in constructs containing other viral or non-viral sequences. Optionally, a recombinant virus may carry AAV8 rep sequences encoding one or more of the AAV8 rep proteins.

A. Delivery of Viruses

In another aspect, the present invention provides a method for delivery of a transgene to a host which involves transfecting or infecting a selected host cell with a recombinant viral vector generated with the AAV8 sequences (or functional fragments thereof) of the invention. Methods for delivery are well known to those of skill in the art and are not a limitation of the present invention.

In one desirable embodiment, the invention provides a method for AAV8 mediated delivery of a transgene to a host. This method involves transfecting or infecting a selected host cell with a recombinant viral vector containing a selected transgene under the control of sequences which direct expression thereof and AAV8 capsid proteins.

Optionally, a sample from the host may be first assayed for the presence of antibodies to a selected AAV serotype. A variety of assay formats for detecting neutralizing antibodies are well known to those of skill in the art. The selection of such an assay is not a limitation of the present invention. See, e.g., Fisher et al, *Nature Med.*, 3(3):306-312 (March 1997) and W C Manning et al, *Human Gene Therapy*, 9:477-485 (Mar. 1, 1998). The results of this assay may be used to determine which AAV vector containing capsid proteins of a particular serotype are preferred for delivery, e.g., by the absence of neutralizing antibodies specific for that capsid serotype.

In one aspect of this method, the delivery of vector with AAV8 capsid proteins may precede or follow delivery of a gene via a vector with a different serotype AAV capsid protein. Thus, gene delivery via rAAV vectors may be used for repeat gene delivery to a selected host cell. Desirably, subsequently administered rAAV vectors carry the same transgene as the first rAAV vector, but the subsequently administered vectors contain capsid proteins of serotypes which differ from the first vector. For example, if a first vector has AAV8 capsid proteins, subsequently administered vectors may have capsid proteins selected from among the other serotypes.

Optionally, multiple rAAV8 vectors can be used to deliver large transgenes or multiple transgenes by co-administration of rAAV vectors concatamerize in vivo to form a single vector genome. In such an embodiment, a first AAV may carry an expression cassette which expresses a single transgene (or a subunit thereof) and a second AAV may carry an expression cassette which expresses a second transgene (or a different subunit) for co-expression in the host cell. A first AAV may carry an expression cassette which is a first piece of a polycistronic construct (e.g., a promoter and transgene, or subunit) and a second AAV may carry an expression cassette which is a second piece of a polycistronic construct (e.g., transgene or subunit and a polyA sequence). These two pieces of a polycistronic construct concatamerize in vivo to form a single vector genome which co-expresses the transgenes delivered by the first and second AAV. In such embodiments, the rAAV vector carrying the first expression cassette and the rAAV vector carrying the second expression cassette can be delivered in a single pharmaceutical composition. In other embodiments, the two or more rAAV vectors are delivered as separate pharmaceutical compositions which can be administered substantially simultaneously, or shortly before or after one another.

The above-described recombinant vectors may be delivered to host cells according to published methods. The rAAV, preferably suspended in a physiologically compatible carrier, may be administered to a human or non-human mammalian patient. Suitable carriers may be readily selected by one of skill in the art in view of the indication for which the transfer virus is directed. For example, one suitable carrier includes saline, which may be formulated with a variety of buffering solutions (e.g., phosphate buffered saline). Other exemplary carriers include sterile saline, lactose, sucrose, calcium phosphate, gelatin, dextran, agar, pectin, peanut oil, sesame oil, and water. The selection of the carrier is not a limitation of the present invention.

Optionally, the compositions of the invention may contain, in addition to the rAAV and carrier(s), other conventional pharmaceutical ingredients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin The vectors are administered in sufficient amounts to transfect the cells and to provide sufficient levels of gene transfer and expression to provide a therapeutic benefit without undue adverse effects, or with medically acceptable physiological effects, which can be determined by those skilled in the medical arts. Conventional and pharmaceutically acceptable routes of administration include, but are not limited to, direct delivery to a desired organ (e.g., the liver (optionally via the hepatic artery) or lung), oral, inhalation, intranasal, intratracheal, intraarterial, intraocular, intravenous, intramuscular, subcutaneous, intradermal, and other parental routes of administration. Routes of administration may be combined, if desired.

Dosages of the viral vector will depend primarily on factors such as the condition being treated, the age, weight and health of the patient, and may thus vary among patients. For example, a therapeutically effective human dosage of the viral vector is generally in the range of from about 0.1 ml to about 100 ml of solution containing concentrations of from about $1\times10^9$ to $1\times10^{16}$ genomes virus vector. A preferred human dosage for delivery to large organs (e.g., liver, muscle, heart and lung) may be about $5\times10^{10}$ to $5\times10^{13}$ AAV genomes per 1 kg, at a volume of about 1 to 100 mL. A preferred dosage for delivery to eye is about $5\times10^9$ to $5\times10^{12}$ genome copies, at a volume of about 0.1 mL to 1 mL. The dosage will be adjusted to balance the therapeutic benefit against any side effects and such dosages may vary depending upon the therapeutic application for which the recombinant vector is employed. The levels of expression of the transgene can be monitored to determine the frequency of dosage resulting in viral vectors, preferably AAV vectors containing the minigene. Optionally, dosage regimens similar to those described for therapeutic purposes may be utilized for immunization using the compositions of the invention.

Examples of therapeutic products and immunogenic products for delivery by the AAV8-containing vectors of the invention are provided below. These vectors may be used for a variety of therapeutic or vaccinal regimens, as described herein. Additionally, these vectors may be delivered in combination with one or more other vectors or active ingredients in a desired therapeutic and/or vaccinal regimen.

B. Therapeutic Transgenes

Useful therapeutic products encoded by the transgene include hormones and growth and differentiation factors including, without limitation, insulin, glucagon, growth hormone (GH), parathyroid hormone (PTH), growth hormone releasing factor (GRF), follicle stimulating hormone (FSH), luteinizing hormone (LH), human chorionic gonadotropin (hCG), vascular endothelial growth factor (VEGF), angiopoietins, angiostatin, granulocyte colony stimulating factor (GCSF), erythropoietin (EPO), connective tissue growth factor (CTGF), basic fibroblast growth factor (bFGF), acidic fibroblast growth factor (aFGF), epidermal growth factor (EGF), platelet-derived growth factor (PDGF), insulin growth factors I and II (IGF-I and IGF-II), any one of the transforming growth factor α superfamily, including TGFα, activins, inhibins, or any of the bone morphogenic proteins (BMP) BMPs 1-15, any one of the heregluin/neuregulin/ARIA/neu differentiation factor (NDF) family of growth factors, nerve growth factor (NGF), brain-derived neurotrophic factor (BDNF), neurotrophins NT-3 and NT-4/5, ciliary neurotrophic factor (CNTF), glial cell line derived neurotrophic factor (GDNF), neurturin, agrin, any one of the family of semaphorins/collapsins, netrin-1 and netrin-2, hepatocyte growth factor (HGF), ephrins, noggin, sonic hedgehog and tyrosine hydroxylase.

Other useful transgene products include proteins that regulate the immune system including, without limitation, cytokines and lymphokines such as thrombopoietin (TPO), interleukins (IL) IL-1 through IL-25 (including IL-2, IL-4, IL-12 and IL-18), monocyte chemoattractant protein, leukemia inhibitory factor, granulocyte-macrophage colony stimulating factor, Fas ligand, tumor necrosis factors α and β, interferons α, β, and γ, stem cell factor, flk-2/flt3 ligand. Gene products produced by the immune system are also useful in the invention. These include, without limitations, immunoglobulins IgG, IgM, IgA, IgD and IgE, chimeric immunoglobulins, humanized antibodies, single chain antibodies, T cell receptors, chimeric T cell receptors, single chain T cell receptors, class I and class II MHC molecules, as well as engineered immunoglobulins and MHC molecules. Useful gene products also include complement regulatory proteins such as complement regulatory proteins, membrane cofactor protein (MCP), decay accelerating factor (DAF), CR1, CF2 and CD59.

Still other useful gene products include any one of the receptors for the hormones, growth factors, cytokines, lymphokines, regulatory proteins and immune system proteins. The invention encompasses receptors for cholesterol regulation and/or lipid modulation, including the low density lipoprotein (LDL) receptor, high density lipoprotein (HDL) receptor, the very low density lipoprotein (VLDL) receptor, and scavenger receptors. The invention also encompasses gene products such as members of the steroid hormone receptor superfamily including glucocorticoid receptors and estrogen receptors, Vitamin D receptors and other nuclear receptors. In addition, useful gene products include transcription factors such as jun, fos, max, mad, serum response factor (SRF), AP-1, AP2, myb, MyoD and myogenin, ETS-box containing proteins, TFE3, E2F, ATF1, ATF2, ATF3, ATF4, ZF5, NFAT, CREB, HNF-4, C/EBP, SP1, CCAAT-box binding proteins, interferon regulation factor (IRF-1), Wilms tumor protein, ETS-binding protein, STAT, GATA-box binding proteins, e.g., GATA-3, and the forkhead family of winged helix proteins.

Other useful gene products include, carbamoyl synthetase I, ornithine transcarbamylase, arginosuccinate synthetase, arginosuccinate lyase, arginase, fumarylacetacetate hydrolase, phenylalanine hydroxylase, alpha-1 antitrypsin, glucose-6-phosphatase, porphobilinogen deaminase, cystathione beta-synthase, branched chain ketoacid decarboxylase, albumin, isovaleryl-coA dehydrogenase, propionyl CoA carboxylase, methyl malonyl CoA mutase, glutaryl CoA dehydrogenase, insulin, beta-glucosidase, pyruvate carboxylate, hepatic phosphorylase, phosphorylase kinase, glycine decarboxylase, H-protein, T-protein, a cystic fibrosis transmembrane regulator (CFTR) sequence, and a dystrophin cDNA sequence. Still other useful gene products include enzymes such as may be useful in enzyme replacement therapy, which is useful in a variety of conditions resulting from deficient activity of enzyme. For example, enzymes that contain mannose-6-phosphate may be utilized in therapies for lysosomal storage diseases (e.g., a suitable gene includes that encoding β-glucuronidase (GUSB)).

Still other useful gene products include those used for treatment of hemophilia, including hemophilia B (including Factor IX) and hemophilia A (including Factor VIII and its variants, such as the light chain and heavy chain of the heterodimer and the B-deleted domain; U.S. Pat. Nos. 6,200,560 and 6,221,349). The Factor VIII gene codes for 2351 amino acids and the protein has six domains, designated from the amino to the terminal carboxy terminus as A1-A2-B-A3-C1-C2 [Wood et al, Nature, 312:330 (1984); Vehar et al., Nature 312:337 (1984); and Toole et al, Nature, 342:337 (1984)]. Human Factor VIII is processed within the cell to yield a heterodimer primarily comprising a heavy chain containing the A1, A2 and B domains and a light chain containing the A3, C1 and C2 domains. Both the single chain polypeptide and the heterodimer circulate in the plasma as inactive precursors, until activated by thrombin cleavage between the A2 and B domains, which releases the B domain and results in a heavy chain consisting of the A1 and A2 domains. The B domain is deleted in the activated procoagulant form of the protein. Additionally, in the native protein, two polypeptide chains ("a" and "b"), flanking the B domain, are bound to a divalent calcium cation.

In some embodiments, the minigene comprises first 57 base pairs of the Factor VIII heavy chain which encodes the 10 amino acid signal sequence, as well as the human growth hormone (hGH) polyadenylation sequence. In alternative embodiments, the minigene further comprises the A1 and A2 domains, as well as 5 amino acids from the N-terminus of the B domain, and/or 85 amino acids of the C-terminus of the B domain, as well as the A3, C1 and C2 domains. In yet other embodiments, the nucleic acids encoding Factor VIII heavy chain and light chain are provided in a single minigene separated by 42 nucleic acids coding for 14 amino acids of the B domain [U.S. Pat. No. 6,200,560].

As used herein, a therapeutically effective amount is an amount of AAV vector that produces sufficient amounts of Factor VIII to decrease the time it takes for a subject's blood to clot. Generally, severe hemophiliacs having less than 1% of normal levels of Factor VIII have a whole blood clotting time of greater than 60 minutes as compared to approximately 10 minutes for non-hemophiliacs.

The present invention is not limited to any specific Factor VIII sequence. Many natural and recombinant forms of Factor VIII have been isolated and generated. Examples of naturally occurring and recombinant forms of Factor VII can be found in the patent and scientific literature including, U.S. Pat. Nos. 5,563,045, 5,451,521, 5,422,260, 5,004,803, 4,757,006, 5,661,008, 5,789,203, 5,595,886, 5,045,455, 5,668,108, 5,633,150, 5,693,499, 5,587,310, 5,171,844, 5,149,637, 5,112,950, 4,886,876, WO 94/11503, WO 87/07144, WO 92/16557, WO 91/09122, WO 97/03195, WO 96/21035, WO 91/07490, EP 0 672 138, EP 0 270 618, EP 0 182 448, EP 0 162 067, EP 0 786 474, EP 0 533 862, EP 0 506 757, EP 0 874 057, EP 0 795 021, EP 0 670 332, EP 0 500 734, EP 0 232 112, EP 0 160 457, Sanberg et al., XXth Int. Congress of the World Fed. Of Hemophilia (1992), and Lind et al., *Eur. J. Biochem.*, 232:19 (1995).

Nucleic acids sequences coding for the above-described Factor VIII can be obtained using recombinant methods or by deriving the sequence from a vector known to include the same. Furthermore, the desired sequence can be isolated directly from cells and tissues containing the same, using standard techniques, such as phenol extraction and PCR of cDNA or genomic DNA [See, e.g., Sambrook et al]. Nucleotide sequences can also be produced synthetically, rather than cloned. The complete sequence can be assembled from overlapping oligonucleotides prepared by standard methods and assembled into a complete coding sequence [See, e.g., Edge, *Nature* 292:757 (1981); Nambari et al, *Science,* 223: 1299 (1984); and Jay et al, *J. Biol. Chem.* 259:6311 (1984).

Furthermore, the invention is not limited to human Factor VIII. Indeed, it is intended that the present invention encompass Factor VIII from animals other than humans, including but not limited to companion animals (e.g., canine, felines, and equines), livestock (e.g., bovines, caprines and ovines), laboratory animals, marine mammals, large cats, etc.

The AAV vectors may contain a nucleic acid coding for fragments of Factor VIII which is itself not biologically active, yet when administered into the subject improves or restores the blood clotting time. For example, as discussed above, the Factor VIII protein comprises two polypeptide chains: a heavy chain and a light chain separated by a B-domain which is cleaved during processing. As demonstrated by the present invention, co-transducing recipient cells with the Factor VIII heavy and light chains leads to the expression of biologically active Factor VIII. Because, however, most hemophiliacs contain a mutation or deletion in only one of the chain (e.g., heavy or light chain), it may be possible to administer only the chain defective in the patient to supply the other chain.

Other useful gene products include non-naturally occurring polypeptides, such as chimeric or hybrid polypeptides having a non-naturally occurring amino acid sequence containing insertions, deletions or amino acid substitutions. For example, single-chain engineered immunoglobulins could be useful in certain immunocompromised patients. Other types of non-naturally occurring gene sequences include antisense molecules and catalytic nucleic acids, such as ribozymes, which could be used to reduce overexpression of a target.

Reduction and/or modulation of expression of a gene is particularly desirable for treatment of hyperproliferative conditions characterized by hyperproliferating cells, as are cancers and psoriasis. Target polypeptides include those polypeptides which are produced exclusively or at higher levels in hyperproliferative cells as compared to normal cells. Target antigens include polypeptides encoded by oncogenes such as myb, myc, fyn, and the translocation gene bcr/abl, ras, src, P53, neu, trk and EGRF. In addition to oncogene products as target antigens, target polypeptides for anti-cancer treatments and protective regimens include variable regions of antibodies made by B cell lymphomas and variable regions of T cell receptors of T cell lymphomas which, in some embodiments, are also used as target antigens for autoimmune disease. Other tumor-associated polypeptides can be used as target polypeptides such as polypeptides which are found at higher levels in tumor cells including the polypeptide recognized by monoclonal antibody 17-1A and folate binding polypeptides.

Other suitable therapeutic polypeptides and proteins include those which may be useful for treating individuals suffering from autoimmune diseases and disorders by conferring a broad based protective immune response against targets that are associated with autoimmunity including cell receptors and cells which produce "self"-directed antibodies. T cell mediated autoimmune diseases include Rheumatoid arthritis (RA), multiple sclerosis (MS), Sjögren's syndrome, sarcoidosis, insulin dependent diabetes mellitus (IDDM), autoimmune thyroiditis, reactive arthritis, ankylosing spondylitis, scleroderma, polymyositis, dermatomyositis, psoriasis, vasculitis, Wegener's granulomatosis, Crohn's disease and ulcerative colitis. Each of these diseases is characterized by T cell receptors (TCRs) that bind to endogenous antigens and initiate the inflammatory cascade associated with autoimmune diseases.

C. Immunogenic Transgenes

Suitably, the AAV8 vectors of the invention avoid the generation of immune responses to the AAV8 sequences contained within the vector. However, these vectors may nonetheless be formulated in a manner which permits the expression of a transgene carried by the vectors to induce an immune response to a selected antigen. For example, in order to promote an immune response, the transgene may be expressed from a constitutive promoter, the vector can be adjuvanted as described herein, and/or the vector can be put into degenerating tissue.

Examples of suitable immunogenic transgenes include those selected from a variety of viral families. Example of desirable viral families against which an immune response would be desirable include, the picornavirus family, which includes the genera rhinoviruses, which are responsible for about 50% of cases of the common cold; the genera enteroviruses, which include polioviruses, coxsackieviruses, echoviruses, and human enteroviruses such as hepatitis A virus; and the genera apthoviruses, which are responsible for foot and mouth diseases, primarily in non-human animals. Within the picornavirus family of viruses, target antigens include the VP1, VP2, VP3, VP4, and VPG. Other viral families include the astroviruses and the calcivirus family. The calcivirus family encompasses the Norwalk group of viruses, which are an important causative agent of epidemic gastroenteritis. Still another viral family desirable for use in targeting antigens for inducing immune responses in humans and non-human animals is the togavirus family, which includes the genera alphavirus, which include Sindbis viruses, RossRiver virus, and Venezuelan, Eastern & Western Equine encephalitis, and rubivirus, including Rubella virus. The flaviviridae family includes dengue, yellow fever, Japanese encephalitis, St. Louis encephalitis and tick borne encephalitis viruses. Other target antigens may be generated from the Hepatitis C or the coronavirus family, which includes a number of non-human viruses such as infectious bronchitis virus (poultry), porcine transmissible gastroenteric virus (pig), porcine hemagglutinatin encephalomyelitis virus (pig), feline infectious peritonitis virus (cats), feline enteric coronavirus (cat), canine coronavirus (dog), and human respiratory coronaviruses, which may cause the common cold and/or non-A, B or C hepatitis, and which include the putative cause of sudden acute respiratory syndrome (SARS). Within the coronavirus family, target antigens include the E1 (also called M or matrix protein), E2 (also called S or Spike protein), E3 (also called HE or hemagglutin-elterose) glycoprotein (not present in all coronaviruses), or N (nucleocapsid). Still other antigens may be targeted against the arterivirus family and the rhabdovirus family. The rhabdovirus family includes the genera vesiculovirus (e.g., Vesicular Stomatitis Virus), and the general lyssavirus (e.g., rabies). Within the rhabdovirus family, suitable antigens may be derived from the G protein or the N protein. The family filoviridae, which includes hemorrhagic fever viruses such as Marburg and Ebola virus may be a suitable source of antigens. The paramyxovirus family includes parainfluenza Virus Type 1, parainfluenza Virus Type 3, bovine parainfluenza Virus Type 3, rubulavirus (mumps virus, parainfluenza Virus Type 2, parainfluenza virus Type 4, Newcastle disease virus (chickens), rinderpest, morbillivirus, which includes measles and canine distemper, and pneumovirus, which includes respiratory syncytial virus. The influenza virus is classified within the family orthomyxovirus and is a suitable source of antigen (e.g., the HA protein, the N1 protein). The bunyavirus family includes the genera bunyavirus (California encephalitis, La Crosse), phlebovirus (Rift Valley Fever), hantavirus (puremala is a hemahagin fever virus), nairovirus (Nairobi sheep disease) and various unassigned bungaviruses. The arenavirus family provides a source of antigens against LCM and Lassa fever virus. Another source of antigens is the bornavirus family. The reovirus family includes the genera reovirus, rotavirus (which causes acute gastroenteritis in children), orbiviruses, and cultivirus (Colorado Tick fever, Lebombo (humans), equine encephalosis, blue tongue). The retrovirus family includes the sub-family oncorivirinal which encompasses such human and veterinary diseases as feline leukemia virus, HTLVI and HTLVII, lentivirinal (which includes HIV, simian immunodeficiency virus, feline immunodeficiency virus, equine infectious anemia virus, and spumavirinal). The papovavirus family includes the sub-family polyomaviruses (BKU and JCU viruses) and the sub-family papillomavirus (associated with cancers or malignant progression of papilloma). The adenovirus family includes viruses (EX, AD7, ARD, O.B.) which cause respiratory disease and/or enteritis. The parvovirus family feline parvovirus (feline enteritis), feline panleucopeniavirus, canine parvovirus, and porcine parvovirus. The herpesvirus family includes the sub-family alphaherpesvirinae, which encompasses the genera simplexvirus (HSVI, HSVII), varicellovirus (pseudorabies, varicella zoster) and the sub-family betaherpesvirinae, which includes the genera cytomegalovirus (HCMV, muromegalovirus) and the sub-family gammaherpesvirinae, which includes the genera lymphocryptovirus, EBV (Burkitts lymphoma), human herpesviruses 6A, 6B and 7, Kaposi's sarcoma-associated herpesvirus and cercopithecine herpesvirus (B virus), infectious rhinotracheitis, Marek's disease virus, and rhadinovirus. The poxvirus family includes the sub-family chordopoxvirinae, which encompasses the genera orthopoxvirus (Variola major (Smallpox) and Vaccinia (Cowpox)), parapoxvirus, avipoxvirus, capripoxvirus, leporipoxvirus, suipoxvirus, and the sub-family entomopoxvirinae. The hepadnavirus family includes the Hepatitis B virus. One unclassified virus which may be suitable source of antigens is the Hepatitis delta virus, Hepatitis E virus, and prions. Another virus which is a source of antigens is Nipan Virus. Still other viral sources may include avian infectious bursal disease virus and porcine respiratory and reproductive syndrome virus. The alphavirus family includes equine arteritis virus and various Encephalitis viruses.

The present invention may also encompass immunogens which are useful to immunize a human or non-human animal against other pathogens including bacteria, fungi, parasitic microorganisms or multicellular parasites which infect human and non-human vertebrates, or from a cancer cell or tumor cell. Examples of bacterial pathogens include pathogenic gram-positive cocci include *pneumococci; staphylococci* (and the toxins produced thereby, e.g., enterotoxin B); and *streptococci*. Pathogenic gram-negative cocci include meningococcus; gonococcus. Pathogenic enteric gram-negative bacilli include enterobacteriaceae; pseudomonas, acinetobacteria and eikenella; melioidosis; salmonella; shigella; haemophilus; moraxella; *H. ducreyi* (which causes chancroid); brucella species (brucellosis); *Francisella tularensis* (which causes tularemia); *Yersinia pestis* (plague) and other *Yersinia* (pasteurella); streptobacillus moniliformis and spirillum; Gram-positive bacilli include listeria monocytogenes; erysipelothrix rhusiopathiae; *Corynebacterium diphtheria* (diphtheria); cholera; *B. anthracis* (anthrax); donovanosis (granuloma inguinale); and bartonellosis. Diseases caused by pathogenic anaerobic bacteria include tetanus; botulism (*Clostridum botulinum* and its toxin); *Clostridium perfringens* and its epsilon toxin; other clostridia; tuberculosis; leprosy; and other mycobacteria. Pathogenic spirochetal diseases include syphilis; treponematoses: yaws, pinta and endemic syphilis; and leptospirosis. Other infections caused by higher pathogen bacteria and pathogenic fungi include glanders (*Burkholderia mallei*); actinomycosis; nocardiosis; cryptococcosis, blastomycosis, histoplasmosis and coccidioidomycosis; candidiasis, aspergillosis, and mucormycosis; sporotrichosis; paracoccidiodomycosis, petriellidiosis, torulopsosis, mycetoma and chromomycosis; and dermatophytosis. Rickettsial infections include Typhus fever, Rocky Mountain spotted fever, Q fever (*Coxiella burnetti*), and Rickettsialpox. Examples of mycoplasma and chlamydial infections include: mycoplasma pneumoniae; lymphogranuloma venereum; psittacosis; and perinatal chlamydial infections. Pathogenic eukaryotes encompass pathogenic protozoans and helminths and infections produced thereby include: amebiasis; malaria; leishmaniasis; trypanosomiasis; toxoplasmosis; *Pneumocystis carinii; Trichans; Toxoplasma gondii*; babesiosis; giardiasis; trichinosis; filariasis; schistosomiasis; nematodes; trematodes or flukes; and cestode (tapeworm) infections.

Many of these organisms and/or the toxins produced thereby have been identified by the Centers for Disease Control [(CDC), Depaitment of Heath and Human Services, USA], as agents which have potential for use in biological attacks. For example, some of these biological agents, include, *Bacillus anthracis* (anthrax), *Clostridium botulinum* and its toxin (botulism), *Yersinia pestis* (plague), variola major (smallpox), *Francisella tularensis* (tularemia), and viral hemorrhagic fevers [filoviruses (e.g., Ebola, Marburg], and arenaviruses [e.g., Lassa, Machupo]), all of which are currently classified as Category A agents; *Coxiella burnetti* (Q fever); Brucella species (brucellosis), *Burkholderia mallei* (glanders), *Burkholderia pseudomallei* (meloidosis), *Ricinus communis* and its toxin (ricin toxin), *Clostridium perfringens* and its toxin (epsilon toxin), *Staphylococcus* species and their toxins (enterotoxin B), *Chlamydia psittaci* (psittacosis), water safety threats (e.g., *Vibrio cholerae, Crytosporidium parvum*), Typhus fever (*Richettsia powazekii*), and viral encephalitis (alphaviruses, e.g., Venezuelan equine encephalitis; eastern equine encephalitis; western equine encephalitis); all of which are currently classified as Category B agents; and Nipan virus and hantaviruses, which are currently classified as Category C agents. In addition, other organisms, which are so classified or differently classified, may be identified and/or used for such a purpose in the future. It will be readily understood that the viral vectors and other constructs described herein are useful to deliver antigens from these organisms, viruses, their toxins or other by-products, which will prevent and/or treat infection or other adverse reactions with these biological agents.

Administration of the vectors of the invention to deliver immunogens against the variable region of the T cells elicit an immune response including CTLs to eliminate those T cells. In rheumatoid arthritis (RA), several specific variable regions of TCRs which are involved in the disease have been characterized. These TCRs include V-3, V-14, V-17 and V-17. Thus, delivery of a nucleic acid sequence that encodes at least one of these polypeptides will elicit an immune response that will target T cells involved in RA. In multiple sclerosis (MS), several specific variable regions of TCRs which are involved in the disease have been characterized. These TCRs include V-7 and V-10. Thus, delivery of a nucleic acid sequence that encodes at least one of these polypeptides will elicit an immune response that will target T cells involved in MS. In scleroderma, several specific variable regions of TCRs which are involved in the disease have been characterized. These TCRs include V-6, V-8, V-14 and V-16, V-3C, V-7, V-14, V-15, V-16, V-28 and V-12. Thus, delivery of a nucleic acid molecule that encodes at least one of these polypeptides will elicit an immune response that will target T cells involved in scleroderma.

Thus, a rAAV8-derived recombinant viral vector of the invention provides an efficient gene transfer vehicle which can deliver a selected transgene to a selected host cell in vivo or ex vivo even where the organism has neutralizing antibodies to one or more AAV serotypes. In one embodiment, the rAAV and the cells are mixed ex vivo; the infected cells are cultured using conventional methodologies; and the transduced cells are re-infused into the patient.

These compositions are particularly well suited to gene delivery for therapeutic purposes and for immunization, including inducing protective immunity. Further, the compositions of the invention may also be used for production of a desired gene product in vitro. For in vitro production, a desired product (e.g., a protein) may be obtained from a desired culture following transfection of host cells with a rAAV containing the molecule encoding the desired product and culturing the cell culture under conditions which permit expression. The expressed product may then be purified and isolated, as desired. Suitable techniques for transfection, cell culturing, purification, and isolation are known to those of skill in the art.

The following examples illustrate several aspects and embodiments of the invention.

Example 1: Production of Recombinant AAV8 Viral Genomes Equipped with AAV2 ITRs Chimeric packaging constructs are generated by fusing AAV2 rep with cap sequences of novel AAV serotypes. These chimeric packaging constructs are used, initially, for pseudotyping recombinant AAV genomes carrying AAV2 ITRs by triple transfection in 293 cell using Ad5 helper plasmid. These pseudotyped vectors are used to evaluate performance in transduction-based serological studies and evaluate gene transfer efficiency of novel AAV serotypes in different animal models including NHP and rodents, before intact and infectious viruses of these novel serotypes are isolated.

A. pAAV2GFP

The AAV2 plasmid which contains the AAV2 ITRs and green fluorescent protein expressed under the control of a constitutive promoter. This plasmid contains the following elements: the AAV2 ITRs, a CMV promoter and the GFP coding sequences.

B. Cloning of Trans Plasmid

To construct the chimeric trans-plasmid for production of recombinant pseudotyped AAV8 vectors, p5E18 plasmid (Xiao et al., 1999, *J. Virol* 73:3994-4003) was partially digested with Xho I to linearize the plasmid at the Xho I site at the position of 3169 bp only. The Xho I cut ends were then filled in and ligated back. This modified p5E18 plasmid was restricted with Xba I and Xho I in a complete digestion to remove the AAV2 cap gene sequence and replaced with a 2267 bp Spe I/Xho I fragment containing the AAV8 cap gene which was isolated from pCRAAV8 6-5+15-4 plasmid.

The resulting plasmid contains the AAV2 rep sequences for Rep78/68 under the control of the AAV2 P5 promoter, and the AAV2 rep sequences for Rep52/40 under the control of the AAV2 P19 promoter. The AAV9 capsid sequences are under the control of the AAV2 P40 promoter, which is located within the Rep sequences. This plasmid further contains a spacer 5' of the rep ORF.

Alternatively, a similar plasmid can be constructed which utilizes the AAV8 rep sequences and the native AAV8 promoter sequences. This plasmid is then used for production of rAAV8, as described herein.

C. Production of Pseudotyped rAAV

The rAAV particles (AAV2 vector in AAV8 capsid) are generated using an adenovirus-free method. Briefly, the cis plasmid (pAAV2.1 lacZ plasmid containing AAV2 ITRs), and the trans plasmid pCRAAV8 6-5+15-4 (containing the AAV2 rep and AAV8cap) and a helper plasmid, respectively, were simultaneously co-transfected into 293 cells in a ratio of 1:1:2 by calcium phosphate precipitation.

For the construction of the pAd helper plasmids, pBG10 plasmid was purchased from Microbix (Canada). A RsrII fragment containing L2 and L3 was deleted from pBHG10, resulting in the first helper plasmid, pAdΔ F13. Plasmid Ad F1 was constructed by cloning Asp700/SalI fragment with a PmeI/SgfI deletion, isolating from pBHG10, into Bluescript. MLP, L2, L2 and L3 were deleted in the pAdΔF1. Further deletions of a 2.3 kb NruI fragment and, subsequently, a 0.5 kb RsrII/NruI fragment generated helper plasmids pAdΔF5 and pAdΔF6, respectively. The helper plasmid, termed pΔF6, provides the essential helper functions of E2a and E4 ORF6 not provided by the E1-expressing helper cell, but is deleted of adenoviral capsid proteins and functional E1 regions).

Typically, 50 μg of DNA (cis:trans:helper) was transfected onto a 150 mm tissue culture dish. The 293 cells were harvested 72 hours post-transfection, sonicated and treated with 0.5% sodium deoxycholate (37° C. for 10 min.) Cell lysates were then subjected to two rounds of a CsCl gradient. Peak fractions containing rAAV vector are collected, pooled and dialyzed against PBS.

Example 2: Evaluation of Vectors with AAV8 Capsids

Vectors based on AAV1 (2/1), AAV5 (2/5) and AAV2 (2/2) were developed essentially as described for AAV8 in Example 1. Genome copy (GC) titers of AAV vectors were determined by TaqMan analysis using probes and primers targeting SV40 poly A region as described previously [Gao, G., et al., (2000) *Hum Gene Ther* 11, 2079-91]. Recombinant virions were recovered by $CsCl_2$ sedimentation in all cases except AAV2/2, which was purified by heparin chromatography.

Vectors were constructed for each serotype for a number of in vitro and in vivo studies. Eight different transgene cassettes were incorporated into the vectors and recombinant virions were produced for each serotype. The recovery of virus, based on genome copies, is summarized in Table 1. The yields of vector were high for each serotype with no consistent differences between serotypes. Data presented in the table are average genome copy yields with standard deviation $\times 10^{13}$ of multiple production lots of 50 plate (150 mm) transfections.

TABLE 1

Production of Recombinant Vectors

|  | AAV2/1 | AAV2/2 | AAV2/5 | AAV2/8 |
| --- | --- | --- | --- | --- |
| CMV LacZ | 7.30 ± 4.33 (n = 9) | 4.49 ± 2.89 (n = 6) | 5.19 ± 5.19 (n = 8) | 0.87 (n = 1) |
| CMV EGFP | 6.43 ± 2.42 (n = 2) | 3.39 ± 2.42 (n = 2) | 5.55 ± 6.49 (n = 4) | 3.74 ± 3.88 (n = 2) |
| TBG LacZ | 4.18 (n = 1) | 0.23 (n = 1) | 0.704 ± 0.43 (n = 2) | 0.532 (n = 1) |
| Alb A1AT | 4.67 ± 0.75 (n = 2) | 4.77 (n = 1) | 4.09 (n = 1) | 2.02 (n = 1) |
| CB A1AT | 0.567 (n = 1) | 0.438 (n = 1) | 2.82 (n = 1) | 0.816 ± 0.679 (n = 2) |

TABLE 1-continued

Production of Recombinant Vectors

|  | AAV2/1 | AAV2/2 | AAV2/5 | AAV2/8 |
|---|---|---|---|---|
| CMV rhCG | 8.78 ± 2.37 (n = 7) | 1.43 ± 1.18 (n = 2) | 1.63 ± 1.15 (n = 3) | 1.32 ± 0.87 (n = 3) |
| TBG rhCG | 8.51 ± 6.65 (n = 6) | 3.47 ± 2.09 (n = 5) | 5.26 ± 3.85 (n = 4) | 1.83 ± 0.98 (n = 5) |
| TBG cFIX | 1.24 ± 1.29 (n = 3) | 0.63 ± 0.394 (n = 6) | 3.74 ± 2.48 (n = 7) | 15.8 ± 15.0 (n = 5) |

Example 3: Serologic Analysis of Pseudotyped Vectors

C57BL/6 mice were injected with vectors of different serotypes of AAVCBA1AT vectors intramuscularly ($5 \times 10^{11}$ GC) and serum samples were collected 34 days later. To test neutralizing and cross-neutralizing activity of sera to each serotype of AAV, sera was analyzed in a transduction based neutralizing antibody assay [Gao, G. P., et al., (1996) *J Virol* 70, 8934-43]. More specifically, the presence of neutralizing antibodies was determined by assessing the ability of serum to inhibit transduction of 84-31 cells by reporter viruses (AAVCMVEGFP) of different serotypes. Specifically, the reporter virus AAVCMVEGFP of each serotype [at multiplicity of infection (MOI) that led to a transduction of 90% of indicator cells] was pre-incubated with heat-inactivated serum from animals that received different serotypes of AAV or from naïve mice. After 1-hour incubation at 37° C., viruses were added to 84-31 cells in 96 well plates for 48 or 72-hour, depending on the virus serotype. Expression of GFP was measured by FluoroImagin (Molecular Dynamics) and quantified by Image Quant Software. Neutralizing antibody titers were reported as the highest serum dilution that inhibited transduction to less than 50%.

The availability of GFP expressing vectors simplified the development of an assay for neutralizing antibodies that was based on inhibition of transduction in a permissive cell line (i.e., 293 cells stably expressing E4 from Ad5). Sera to selected AAV serotypes were generated by intramuscular injection of the recombinant viruses. Neutralization of AAV transduction by 1:20 and 1:80 dilutions of the antisera was evaluated (Table 2). Antisera to AAV1, AAV2, AAV5 and AAV8 neutralized transduction of the serotype to which the antiserum was generated (AAV5 and AAV8 to a lesser extent than AAV1 and AAV2) but not to the other serotype (i.e., there was no evidence of cross neutralization suggesting that AAV 8 is a truly unique serotype).

Human sera from 52 normal subjects were screened for neutralization against selected serotypes. No serum sample was found to neutralize AAV2/8 while AAV2/2 and AAV2/1 vectors were neutralized in 20% and 10% of sera, respec-tively. A fraction of human pooled IqG representing a collection of 60,000 individual samples did not neutralize AAV2/8, whereas AAV2/2 and AAV2/1 vectors were neutralized at titers of serum equal to 1/1280 and 1/640, respectively.

Example 4: In Vivo Evaluation of Different Serotypes of AAV Vectors

In this study, 7 recombinant AAV genomes, AAV2CBhA1AT, AAV2A1bhA1AT, AAV2CMVrhCG, AAV2TBGrhCG, AAV2TBGcFIX, AAV2CMVLacZ and AAV2TBGLacZ were packaged with capsid proteins of different serotypes. In all 7 constructs, minigene cassettes were flanked with AAV2 ITRs. cDNAs of human α-antitrypsin (A1AT) [Xiao, W., et al., (1999) *J Virol* 73, 3994-4003] β-subunit of rhesus monkey choriogonadotropic hormone (CG) [Zoltick, P. W. & Wilson, J. M. (2000) *Mol Ther* 2, 657-9] canine factor IX [Wang, L., et al., (1997) *Proc Nati Acad Sci USA* 94, 11563-6] and bacterial β-glactosidase (i.e., Lac Z) genes were used as reporter genes. For liver-directed gene transfer, either mouse albumin gene promoter (Alb) [Xiao, W. (1999), cited above] or human thyroid hormone binding globulin gene promoter (TBG) [Wang (1997), cited above] was used to drive liver specific expression of reporter genes. In muscle-directed gene transfer experiments, either cytomegalovirus early promoter (CMV) or chicken β-actin promoter with CMV enhancer (CB) was employed to direct expression of reporters.

For muscle-directed gene transfer, vectors were injected into the right tibialis anterior of 4-6 week old NCR nude or C57BL/6 mice (Taconic, Germantown, N.Y.) at a dose of $1 \times 10^{11}$ genome copies (GC) per animal. In liver-directed gene transfer studies, vectors were infused intraportally into 7-9 week old NCR nude or C57BL/6 mice (Taconic, Germantown, N.Y.), also at a dose of $1 \times 10^{11}$ genome copies (GC) per animal Serum samples were collected intraorbitally at different time points after vector administration. Muscle and liver tissues were harvested at different time points for cryosectioning and Xgal histochemical staining from animals that received the lacZ vectors. For the re-administration experiment, C56BL/6 mice initially received AAV2/1, 2/2, 2/5, 2/7 and 2/8CBA1AT vectors intramuscularly and followed for A1AT gene expression for 7 weeks. Animals were then treated with AAV2/8TBGcFIX intraportally and studied for cFIX gene expression.

ELISA based assays were performed to quantify serum levels of hA1AT, rhCG and cFIX proteins as described previously [Gao, G. P., et al., (1996) *J Virol* 70, 8934-43; Zoltick, P. W. & Wilson, J. M. (2000) *Mol Ther* 2, 657-9; Wang, L., et al., *Proc Natl Acad Sci USA* 94, 11563-6]. The experiments were completed when animals were sacrificed for harvest of muscle and liver tissues for DNA extraction

TABLE 2

Serological Analysis of New AAV Serotypes.

| Sera: | Immunization Vector | Serum dilution: | | Serum dilution: | | Serum dilution: | | Serum dilution: | |
|---|---|---|---|---|---|---|---|---|---|
| | | 1/20 | 1/80 | 1/20 | 1/80 | 1/20 | 1/80 | 1/20 | 1/80 |
| Group 1 | AAV2/1 | 0 | 0 | 100 | 100 | 100 | 100 | 100 | 100 |
| Group 2 | AAV2/2 | 100 | 100 | 0 | 0 | 100 | 100 | 100 | 100 |
| Group 3 | AAV2/5 | 100 | 100 | 100 | 100 | 16.5 | 16.5 | 100 | 100 |
| Group 4 | AAV2/8 | 100 | 100 | 100 | 100 | 100 | 100 | 26.3 | 60 | and quantitative analysis of genome copies of vectors present in target tissues by TaqMan using the same set of primers and probe as in titration of vector preparations [Zhang, Y., et al., (2001) Mol Ther 3, 697-707].

The performance of vectors base on the new serotypes were evaluated in murine models of muscle and liver-directed gene transfer and compared to vectors based on the known serotypes AAV1, AAV2 and AAV5. Vectors expressing secreted proteins (A1AT and CG-Table 3) were used to quantitate relative transduction efficiencies between different serotypes through ELISA analysis of sera. The cellular distribution of transduction within the target organ was evaluated using lacZ expressing vectors and X-gal histochemistry.

The performance of AAV vectors in skeletal muscle was analyzed following direct injection into the tibialis anterior muscles. Vectors contained the same AAV2 based genome with the immediate early gene of CMV or a CMV enhanced β-actin promoter driving expression of the transgene. Previous studies indicated that immune competent C57BL/6 mice elicit limited humoral responses to the human A1AT protein when expressed from AAV vectors [Xiao, W., et al., (1999) J Virol 73, 3994-4003].

In each strain, AAV2/1 vector produced the highest levels of A1AT and AAV2/2 vector the lowest, with AAV2/8 vectors showing intermediate levels of expression. Peak levels of CG at 28 days following injection of nu/nu NCR mice showed the highest levels from AAV2/7 and the lowest from AAV2/2 with AAV2/8 and AAV2/1 in between. Injection of AAV2/1 lacZ vectors yielded gene expression at the injection sites in all muscle fibers with substantially fewer lacZ positive fibers observed with AAV2/2 and AAV 2/8 vectors.

Similar murine models were used to evaluate liver-directed gene transfer. Identical doses of vector based on genome copies were infused into the portal veins of mice that were analyzed subsequently for expression of the transgene. Each vector contained an AAV2 based genome using previously described liver-specific promoters (i.e., albumin or thyroid hormone binding globulin) to drive expression of the transgene. More particularly, CMVCG and TBGCG minigene cassettes were used for muscle and liver-directed gene transfer, respectively. Levels of rhCG were defined as relative units (rUs×$10^3$). The data were from assaying serum samples collected at day 28, post vector administration (4 animals per group). As shown in Table 4, the impact of capsid proteins on the efficiency of transduction of A1AT vectors in nu/nu and C57BL/6 mice and CG vectors in C57BL/6 mice was consistent, i.e., AAV2/8 is the most efficient for pseudotype for liver-directed gene transfer.

TABLE 3

Expression of β-unit of Rhesus Monkey Chorionic Gonadotropin (rhCG) in Mouse Muscle and Liver.

| Vector | Muscle | Liver |
| --- | --- | --- |
| AAV2/1 | 4.5 ± 2.1 | 1.6 ± 1.0 |
| AAV2 | 0.5 ± 0.1 | 0.7 ± 0.3 |
| AAV2/5 | ND* | 4.8 ± 0.8 |
| AAV2/8 | 4.0 ± 0.7 | 76.0 ± 22.8 |

*Not determined in this experiment.

In all cases, AAV2/8 vectors yielded the highest levels of transgene expression that ranged from 16 to 110 greater than what was obtained with AAV2/2 vectors; expression from AAV2/5 was intermediate. Analysis of X-Gal stained liver sections of animals that received the corresponding lacZ vectors showed a correlation between the number of transduced cells and overall levels of transgene expression. DNAs extracted from livers of C57BL/6 mice who received the A1AT vectors were analyzed for abundance of vector DNA using real time PCR technology.

The amount of vector DNA found in liver 56 days after injection correlated with the levels of transgene expression (Table 4). For this experiment, a set of probe and primers targeting the SV40 polyA region of the vector genome was used for TaqMan PCR. Values shown are means of three individual animals with standard deviations. The animals were sacrificed at day 56 to harvest liver tissues for DNA extraction. These studies indicate that AAV8 is the most efficient vector for liver-directed gene transfer due to increased numbers of transduced hepatocytes.

TABLE 4

Real Time PCR Analysis for Abundance of AAV Vectors in nu/nu Mouse Liver Following Injection of 1 × $10^{11}$ Genome Copies of Vector.

| AAV vectors/Dose | Genome Copies per Cell |
| --- | --- |
| AAV2/1AlbA1AT | 0.6 ± 0.36 |
| AAV2AlbA1AT | 0.003 ± 0.001 |
| AAV2/5AlbA1AT | 0.83 ± 0.64 |
| AAV2/8AlbA1AT | 18 ± 11 |

The serologic data described above suggest that AAV2/8 vector should not be neutralized in vivo following immunization with the other serotypes. C57BL/6 mice received intraportal injections of AAV2/8 vector expressing canine factor IX ($10^{11}$ genome copies) 56 days after they received intramuscular injections of A1AT vectors of different serotypes. High levels of factor IX expression were obtained 14 days following infusion of AAV2/8 into naïve animals (17±2 μg/ml, N=4) which were not significantly different that what was observed in animals immunized with AAV2/1 (31±23 μg/ml, N=4), and AAV2/2 (16 μg/ml, N=2). This contrasts to what was observed in AAV2/8 immunized animals that were infused with the AAV2/8 factor IX vector in which no detectable factor IX was observed (<0.1 μg/ml, N=4).

Oligonucleotides to conserved regions of the cap gene did amplify sequences from rhesus monkeys that represented unique AAVs. Identical cap signature sequences were found in multiple tissues from rhesus monkeys derived from at least two different colonies. Full-length rep and cap open reading frames were isolated and sequenced from single sources. Only the cap open reading frames of the novel AAVs were necessary to evaluate their potential as vectors because vectors with the AAV8 capsids were generated using the ITRs and rep from AAV2. This also simplified the comparison of different vectors since the actual vector genome is identical between different vector serotypes. In fact, the yields of recombinant vectors generated using this approach did not differ between serotypes.

Vectors based on AAV8 appear to be immunologically distinct (i.e., they are not neutralized by antibodies generated against other serotypes). Furthermore, sera from humans do not neutralize transduction by AAV8 vectors, which is a substantial advantage over the human derived AAVs currently under development for which a significant proportion of the human population has pre-existing immunity that is neutralizing [Chirmule, N., et al., (1999) Gene Ther 6, 1574-83].

The tropism of the new vector is favorable for in vivo applications. Importantly, AAV2/8 provides a substantial advantage over the other serotypes in terms of efficiency of gene transfer to liver that until now has been relatively disappointing in terms of the numbers of hepatocytes stably transduced. AAV2/8 consistently achieved a 10 to 100-fold improvement in gene transfer efficiency as compared to the other vectors. The basis for the improved efficiency of AAV2/8 is unclear, although it presumably is due to uptake via a different receptor that is more active on the basolateral surface of hepatocytes. This improved efficiency will be quite useful in the development of liver-directed gene transfer where the number of transduced cells is critical, such as in urea cycle disorders and familial hypercholesterolemia.

Thus, the lack of pre-existing immunity to AAV8 and the favorable tropism of the vectors for liver indicates that vectors with AAV8 capsid proteins are suitable for use as vectors in human gene therapy and other in vivo applications.

Example 5: Tissue Tropism Studies

In the design of a high throughput functional screening scheme for novel AAV constructs, a non-tissue specific and highly active promoter, CB promoter (CMV enhanced chicken β-actin promoter) was selected to drive an easily detectable and quantifiable reporter gene, human α-antitrypsin gene. Thus only one vector for each new AAV clone needs to be made for gene transfer studies targeting 3 different tissues, liver, lung and muscle to screen for tissue tropism of a particular AAV construct. The following table summarizes data generated from novel AAV vectors in the tissue tropism studies (AAVCBA1AT). Table 5 reports data obtained (in μg A1AT/mL serum) at day 14 of the study.

TABLE 5

| Vector | Target Tissue | | |
|---|---|---|---|
| | Lung | Liver | Muscle |
| AAV2/1 | ND | ND | 45 ± 11 |
| AAV2/5 | 0.6 ± 0.2 | ND | ND |
| AAV2/8 | ND | 84 ± 30 | ND |

AAV vector carried CC10hA1AT minigene for lung specific expression were pseudotyped with capsids of novel AAVs were given to Immune deficient animals (NCR nude) in equal volume (50 μl each of the original preps without dilution) via intratracheal injections as provided in the following table. The vectors were also administered to immune competent animals (C57BL/6) in equal genome copies ($1 \times 10^{11}$ GC) as shown in the Table 6. ($1 \times 10^{11}$ GC per animal, C57BL/6, day 14, detection limit ≥0.033 μg/ml). As shown, AAV8 is the best liver transducer.

TABLE 6

| AAV Vector | μg of A1AT/ml with $1 \times 10^{11}$ vector |
|---|---|
| 2/1 | 0.076 ± 0.031 |
| 2/2 | 0.1 ± 0.09 |
| 2/5 | 0.0840.033 |
| 2/8 | 1.92 ± 1.3 |

Example 6: Model of Hypercholesterolemia

To further assess the effect of rAAV-mediated transgene expression by the AAV2/8 constructs of the invention, a further study was performed.

A. Vector Construction

AAV vectors packaged with AAV8 capsid proteins were constructed using a pseudotyping strategy [Hildinger M, et al., *J. Virol* 2001; 75:6199-6203]. Recombinant AAV genomes with AAV2 inverted terminal repeats (ITR) were packaged by triple transfection of 293 cells with the cis-plasmid, the adenovirus helper plasmid and a chimeric packaging construct, a fusion of the capsids of the novel AAV serotypes with the rep gene of AAV2. The chimeric packaging plasmid was constructed as previously described [Hildinger et al, cited above]. The recombinant vectors were purified by the standard $CsCl_2$ sedimentation method. To determine the yield TaqMan (Applied Biosystems) analysis was performed using probes and primers targeting the SV40 poly(A) region of the vectors [Gao G P, et al., *Hum Gene Ther.* 2000 Oct. 10; 11(15):2079-91]. The resulting vectors express the transgene under the control of the human thyroid hormone binding globulin gene promoter (TBG).

B. Animals

LDL receptor deficient mice on the C57Bl/6 background were purchased from the Jackson Laboratory (Bar Harbor, Me., USA) and maintained as a breeding colony. Mice were given unrestricted access to water and obtained a high fat Western Diet (high % cholesterol) starting three weeks prior vector injection. At day −7 as well at day 0, blood was obtained via retroorbital bleeds and the lipid profile evaluated. The mice were randomly divided into seven groups. The vector was injected via an intraportal injection as previously described ([Chen S J et al., *Mol Therapy* 2000; 2(3), 256-261]. Briefly, the mice were anaesthetized with ketamine and xylazine. A laparotomy was performed and the portal vein exposed. Using a 30 g needle the appropriate dose of vector diluted in 100 μl PBS was directly injected into the portal vein. Pressure was applied to the injection site to ensure a stop of the bleeding. The skin wound was closed and draped and the mice carefully monitored for the following day. Weekly bleeds were performed starting at day 14 after liver directed gene transfer to measure blood lipids. Two animals of each group were sacrificed at the timepoints week 6 and week 12 after vector injection to examine atherosclerotic plaque size as well as receptor expression. The remaining mice were sacrificed at week 20 for plaque measurement and determination of transgene expression.

| Vector | dose | N |
|---|---|---|
| Group 1 | AAV2/8-TBG-hLDLr | $1 \times 10^{12}$ gc | 12 |
| Group 2 | AAV2/8-TBG-hLDLr | $3 \times 10^{11}$ gc | 12 |
| Group 3 | AAV2/8-TBG-hLDLr | $1 \times 10^{11}$ gc | 12 |

C. Serum Lipoprotein and Liver Function Analysis

Blood samples were obtained from the retroorbital plexus after a 6 hour fasting period. The serum was separated from the plasma by centrifugation. The amount of plasma lipoproteins and liver transaminases in the serum were detected using an automatized clinical chemistry analyzer (ACE, Schiapparelli Biosystems, Alpha Wassermann)

D. Detection of Transgene Expression

LDL receptor expression was evaluated by immunofluorescence staining and Western blotting. For Western Blot frozen liver tissue was homogenized with lysis buffer (20 mM Tris, pH 7.4, 130 mM NaCl, 1% Triton X 100, proteinase inhibitor complete, EDTA-free, Roche, Mannheim, Germany). Protein concentration was determined using the Micro BCA Protein Assay Reagent Kit (Pierce, Rockford, Ill.). 40 µg of protein was resolved on 4-15% Tris-HCl Ready Gels (Biorad, Hercules, Calif.) and transferred to a nitrocellulose membrane (Invitrogen). To generate anti-hLDL receptor antibodies a rabbit was injected intravenously with an AdhLDLr prep ($1 \times 10^{13}$ gc). Four weeks later the rabbit serum was obtained and used for Western Blot. A 1:100 dilution of the serum was used as a primary antibody followed by a HRP-conjugated anti-rabbit IgG and ECL chemiluminescent detection (ECL Western Blot Detection Kit, Amersham, Arlington Heights, Ill.).

D. Immunocytochemistry

For determination of LDL receptor expression in frozen liver sections immunohistochemistry analyses were performed. 10 um cryostat sections were either fixed in acetone for 5 minutes, or unfixed. Blocking was obtained via a 1 hour incubation period with 10% of goat serum. Sections were then incubated for one hour with the primary antibody at room temperature. A rabbit polyclonal antibody anti-human LDL (Biomedical Technologies Inc., Stoughton, Mass.) was used diluted accordingly to the instructions of the manufacturer. The sections were washed with PBS, and incubated with 1:100 diluted fluorescein goat anti-rabbit IgG (Sigma, St Louis, Mo.). Specimens were finally examined under fluorescence microscope Nikon Microphot-FXA. In all cases, each incubation was followed by extensive washing with PBS. Negative controls consisted of preincubation with PBS, omission of the primary antibody, and substitution of the primary antibody by an isotype-matched non-immune control antibody. The three types of controls mentioned above were performed for each experiment on the same day.

E. Gene Transfer Efficiency

Liver tissue was obtained after sacrificing the mice at the designated time points. The tissue was shock frozen in liquid nitrogen and stored at −80° C. until further processing. DNA was extracted from the liver tissue using a QIAamp DNA Mini Kit (QIAGEN GmbH, Germany) according to the manufacturers protocol. Genome copies of AAV vectors in the liver tissue were evaluated using Taqman analysis using probes and primers against the SV40 poly(A) tail as described above.

F. Atherosclerotic Plaque Measurement

For the quantification of the atherosclerotic plaques in the mouse aorta the mice were anaesthetized (10% ketamine and xylazine, ip), the chest opened and the arterial system perfused with ice-cold phosphate buffered saline through the left ventricle. The aorta was then carefully harvested, slit down along the ventral midline from the aortic arch down to the femoral arteries and fixed in formalin. The lipid-rich atherosclerotic plaques were stained with Sudan IV (Sigma, Germany) and the aorta pinned out flat on a black wax surface. The image was captured with a Sony DXC-960 MD color video camera. The area of the plaque as well as of the complete aortic surface was determined using Phase 3 Imaging Systems (Media Cybernetics).

G. Clearance of $I^{125}$ LDL

Two animals per experimental group were tested. A bolus of $I^{125}$-labeled LDL (generously provided by Dan Rader, Upenn) was infused slowly through the tail vein over a period of 30 sec (1,000,000 counts of $[I^{125}]$-LDL diluted in 100 µl sterile PBS/animal) At time points 3 min, 30 min, 1.5 hr, 3 hr, 6 hr after injection a blood sample was obtained via the retro-orbital plexus. The plasma was separated off from the whole blood and 10 µl plasma counted in the gamma counter. Finally the fractional catabolic rate was calculated from the lipoprotein clearance data.

H. Evaluation of Liver Lipid Accumulation

Oil Red Staining of frozen liver sections was performed to determine lipid accumulation. The frozen liver sections were briefly rinsed in distilled water followed by a 2 minute incubation in absolute propylene glycol. The sections were then stained in oil red solution (0.5% in propylene glycol) for 16 hours followed by counterstaining with Mayer's hematoxylin solution for 30 seconds and mounting in warmed glycerin jelly solution.

For quantification of the liver cholesterol and triglyceride content liver sections were homogenized and incubated in chloroform/methanol (2:1) overnight. After adding of 0.05% $H_2SO_4$ and centrifugation for 10 minutes, the lower layer of each sample was collected, divided in two aliquots and dried under nitrogen. For the cholesterol measurement the dried lipids of the first aliquot were dissolved in 1% Triton X-100 in chloroform. Once dissolved, the solution was dried under nitrogen. After dissolving the lipids in ddH$_2$O and incubation for 30 minutes at 37° C. the total cholesterol concentration was measured using a Total Cholesterol Kit (Wako Diagnostics). For the second aliquot the dried lipids were dissolved in alcoholic KOH and incubated at 60° C. for 30 minutes. Then 1M $MgCl_2$ was added, followed by incubation on ice for 10 minutes and centrifugation at 14,000 rpm for 30 minutes. The supernatant was finally evaluated for triglycerides (Wako Diagnostics).

All of the vectors pseudotyped in an AAV2/8 capsid lowered total cholesterol, LDL and triglycerides as compared to the control. These test vectors also corrected phenotype of hypercholesterolemia in a dose-dependent manner. A reduction in plaque area for the AAV2/8 mice was observed in treated mice at the first test (2 months), and the effect was observed to persist over the length of the experiment (6 months).

Example 7: Functional Factor IX Expression and Correction of Hemophilia

A. Knock-Out Mice

Functional canine factor IX (FIX) expression was assessed in hemophilia B mice. Vectors with capsids of AAV1, AAV2, AAV5 or AAV8 were constructed to deliver AAV2 5' ITR—liver-specific promoter [LSP]-canine FIX—woodchuck hepatitis post-regulatory element (WPRE)—AAV2 3' ITR. The vectors were constructed as described in Wang et al, 2000, *Molecular Therapy* 2: 154-158), using the appropriate capsids.

Knock-out mice were generated as described in Wang et al, 1997. *Proc. Natl. Acad. Sci. USA* 94: 11563-11566. This model closely mimic the phenotypes of hemophilia B in human.

Vectors of different serotypes were delivered as a single intraportal injection into the liver of adult hemophiliac C57Bl/6 mice in a dose of $1 \times 10^{11}$ GC/mouse for the five different serotypes and a second AAV8 vector was also delivered at $1 \times 10^{11}$ GC/mouse. Control group was injected with $1 \times 10^{11}$ GC of AAV2/8 TBG LacZ3. Each group contains 5-10 male and female mice. Mice were bled bi-weekly after vector administration.

1. ELISA

The canine FIX concentration in the mouse plasma was determined by an ELISA assay specific for canine factor IX, performed essentially as described by Axelrod et al, 1990, *Proc. Natl. Acad. Sci. USA,* 87: 5173-5177 with modifications. Sheep anti-canine factor IX (Enzyme Research Laboratories) was used as primary antibody and rabbit anti-canine factor IX ((Enzyme Research Laboratories) was used as secondary antibody. Beginning at two weeks following injection, increased plasma levels of cFIX were detected for all test vectors. The increased levels were sustained at therapeutic levels throughout the length of the experiment, i.e., to 12 weeks. Therapeutic levels are considered to be 5% of normal levels, i.e., at about 250 ng/mL.

The highest levels of expression were observed for the AAV2/8 (at $10^{11}$), with sustained superphysiology levels cFIX levels (ten-fold higher than the normal level). Expression levels for AAV2/8 ($10^{11}$) were approximately 10 fold higher than those observed for AAV2/2 and AAV2/8 ($10^{10}$). The lowest expression levels, although still above the therapeutic range, were observed for AAV2/5.

2. In Vitro Activated Partial Thromboplastin Time (aPTT) Assay

Functional factor IX activity in plasma of the FIX knockout mice was determined by an in vitro activated partial thromboplastin time (aPTT) assay-Mouse blood samples were collected from the retro-orbital plexus into $\frac{1}{10}$ volume of citrate buffer. APTT assay was performed as described by Wang et al, 1997, *Proc. Natl. Acad. Sci. USA* 94: 11563-11566.

Clotting times by aPTT on plasma samples of all vector injected mice were within the normal range (approximately 60 sec) when measured at two weeks post-injection, and sustained clotting times in the normal or shorter than normal range throughout the study period (12 weeks).

Lowest sustained clotting times were observed in the animals receiving AAV2/8 ($10^{11}$). By week 12, AAV2/2 also induced clotting times similar to those for AAV2/8. However, this lowered clotting time was not observed for AAV2/2 until week 12, whereas lowered clotting times (in the 25-40 sec range) were observed for AAV2/8 beginning at week two.

Immuno-histochemistry staining on the liver tissues harvested from some of the treated mice is currently being performed. About 70-80% of hepatocytes are stained positive for canine FIX in the mouse injected with AAV2/8.cFIX vector.

B. Hemophilia B Dogs

Dogs that have a point mutation in the catalytic domain of the F.IX gene, which, based on modeling studies, appears to render the protein unstable, suffer from hemophilia B [Evans et al, 1989, Proc. Natl. Acad. Sci. USA, 86:10095-10099). A colony of such dogs has been maintained for more than two decades at the University of North Carolina, Chapel Hill. The homeostatic parameters of these doges are well described and include the absence of plasma F.IX antigen, whole blood clotting times in excess of 60 minutes, whereas normal dogs are 6-8 minutes, and prolonged activated partial thromboplastin time of 50-80 seconds, whereas normal dogs are β-28 seconds. These dogs experience recurrent spontaneous hemorrhages. Typically, significant bleeding episodes are successfully managed by the single intravenous infusion of 10 ml/kg of normal canine plasma; occasionally, repeat infusions are required to control bleeding.

Four dogs were injected intraportally with AAV.cFIX according to the schedule below. A first dog received a single injection with AAV2/2.cFIX at a dose of $3.7 \times 10^{11}$ genome copies (GC)/kg and was sacrificed at day 665 due to severe spinal hemorrhage. A second dog received a first injection of AAV2/2.cFIX ($2.8 \times 10^{11}$ GC/kg), followed by a second injection with AAV2/5.cFIX ($2.3 \times 10^{13}$ GC/kg) at day 1180. A third dog received a single injection with AAV2/2.cFIX at a dose of $4.6 \times 10^{12}$ GC/kg. The fourth dog received an injection with AAV2/2.cFIX ($2.8 \times 10^{12}$ GC/kg) and an injection at day 995 with AAV2/8.cFIX ($5 \times 10^{12}$ GC/kg).

The abdomen of hemophilia dogs were aseptically and surgically opened under general anesthesia and a single infusion of vector was administered into the portal vein. The animals were protected from hemorrhage in the pen-operative period by intravenous administration of normal canine plasma. The dog was sedated, intubated to induce general anesthesia, and the abdomen was shaved and prepped. After the abdomen was opened, the spleen was moved into the operative field. The splenic vein was located and a suture was loosely placed proximal to a small distal incision in the vein. An introduced was rapidly inserted into the vein, then the suture loosened and a 5 F cannula was threaded to an intravenous location near the portal vein threaded to an intravenous location near the portal vein bifurcation. After hemostasis was secured and the catheter balloon was inflated, approximately 5.0 ml of vector diluted in PBS was infused into the portal vein over a 5 minute interval. The vector infusion was followed by a 5.0 ml infusion of saline. The balloon was then deflated, the callula was removed and venous hemostatis was secured. The spleen was then replaced, bleeding vessels were cauterized and the operative wound was closed. The animal was extubated having tolerated the surgical procedure well. Blood samples were analyzed as described. [Wang et al, 2000, *Molecular Therapy* 2: 154-158]

The results are summarized in the table below. Dog C51, female, was 13.6 kg and 6.5 months old at the time of first injection. Dog C52, male, was 17.6 kg and 6.5 months old at first injection; and 17.2 kg and 45.2 months at second injection. Dog C55, male, was a 19.0 kg and 12.0 months at first injection. Dog D39, female, was a 5.0 kg and 2.8 months at first injection; 22.6 kg and 35.4 months old at the time of the second injection. In the table, GC refers to genome copies of the AAV vectors. WBCT were >60 minutes (except C52=42 min) before injection. Baseline aPTT for C51=98.4 sec, C52=97.7 sec; C55=145.1 sec; D39=97.8 sec. Bleeds post-treatment were spontaneous bleeding episodes happening in hemophilia B dogs post-AAV vector treatment that required treatment with plasma infusion.

| | Dog | Vector | Vector Dose (GC/kg) | Total GC Inject | Avg WBCT (min) | Avg aPTT (min) | Avg cFIX plasma (ng/mL) |
|---|---|---|---|---|---|---|---|
| 1st injection | C51 | AAV2-LSP.cFIX | $3.7 \times 10^{11}$ | $5 \times 10^{12}$ | 13.2 ± 2.1 | 77.5 ± 15.1 | 3.8 ± 1.0 |
| | C52 | AAV2-LSP.cFIX | $2.8 \times 10^{11}$ | $5.0 \times 10^{12}$ | 16.1 ± 3.5 | 81.5 ± 17.7 | 3.7 ± 1.1 |

Hemophilia B Dogs Injected with rAAV intraportally

| | Dog | Vector | Vector Dose (GC/kg) | Total GC Inject | Avg WBCT (min) | Avg aPTT (min) | Avg cFIX plasma (ng/mL) |
|---|---|---|---|---|---|---|---|
| | C55 | AAV2-LSP.cFIX WPRE | $4.6 \times 10^{12}$ | $8.7 \times 10^{13}$ | $10.2 \pm 2.2$ | $46.4 \pm 6.1$ | $259.7 \pm 28.5$ |
| | D39 | AAV2-LSPcFIX WPRE | $2.8 \times 10^{12}$ | $1.4 \times 10^{13}$ | $11.5 \pm 2.6$ | $59.1 \pm 6.3$ | $34.4 \pm 9.8$ |
| 2nd injection | C52 | AAV2/5-LSP.cFIX WPRE | $2.3 \times 10^{13}$ | $4.0 \times 10^{14}$ | $12.9 \pm 1.1$ | $41.9 \pm 2.7$ | $817.3 \pm 102.1$ |
| | D39 | AAV2/8-LSP.cFIX WPRE | $5.0 \times 10^{12}$ | $1.1 \times 10^{14}$ | $12.6 \pm 1.5$ | | $656.9 \pm 1.1$ |

Hemophilia B Dogs Injected with rAAV intraportally

1. Whole Blood Clotting Time (WBCT)

WBCT following injection with the AAV2/2 vectors were somewhat variable, ranging from about 6.5 min to 30 minutes. WBCT for a normal dog is 6-12 min Sharp drops in WBCT were observed immediately upon injection with the AAV2/8 or AAV2/5 vectors The sharp drop was also observed in C55 injected with AAV2 (d2=9 min), and for C51 and C52, the early data point for WBCT were not checked. The sharp drop is believed to be due to the dog plasma infusion before and after the surgery. WBCT is an assay very sensitive to low level of FIX, it is not very sensitive to the actual level of FIX (aPTT is more relevant).

2. aPTT Assay

Clotting times by aPTT on plasma samples of all vector injected dogs were variable over the first approximately 700 days, at which time clotting times leveled in the normal range (40-60 sec, normal dog: 24-32 sec). A sharp drop into the normal range was observed following each of the second injections (AAV2/8 or AAV2/5). While clotting times were not sustained in the normal range, clotting times were reduced to levels below those observed prior to the second injection.

For aPTT, normal dogs are 24-32 sec, and hemophilia B dogs are 80-106 sec. For C51 and C52 who received low dose of AAV2.cFIX vector, average aPTT after treatment remain at 77.5 and 81.5 sec, not significantly different from hemophilia B dogs without treatment. Higher dose of AAV2 improved the average aPTT to 59.1 and 46.4 sec, respectively for D39 and C55. After the treatment of AAV2/5, the average aPTT for C52 improved significantly from 81.5 sec to 41.9 sec. And for D39, after the AAV2/8 treatment, the average aPTT improve from 59.1 sec.

3. Canine Factor IX ELISA cFIX levels were detectable following the first set of injections, albeit below therapeutic levels. Following injection with AAV2/8 and AAV2/5, levels of cFIX rose spiked into the therapeutic range and then leveled off within the therapeutic range (normal is 5 µg/ml in plasma, therapeutic level is 5% of normal level which is 250 ng/ml).

The first three weeks of WBCT, aPTT and cFIX antigen are affected by the dog plasma infusion before and after the surgery. It is hard to conclude the drop of clotting time or the rise of cFIX antigen level is due to the vector or the plasma infusion for the first 3 weeks. However, it is interesting to note that the quick and dramatic rise of cFIX antigen after 2/5 and 2/8 vector injection. This is unique to AAV2/5 and 2/8 injected dogs and could be attributed to AAV2/5 and 2/8 vectors rather than the normal dog plasma infusion, since all dogs received similar amount of normal dog plasma infusion for the surgery. Three days after AAV2/8 injection, the level of cFIX in the plasma of D39 reached 9.5 µg/ml and peaked at 10.4 µg/ml at day 6, twice as much as the normal level (5 µg/ml). The cFIX level gradually decreased to the average of 817 ng/ml (C52, AAV2/5) and 657 ng/ml (D39, AAV2/8). In C52, 3 days after injection of AAV2/5 vector, the cFIX level reached 2.6 µg/ml and peaked at 4.6 µg/ml at day 7. In C55, who received AAV2 vector at the dose similar to that of AAV2/8 injected to D39, peaked only at 2.2 µg/ml at day 3, then gradually dropped and maintained at 5% of normal level of cFIX.

The doses of vector received by C55 (AAV2, $4.6 \times 10^{12}$ GC/kg) and the second injection in D39 (AAV2/8, $5 \times 10^{12}$ GC/kg) were very close. However, the cFIX expression levels raised in D39 by AAV2/8 vector (average 657-34=623 ng/ml, 12.5% of normal level) was 2.5 fold higher than that in C55 (average 259 ng/ml, 5% of normal level). This suggests AAV2/8 is 2.5 fold more potent than AAV2 in dogs injected intraportally with similar dose of vectors. And in the same dog D39, the second injection of two fold higher dose of AAV2/8 dramatically increased the cFIX level from 0.7% to 13.1%, 18.7 fold higher than the first injection. And in C52, the second injection of $2.3 \times 10^{13}$ GC/ml of AAV2/5 vector resulted in average 817 ng/ml (16.3% of normal level) of cFIX in the plasma. This was only marginally higher (1.3 fold) than the cFIX level raised in D39 by AAV2/8 (average 623 ng/ml, 12.5% of normal level,). However, the dose of AAV2/5 injected in C52 was 4.6 fold higher than the dose of AAV2/8 injected in D39. This suggests that AAV2/8 vector is also more potent than AAV2/5 vector in dogs.

The first injection of AAV2 vectors did not block the success of transduction by AAV2/5 and AAV2/8 vectors after the second injection in dogs. Readministration using a different serotype of AAV vector can be used as an approach to treat animals or humans who have been previously exposed to AAV2 or treated with AAV2 vectors.

Example 8: Mouse Model of Liver Enzyme Disorder

The AAV2/8 vector generated as described herein was studied for its efficiency in transferring the liver enzyme gene ornithine transcarbamylase (OTC) in an accepted animal model for OTC deficiency [X. Ye et al, *Pediatric Research*, 41(4):527-534 (1997); X. Ye et al, *J. Biol. Chem.*, 271(7):3639-3646 (February 1996)]. The results of this experiment (data not shown) demonstrate that an AAV2/8 vector of the invention carrying the ornithine transcarbamylase (OTC) gene was observed to correct OTC deficiency.

Example 9: In Vivo Expression of Factor VIII

Three groups of C57BL/6 mice are injected via the portal vein with either 3×10[11] genome copies AAV vector carrying the Factor VIII heavy chain (FVIII-HC), 3×10[11] genome copies of AAV vector carrying Factor VIII light chain (FVIII-LC), or 3×10[11] particles of both AAV-FVIII-HC and AAV-FVIII-LC. In addition, a group of four animals is injected with 3×10[11] particles of AAV carrying Factor IX (FIX), which is known to be useful in treatment of hemophilia B. It has been shown that this strain of mice does not elicit an immune response to human FVIII when the gene is delivered to the liver via an adenoviral vector (Connelly et al., Blood 87:4671-4677 [1996]).

These experiments will demonstrate the feasibility of producing biologically active FVIII using two AAV vectors to independently deliver the heavy and light chains of FVIII.

Blood samples are collected in sodium citrate via the retro-orbital plexus at biweekly intervals for the first 2 months and at monthly intervals thereafter for 6 months and at 11 months. Very high levels of FVIII light chain will be expressed in animals injected with AAV-FVIII-LC alone or both vectors.

In order to assess the amount of biologically active human FVIII produced in the animals, a modified ChromZ assay is used. Since this assay detects both human and murine FVIII, the amount of FVIII present in the plasma before and after adsorption to an antibody specific to human FVIII is determined. The amount of FVIII remaining in the plasma after adsorption represents the amount of active murine FVIII and the difference represented the amount of active human FVIII. The modified ChromZ assay will indicate that only those animals injected with both vectors produced biologically active FVIII.

The animals are expected to maintain physiological levels of active protein for more than 11 months, without waning.

All publications cited in this specification, and any sequence listings associated therewith, are incorporated herein by reference. While the invention has been described with reference to particularly preferred embodiments, it will be appreciated that modifications can be made without departing from the spirit of the invention.

The invention claimed is:

1. A cultured host cell containing a recombinant nucleic acid molecule encoding an AAV vp1 capsid protein having a sequence comprising amino acids 1 to 738 of SEQ ID NO: 2 (AAV8) or a sequence at least 95% identical to the full length of amino acids 1 to 738 of SEQ ID NO: 2, wherein the recombinant nucleic acid molecule further comprises a heterologous non-AAV sequence.

2. The cultured host cell according to claim 1, which further comprises a functional rep gene.

3. A cultured host cell containing a recombinant nucleic acid molecule encoding an AAV vp2 capsid protein having a sequence comprising amino acids 138 to 738 of SEQ ID NO: 2 (AAV8) or a sequence at least 95% identical to the full length of amino acids 138 to 738 of SEQ ID NO: 2, wherein the recombinant nucleic acid molecule further comprises a heterologous non-AAV sequence.

4. The cultured host cell according to claim 3, which further comprises a functional rep gene.

5. A cultured host cell containing a recombinant nucleic acid molecule encoding an AAV vp3 capsid protein having a sequence comprising amino acids 204 to 738 of SEQ ID NO: 2 (AAV8) or a sequence at least 95% identical to the full length of amino acids 204 to 738 of SEQ ID NO: 2, wherein the recombinant nucleic acid molecule further comprises a heterologous non-AAV sequence.

6. The cultured host cell according to claim 5, which further comprises a functional rep gene.

7. A cultured host cell containing a recombinant nucleic acid molecule comprising
   (a) nucleotides 2121 to 4334 of SEQ ID NO: 1 or a sequence at least 95% identical to nucleotides 2121 to 4334 of SEQ ID NO: 1,
   (b) nucleotides 2532 to 4334 of SEQ ID NO: 1 or a sequence at least 95% identical to nucleotides 2532 to 4334 of SEQ ID NO: 1, or
   (c) nucleotides 2730 to 4334 of SEQ ID NO: 1 or a sequence at least 95% identical to nucleotides 2730 to 4334 of SEQ ID NO: 1,
   wherein the recombinant nucleic acid molecule further comprises a heterologous non-AAV sequence.

8. The cultured host cell according to claim 7, which further comprises a rep gene.

9. The cultured host cell according to claim 7, wherein said nucleotide sequence is at least 95% identical to nucleotides 2121 to 4334 of SEQ ID NO: 1.

10. The cultured host cell according to claim 7, wherein said nucleotide sequence is at least 98% identical to nucleotides 2121 to 4334 of SEQ ID NO: 1.

11. The cultured host cell according to claim 7, wherein said nucleotide sequence is at least 99% identical to nucleotides 2121 to 4334 of SEQ ID NO: 1.

12. The cultured host cell according to claim 7, wherein said nucleotide sequence is at least 95% identical to nucleotides 2532 to 4334 of SEQ ID NO: 1.

13. The cultured host cell according to claim 7, wherein said nucleotide sequence is at least 98% identical to nucleotides 2532 to 4334 of SEQ ID NO: 1.

14. The cultured host cell according to claim 7, wherein said nucleotide sequence is at least 99% identical to nucleotides 2532 to 4334 of SEQ ID NO: 1.

15. The cultured host cell according to claim 7, wherein said nucleotide sequence is at least 95% identical to nucleotides 2730 to 4334 of SEQ ID NO: 1.

16. The cultured host cell according to claim 7, wherein said nucleotide sequence is at least 98% identical to nucleotides 2730 to 4334 of SEQ ID NO: 1.

17. The cultured host cell according to claim 7, wherein said nucleotide sequence is at least 99% identical to nucleotides 2730 to 4334 of SEQ ID NO: 1.

18. The cultured host cell according to claim 2, wherein the rep gene is from AAV2.

19. The cultured host cell according to claim 4, wherein the rep gene is from AAV2.

20. The cultured host cell according to claim 6, wherein the rep gene is from AAV2.

21. The cultured host cell according to claim 8, wherein the rep gene is from AAV2.

22. The cultured host cell according to claim 1, wherein the recombinant nucleic acid molecule is a plasmid.

23. The cultured host cell according to claim 3, wherein the recombinant nucleic acid molecule is a plasmid.

24. The cultured host cell according to claim 5, wherein the recombinant nucleic acid molecule is a plasmid.

25. The cultured host cell according to claim 7, wherein the recombinant nucleic acid molecule is a plasmid.

\* \* \* \* \*